(12) United States Patent
Negrete et al.

(10) Patent No.: US 11,045,554 B1
(45) Date of Patent: Jun. 29, 2021

(54) LIPID-COATED PARTICLES FOR TREATING VIRAL INFECTIONS

(71) Applicants: National Technology & Engineering Solutions of Sandia, LLC, Albuquerque, NM (US); STC.UNM, Albuquerque, NM (US)

(72) Inventors: Oscar Negrete, Livermore, CA (US); C. Jeffrey Brinker, Albuquerque, NM (US); Torri Rinker, San Francisco, CA (US); Annette Estelle LaBauve, Hayward, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 16/443,316

(22) Filed: Jun. 17, 2019

Related U.S. Application Data

(60) Provisional application No. 62/689,037, filed on Jun. 22, 2018.

(51) Int. Cl.
| | | |
|---|---|---|
| A61K 31/4965 | (2006.01) | |
| A61K 47/69 | (2017.01) | |
| A61K 47/54 | (2017.01) | |
| A61K 31/517 | (2006.01) | |

(52) U.S. Cl.
CPC ...... *A61K 47/6915* (2017.08); *A61K 31/4965* (2013.01); *A61K 31/517* (2013.01); *A61K 47/543* (2017.08); *A61K 47/6913* (2017.08); *A61K 47/6917* (2017.08)

(58) Field of Classification Search
None
See application file for complete search history.

(56) References Cited

U.S. PATENT DOCUMENTS

| | | |
|---|---|---|
| 8,734,816 B2 | 5/2014 | Liu et al. |
| 8,992,984 B1 | 3/2015 | Brinker et al. |
| 9,480,653 B2 | 11/2016 | Brinker et al. |
| 9,579,283 B2 | 2/2017 | Brinker et al. |
| 9,580,393 B2 | 2/2017 | Golden et al. |
| 9,855,217 B2 | 1/2018 | Brinker et al. |
| 10,022,327 B2 | 7/2018 | Brinker et al. |
| 2013/0085133 A1 | 4/2013 | Severson et al. |

(Continued)

FOREIGN PATENT DOCUMENTS

| | | |
|---|---|---|
| WO | WO 2014/093635 A1 | 6/2014 |
| WO | WO 2015/042268 A1 | 3/2015 |

(Continued)

OTHER PUBLICATIONS

Schroeder et al., J. Med. Chem., 2014, 57(20), pp. 8608-8621. (Year: 2014).*

(Continued)

*Primary Examiner* — Brian Gulledge
(74) *Attorney, Agent, or Firm* — Helen S. Baca

(57) ABSTRACT

The present invention relates to lipid-coated particles for treating viral infections, including viral encephalitis infections. In particular, an antiviral compound can be disposed within the lipid-coated particle, thereby providing an antiviral carrier. Methods of making and using such carriers are described herein.

20 Claims, 20 Drawing Sheets

Specification includes a Sequence Listing.

ML336 antiviral

* DSPC (77.5%)
* DSPE-PEG (2.5%)
* Cholesterol (20%)

(56) References Cited

U.S. PATENT DOCUMENTS

| | | | |
|---|---|---|---|
| 2014/0079774 A1* | 3/2014 | Brinker | A61P 35/00 424/450 |
| 2014/0301951 A1 | 10/2014 | Liu et al. | |
| 2015/0010475 A1 | 1/2015 | Brinker et al. | |
| 2015/0164798 A1 | 6/2015 | Brinker et al. | |
| 2015/0272885 A1 | 10/2015 | Ashley et al. | |
| 2015/0320681 A1 | 11/2015 | Brinker et al. | |
| 2016/0090603 A1 | 3/2016 | Carnes et al. | |
| 2016/0106671 A1 | 4/2016 | Brinker et al. | |
| 2016/0151482 A1 | 6/2016 | Carnes et al. | |
| 2016/0287717 A1 | 10/2016 | Brinker et al. | |
| 2016/0338954 A1 | 11/2016 | Brinker et al. | |
| 2017/0165375 A1 | 6/2017 | Ashley et al. | |
| 2017/0232115 A1 | 8/2017 | Ashley et al. | |
| 2018/0028686 A1 | 2/2018 | Brinker et al. | |
| 2018/0049984 A1 | 2/2018 | Brinker et al. | |
| 2018/0105430 A1 | 4/2018 | Carnes et al. | |
| 2018/0110831 A1 | 4/2018 | Brinker et al. | |
| 2018/0169009 A1 | 6/2018 | Johnson et al. | |
| 2018/0344641 A1 | 12/2018 | Brinker et al. | |
| 2019/0022235 A1 | 1/2019 | Durfee et al. | |
| 2019/0091150 A1 | 3/2019 | Brinker et al. | |

FOREIGN PATENT DOCUMENTS

| | | |
|---|---|---|
| WO | WO 2015/042279 A1 | 3/2015 |
| WO | WO 2017/023407 A2 | 2/2017 |
| WO | WO 2017/041032 A1 | 3/2017 |
| WO | WO 2017/041033 A1 | 3/2017 |
| WO | WO 2017/120504 A1 | 7/2017 |

OTHER PUBLICATIONS

U.S. Appl. No. 15/757,269, filed Mar. 2, 2018, Brinker et al.
U.S. Appl. No. 15/788,634, filed Oct. 19, 2017, Brinker et al.
U.S. Appl. No. 15/858,923, filed Dec. 29, 2017, Brinker et al.
U.S. Appl. No. 15/887,619, filed Feb. 2, 2018, Brinker et al.
U.S. Appl. No. 15/025,557, filed Jul. 2, 2018, Brinker et al.
U.S. Appl. No. 15/141,725, filed Sep. 25, 2018, Brinker et al.
Atasheva S et al., *Venezuelan equine encephalitis virus capsid protein inhibits nuclear import in Mammalian but not in mosquito cells*. J. Virol. 2008;82(8):4028-41.
Barbu EM et al., *Beta-neurexin is a ligand for the Staphylococcus aureus MSCRAMM SdrC*. PLoS Pathog. 2010;6(1):e1000726 (11 pp.).
Bimbo LM et al., *Inhibition of Influenza A virus infection in vitro by saliphenylhalamide-loaded porous silicon nanoparticles*. ACS Nano 2013;7(8):6884-93.
Braun K et al., *Dissolution kinetics of mesoporous silica nanoparticles in different simulated body fluids*. J. Sol-Gel Sci. Technol. 2016;79(2):319-27.
Butler KS et al., *Protocells: modular mesoporous silica nanoparticle-supported lipid bilayers for drug delivery*. Small 2016;12(16):2173-85.
Cauda V et al., *Colchicine-loaded lipid bilayer-coated 50 nm mesoporous nanoparticles efficiently induce microtubule depolymerization upon cell uptake*. Nano Lett. 2010;10(7):2484-92.
Cello J et al., *Chemical synthesis of poliovirus cDNA: generation of infectious virus in the absence of natural template*. Science 2002;297(5583):1016-8.
Cheng T et al., *Computation of octanol—water partition coefficients by guiding an additive model with knowledge*. J. Chem. Inf. Model. 2007;47:2140-8.
Chung DH et al., *Discovery of a broad-spectrum antiviral compound that inhibits pyrimidine biosynthesis and establishes a type 1 interferon-independent antiviral state*. Antimicrob. Agents Chemother. 2016;60(8):4552-62.
Chung DH et al., *Discovery of a novel compound with anti-venezuelan equine encephalitis virus activity that targets the nonstructural protein 2*. PLoS Pathog. 2014;10(6):e1004213 (10 pp.).

Cokol M et al., *Finding nuclear localization signals*. EMBO Rep. 2000;1(5):411-5.
Durfee PN et al., *Mesoporous silica nanoparticle-supported lipid bilayers (protocells) for active targeting and delivery to individual leukemia cells*. ACS Nano 2016;10(9):8325-45.
Ertl P et al., *Fast calculation of molecular polar surface area as a sum of fragment-based contributions and its application to the prediction of drug transport properties*. J. Med. Chem. 2000;43:3714-7.
Gao F et al., *Monodispersed mesoporous silica nanoparticles with very large pores for enhanced adsorption and release of DNA*. J. Phys. Chem. B 2009;113(6):1796-804.
Gibson DG et al., *Creation of a bacterial cell controlled by a chemically synthesized genome*. Science 2010;329(5987):52-6.
Giordano RJ et al., *Biopanning and rapid analysis of selective interactive ligands*. Nat. Med. 2001;7(11):1249-53.
Giordano RJ et al., *From combinatorial peptide selection to drug prototype (I): targeting the vascular endothelial growth factor receptor pathway*. Proc. Nat'l Acad. Sci. USA 2010;107(11):5112-7.
Giordano RJ et al., *Structural basis for the interaction of a vascular endothelial growth factor mimic peptide motif and its corresponding receptors*. Chem. Biol. 2005;12(10):1075-83.
Gonzalez Porras MA et al., *A novel approach for targeted delivery to motoneurons using cholera toxin-B modified protocells*. J. Neurosci. Methods 2016;273:160-74.
Han DH et al., *Direct cellular delivery of human proteasomes to delay tau aggregation*. Nat. Commun. 2014;5:5633 (8 pp.).
Han N et al., *Hybrid lipid-capped mesoporous silica for stimuli-responsive drug release and overcoming multidrug resistance*. ACS Appl. Mater. Interfaces 2015;7(5):3342-51.
Harmon B et al., *Rift Valley fever virus strain MP-12 enters mammalian host cells via caveola-mediated endocytosis*. J. Virol. 2012;86:12954-70.
Jackson RJ et al., *Expression of mouse interleukin-4 by a recombinant ectromelia virus suppresses cytolytic lymphocyte responses and overcomes genetic resistance to mousepox*. J. Virol. 2001;75(3):1205-10.
Jonsson CB et al., *Efficacy of a ML336 derivative against Venezuelan and eastern equine encephalitis viruses*. Antiviral Res. 2019;167:25-34.
Julander JG et al., *C3H/HeN mouse model for the evaluation of antiviral agents for the treatment of Venezuelan equine encephalitis virus infection*. Antiviral Res. 2008;78(3):230-41.
Julander JG et al., *Treatment of Venezuelan equine encephalitis virus infection with (-)-carbodine*. Antiviral Res. 2008;80(3):309-15.
Kehn-Hall K et al., *Modulation of GSK-3beta activity in Venezuelan equine encephalitis virus infection*. PLoS One 2012;7(4):e34761 (12 pp.).
Kolonin MG et al., *Ligand-directed surface profiling of human cancer cells with combinatorial peptide libraries*. Cancer Res. 2006;66(1):34-10.
LaBauve AE et al., *Lipid-coated mesoporous silica nanoparticles for the delivery of the ML336 antiviral to inhibit encephalitic alphavirus infection*. Sci. Rep. 2018;8:13990 (13 pp.).
LaBauve AE et al., Supporting information for *Lipid-coated mesoporous silica nanoparticles for the delivery of the ML336 antiviral to inhibit encephalitic alphavirus infection*. Sci. Rep. 2018;8:13990 (8 pp.).
LaCasse EC et al., *Nuclear localization signals overlap DNA- or RNA-binding domains in nucleic acid-binding proteins*. Nucl. Acids Res. 1995;23:1647-56.
Lambris JD et al., *Complement evasion by human pathogens*. Nat. Rev. Microbiol. 2008;6(2):132-42.
Langsjoen RM et al., *Host oxidative folding pathways offer novel anti-chikungunya virus drug targets with broad spectrum potential*. Antiviral Res. 2017;143:246-51.
Li Z et al., *Identification and characterization of a novel peptide ligand of epidermal growth factor receptor for targeted delivery of therapeutics*. FASEB J. 2005;19(14):1978-85.
Li Z et al., *Mesoporous silica nanoparticles in biomedical applications*. Chem. Soc. Rev. 2012;41(7):2590-605.

(56) References Cited

OTHER PUBLICATIONS

Lin YS et al., *Stability of small mesoporous silica nanoparticles in biological media.* Chem. Commun. (Camb.) 2011;47:532-4.

Lin YS et al., *Synthesis and characterization of biocompatible and size-tunable multifunctional porous silica nanoparticles.* Chem. Mater. 2009;21:3979-86.

Lionakis MS, *Development of a ligand-directed approach to study the pathogenesis of invasive aspergillosis.* Infect. Immun. 2005;73(11):7747-58.

Liu J et al., *Porous nanoparticle supported lipid bilayers (protocells) as delivery vehicles.* J. Am. Chem. Soc. 2009;131(4):1354-5.

Lo A et al., *Hepatocellular carcinoma cell-specific peptide ligand for targeted drug delivery.* Mol. Cancer Ther. 2008;7(3):579-89.

Lu J et al., *Biocompatibility, biodistribution, and drug-delivery efficiency of mesoporous silica nanoparticles for cancer therapy in animals.* Small 2010;6(16):1794-805.

Lu J et al., *Mesoporous silica nanoparticles as a delivery system for hydrophobic anticancer drugs.* Small 2007;3(8):1341-6.

Madsen C et al., *Small molecule inhibitors of Ago2 decrease Venezuelan equine encephalitis virus replication.* Antiviral Res. 2014;112:26-37.

Maleki A et al., *Mesoporous silica materials: from physicochemical properties to enhanced dissolution of poorly water-soluble drugs.* J. Control. Release 2017;262:329-47.

Mamaeva V et al., *Mesoporous silica nanoparticles in medicine—recent advances.* Adv. Drug Deliv. Rev. 2013;65(5):689-702.

Meng H et al., *Use of a lipid-coated mesoporous silica nanoparticle platform for synergistic gemcitabine and paclitaxel delivery to human pancreatic cancer in mice.* ACS Nano 2015;9(4):3540-57.

Moore NM et al., *The effect of endosomal escape peptides on in vitro gene delivery of polyethylene glycol-based vehicles.* J. Gene Med. 2008;10(10):1134-49.

Mornet S et al., *The formation of supported lipid bilayers on silica nanoparticles revealed by cryoelectron microscopy.* Nano Lett. 2005;5(2):281-5.

Nagata LP et al., *Vaccines and therapeutics for the encephalitic alphaviruses.* Future Virol. 2013;8(7):661-74.

Petrauskas AA et al., *ACD/Log P method description.* Perspect. Drug Discovery Des. 2000;19:99-116.

Poon IK et al., *Molecular mechanisms of late apoptotic/necrotic cell clearance.* Cell Death Differ. 2010;17(3):381-97.

Riikonen J et al., *Systematic in vitro and in vivo study on porous silicon to improve the oral bioavailability of celecoxib.* Biomaterials 2015;52:44-55.

Roggers RA et al., *Chemically reducible lipid bilayer coated mesoporous silica nanoparticles demonstrating controlled release and HeLa and normal mouse liver cell biocompatibility and cellular internalization.* Mol. Pharm. 2012;9(9):2770-7.

Rosenholm JM et al., *Towards multifunctional, targeted drug delivery systems using mesoporous silica nanoparticles—opportunities & challenges.* Nanoscale 2010;2(10):1870-83.

Russell CA et al., *The potential for respiratory droplet-transmissible A/H5N1 influenza virus to evolve in a mammalian host.* Science 2012;336(6088):1541-7.

Schecter S et al., *Novel inhibitors targeting Venezuelan equine encephalitis virus capsid protein identified using In Silico Structure-Based-Drug-Design.* Sci. Rep. 2017;7:art. No. 17705 (16 pp.).

Schroeder CE et al., *Development of (E)-24(1,4-dimethylpiperazin-2-ylidene)amino)-5-nitro-N-phenylbenzamide, ML336: Novel 2-amidinophenylbenzamides as potent inhibitors of Venezuelan equine encephalitis virus.* J. Med. Chem. 2014;57(20):8608-21.

Shen D et al., *Biphase stratification approach to three-dimensional dendritic biodegradable mesoporous silica nanospheres.* Nano Lett. 2014;14(2):923-32.

Sherman MB et al., *Stability of cucumber necrosis virus at the quasi-6-fold axis affects zoospore transmission.* J. Virol. 2017;91:1-12.

Sidwell RW et al., *Viruses of the Bunya- and Togaviridae families: potential as bioterrorism agents and means of control.* Antiviral Res. 2003;57(1-2):101-11.

Slowing II et al., *Mesoporous silica nanoparticles as controlled release drug delivery and gene transfection carriers.* Adv. Drug Deliv. Rev. 2008;60(11):1278-88.

Tang F et al., *Mesoporous silica nanoparticles: synthesis, biocompatibility and drug delivery.* Adv. Mater. 2012;24(12):1504-34.

Tarn D et al., *Mesoporous silica nanoparticle nanocarriers: bio functionality and biocompatibility.* Acc. Chem. Res. 2013;46(3):792-801.

Teng IT et al., *Phospholipid-functionalized mesoporous silica nanocarriers for selective photodynamic therapy of cancer.* Biomaterials 2013;34(30):7462-70.

Thomas DR et al., *Identification of novel antivirals inhibiting recognition of Venezuelan equine encephalitis virus capsid protein by the importin α/β1 heterodimer through high-throughput screening.* Antiviral Res. 2018;151:8-19.

Tonelli RR et al., *Role of the gp85/trans-sialidases in Trypanosoma cruzi tissue tropism: preferential binding of a conserved peptide motif to the vasculature in vivo.* PLoS Negl. Trop. Dis. 2010;4(11):e864 (8 pp.).

Townson JL et al., *Re-examining the size/charge paradigm: differing in vivo characteristics of size- and charge-matched mesoporous silica nanoparticles.* J. Am. Chem. Soc. 2013;135:16030-3.

Tumpey TM et al., *Characterization of the reconstructed 1918 Spanish influenza pandemic virus.* Science. 2005;310(5745):77-80.

van Schooneveld MM et al., *Improved biocompatibility and pharmacokinetics of silica nanoparticles by means of a lipid coating: a multimodality investigation.* Nano Lett. 2008;8(8): 2517-25.

Vivero-Escoto JL et al., *Mesoporous silica nanoparticles for intracellular controlled drug delivery.* Small 2010;6(18):1952-67.

von Haartman E et al., *On the intracellular release mechanism of hydrophobic cargo and its relation to the biodegradation behavior of mesoporous silica nanocarriers.* Eur. J. Pharm. Sci. 2016;95:17-27.

Walker MJ, *Training ACD/LogP with experimental data.* QSAR Comb. Sci. 2004;23:515-20.

Wang D et al., *The eradication of breast cancer cells and stem cells by 8 hydroxyquinoline-loaded hyaluronan modified mesoporous silica nanoparticle-supported lipid bilayers containing docetaxel.* Biomaterials 2013;34(31):7662-73.

Wang LS et al., *Biofunctionalized phospholipid-capped mesoporous silica nanoshuttles for targeted drug delivery: improved water suspensibility and decreased nonspecific protein binding.* ACS Nano 2010;4(8):4371-9.

Weber ND et al., *DNA cleavage enzymes for treatment of persistent viral infections: recent advances and the pathway forward.* Virology 2014;454-455:353-61.

Weis, K, *Importins and exportins: how to get in and out of the nucleus.* [published erratum appears in Trends Biochem. Sci. Jul. 1998;23(7):235] Trends Biochem. Sci. 1998;23:185-9.

Zacks MA and Paessler S, *Encephalitic alphaviruses.* Vet. Microbiol. 2010;140(3-4):281-6.

Zhang K et al., *Facile large-scale synthesis of monodisperse mesoporous silica nanospheres with tunable pore structure.* J. Am. Chem. Soc. 2013;135(7):2427-30.

Zhang X et al., *Biofunctionalized polymer-lipid supported mesoporous silica nanoparticles for release of chemotherapeutics in multidrug resistant cancer cells.* Biomaterials 2014;35(11):3650-65.

\* cited by examiner

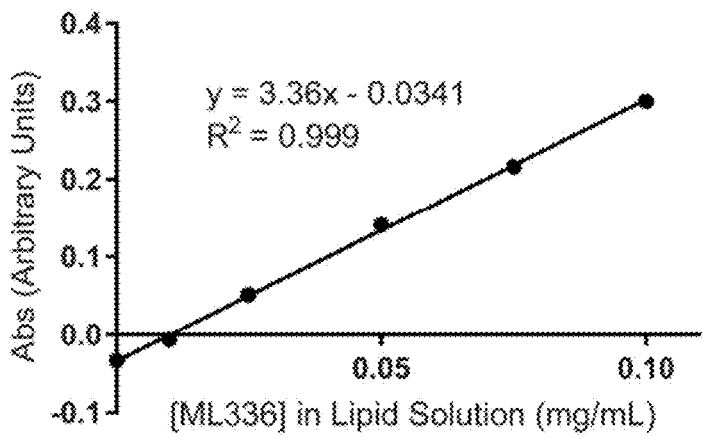
FIG. 4B
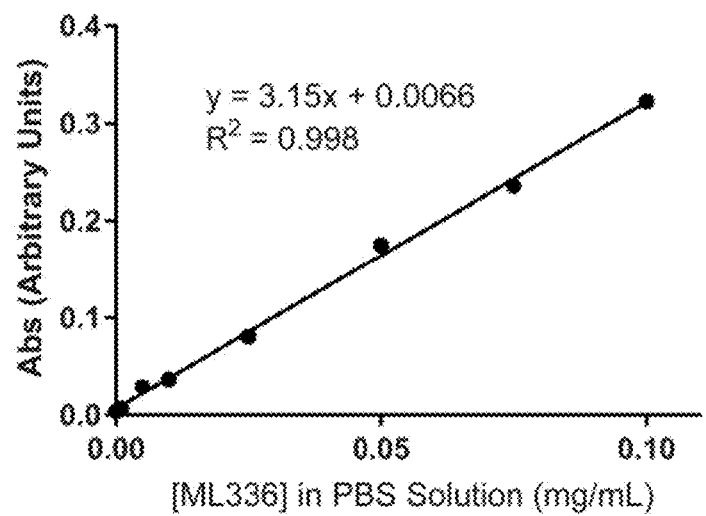
FIG. 4C
| | Mass ML336 (ug)/mg LC-MSN in: | | | Total Loaded mass ML336 loaded (ug) = 100 ug - (A+B+C) |
|---|---|---|---|---|
| | A: Supernatant after combination with lipids | B: Supernatant after PBS Wash 1 | C: Supernatant after PBS Wash 2 | |
| Sample 1 | 70.57 | 5.51 | 3.29 | 20.64 |
| Sample 2 | 69.08 | 7.73 | 4.56 | 18.64 |
| Sample 3 | 72.36 | 8.04 | 2.34 | 17.26 |
| Sample 4 | 72.65 | 8.04 | 2.97 | 16.33 |
| Sample 5 | 69.98 | 5.82 | 2.97 | 21.23 |
| Sample 6 | 63.72 | 7.09 | 3.29 | 25.90 |
Average: 20.00
Stdev: 3.45
FIG. 4D

LIPID-COATED PARTICLES FOR TREATING VIRAL INFECTIONS

CROSS-REFERENCE TO RELATED APPLICATION

This application claims the benefit of U.S. Provisional Application No. 62/689,037, filed Jun. 22, 2018, which is hereby incorporated by reference in its entirety.

REFERENCE TO A SEQUENCE LISTING APPENDIX

A sequence listing appendix including an ASCII formatted file accompanies this application. The appendix includes a file named "SD14659_ST25.txt," created on Oct. 7, 2019 (size of 12.7 kilobytes), which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to lipid-coated particles for treating viral infections, including viral encephalitis infections. In particular, an antiviral compound can be disposed within the lipid-coated particle, thereby providing an antiviral carrier. Methods of making and using such carriers are described herein.

BACKGROUND OF THE INVENTION

Promising therapeutics can often provide beneficial in vitro characteristics, yet fail during in vivo investigations. Various difficulties can arise, including adverse effects at therapeutic doses, limited bioavailability, and chemical instability. Accordingly, there is need for additional methodologies to improve delivery of such therapeutics to the desired site of action.

SUMMARY OF THE INVENTION

The present invention relates to the use of a lipid-coated particle to improve the solubility and/or stability of a drug (e.g., an antiviral drug). As described herein, in one instance, lipid-coated mesoporous silica nanoparticles (LC-MSNs) were employed as delivery vehicles for antivirals with known solubility and stability issues. Without wishing to be limited by mechanism, the large surface area of the MSN core likely promotes loading of a hydrophobic or lipophilic drug, while the liposome coating could enable enhanced circulation time and biocompatibility, thereby providing an ideal carrier for antiviral ML336 drug delivery. Provides are determinations regarding colloidal stability; in vitro viral inhibition in a dose-dependent manner, as compared to untreated controls; and in vivo studies related to toxicity and efficacy in reducing brain viral titer of a virus (e.g., Venezuelan equine encephalitis virus (VEEV) TC-83 in mice). Overall, these results highlight the utility of LC-MSNs as drug delivery vehicles to treat viral infections.

In a first aspect, the present invention features a method of increasing a stability and/or a solubility of a compound within an aqueous solution. In some embodiments, the method includes: incubating the compound with a core comprising a plurality of pores, thereby providing a loaded core; and coating the loaded core with a lipid layer, thereby provided a lipid-coated particle, wherein the stability and/or the solubility of the lipid-coated particle within the aqueous solution is greater than the stability and/or the solubility of the compound within the aqueous solution.

In some embodiments, the compound has an aqueous solubility of from about 20 µg/mL to about 150 µg/mL in phosphate-buffered saline at a pH of 7.4 and/or a stability of about 80% or less of a remaining amount of the compound after incubating in plasma for about 3 hours.

In a second aspect, the present invention features a method of treating a viral infection. In some embodiments, the method includes: administering an effective amount of a lipid-coated particle to a subject. In other embodiments, the lipid-coated particle includes a porous core, a lipid layer, and an antiviral compound disposed within at least one pore of the porous core. In yet other embodiments, a concentration of the effective amount of the antiviral compound within the lipid-coated particle is less than a concentration of the effective amount of the antiviral compound alone.

In some embodiments, the viral infection is an alphavirus infection. In other embodiments, the viral infection is an encephalitis infection.

In a third aspect, the present invention features a method of treating viral encephalitis. In some embodiments, the method includes: administering an effective amount of a lipid-coated particle to a subject. In some embodiments, the lipid-coated particle includes a porous core and an antiviral compound disposed within at least one pore of the porous core, where the effective amount of the lipid-coated particle provides a reduction of brain viral load, as compared to administration of the antiviral compound alone.

In a fourth aspect, the present invention features a method of reducing brain viral load within a subject. In some embodiments, the method includes: administering an effective amount of a lipid-coated particle to the subject. In particular embodiments, the lipid-coated particle comprises a porous core and an antiviral compound disposed within at least one pore of the porous core.

In a fifth aspect, the present invention features an antiviral carrier including: a porous core comprising a plurality of pores; an antiviral compound disposed in at least one pore; and a lipid layer disposed around the porous core. In some embodiments, the antiviral compound has an aqueous solubility of from about 20 µg/mL to about 150 µg/mL in phosphate-buffered saline at a pH of 7.4 and/or a stability of about 80% or less of a remaining amount of the compound after incubating in plasma for about 3 hours.

In some embodiments, the antiviral compound is present in an amount of from about 10 µg/mg to 50 µg/mg (µg of the compound per mg of the carrier).

In some embodiments, the antiviral compound has a release rate of from about 3 µg/mg to about 20 µg/mg (µg of the compound per mg of the carrier) over a period of about 24 hours in vitro.

In some embodiments, the lipid layer includes a zwitterionic lipid, a cholesterol or a derivative thereof, and a pegylated lipid.

In some embodiments, the antiviral compound has an aqueous solubility of from about 20 µg/mL to about 150 µg/mL in phosphate-buffered saline at a pH of 7.4. In other embodiments, the antiviral compound has a stability of about 80% or less of a remaining amount of the compound after incubating in plasma for about 3 hours.

In some embodiments, the antiviral compound has an EC$_{50}$ value of from about 0.01 µM to about 1 µM as determined in a cellular assay.

In some embodiments, the antiviral compound has an EC$_{90}$ value of from about 100 nM to about 300 nM as determined in a cellular assay. In other embodiments, the antiviral compound is hydrophobic or lipophilic.

In a sixth aspect, the present invention features a formulation including an antiviral (e.g., any described herein) and an optional pharmaceutically acceptable excipient.

In any embodiment herein, the lipid-coated particle includes a porous core and an antiviral compound disposed within at least one pore of the porous core.

In any embodiment herein, the lipid layer includes a zwitterionic lipid, a cholesterol or a derivative thereof, and a pegylated lipid.

In any embodiment herein, the compound or the antiviral compound has an aqueous solubility of from about 20 µg/mL to about 150 µg/mL in phosphate-buffered saline at a pH of 7.4. In other embodiments, the compound or the antiviral compound has a stability of about 80% or less of a remaining amount of the compound after incubating in plasma for about 3 hours.

In any embodiment herein, the compound or the antiviral compound has an EC$_{50}$ value of from about 0.01 µM to about 1 µM as determined in a cellular assay. In other embodiments, the compound or the antiviral compound has an EC$_{90}$ value of from about 100 nM to about 300 nM as determined in a cellular assay.

In any embodiment herein, the compound or the antiviral compound is hydrophobic or lipophilic.

In any embodiment herein, the compound or the antiviral compound has a structure of formula (I) or (II) or (III):

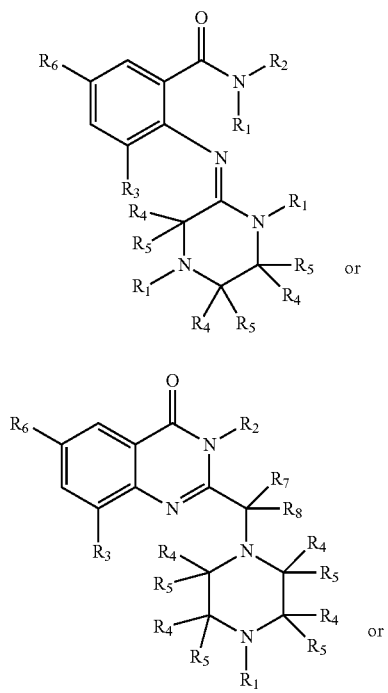

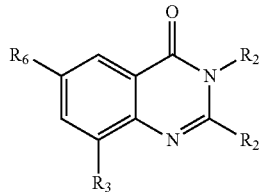

or a salt thereof, wherein: each R$_2$ is, independently, optionally substituted aryl (e.g., C$_{4-18}$ aryl, including optionally substituted phenyl, such as a substituted p-phenyl), optionally substituted heterocyclyl, optionally substituted alkaryl (e.g., C$_{1-6}$ alk-C$_{4-18}$ aryl, including optionally substituted benzyl), or optionally substituted alkheterocyclyl; each R$_1$, R$_3$, R$_4$, R$_5$, R$_6$, R$_7$, and R$_8$ is, independently, H, optionally substituted alkyl (e.g., C$_{1-6}$ alkyl), halo, nitro, nitroso, amino, azido, carboxyl, cyano, hydroxyl, optionally substituted hydroxyalkyl, optionally substituted haloalkyl, optionally substituted perfluoroalkyl, or optionally substituted cycloalkyl, or in which R$_4$ and R$_5$, taken together, or R$_7$ and R$_8$, taken together, form an optionally substituted spirocyclyl.

In some embodiments, each R$_4$, R$_5$, R$_7$, and R$_8$ is, independently, H, optionally substituted alkyl, halo, nitro, amino, azido, cyano, hydroxyl, optionally substituted hydroxyalkyl, optionally substituted haloalkyl, optionally substituted perfluoroalkyl, or optionally substituted cycloalkyl, or in which R$_4$ and R$_5$, taken together, or R$_7$ and R$_8$, taken together, form an optionally substituted spirocyclyl; and each R$_3$ and R$_6$ is, independently, H, optionally substituted alkyl, halo, nitro, nitroso, amino, azido, carboxyl, cyano, hydroxyl, optionally substituted hydroxyalkyl, optionally substituted haloalkyl, optionally substituted perfluoroalkyl, or optionally substituted cycloalkyl.

Definitions

As used herein, the term "about" means+/−10% of any recited value. As used herein, this term modifies any recited value, range of values, or endpoints of one or more ranges.

By "alkaryl" is meant an aryl group, as defined herein, attached to the parent molecular group through an alkylene group, as defined herein. Similarly, by the term "alkheteroaryl" is meant a heteroaryl group, as defined herein, attached to the parent molecular group through an alkylene group. Other groups preceded by the prefix "alk-" are defined in the same manner. The alkaryl group can be substituted or unsubstituted. For example, the alkaryl group can be substituted with one or more substitution groups, as described herein for alkyl and/or aryl. Exemplary unsubstituted alkaryl groups are of from 7 to 16 carbons (C$_{7-16}$ alkaryl), as well as those having an alkylene group with 1 to 6 carbons and an aryl group with 4 to 18 carbons (i.e., C$_{1-6}$ alk-C$_{4-18}$ aryl).

By "alkheterocyclyl" represents a heterocyclyl group, as defined herein, attached to the parent molecular group through an alkylene group, as defined herein. Exemplary unsubstituted alkheterocyclyl groups are of from 2 to 14 carbons.

By "alkyl" and the prefix "alk" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., C$_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{1-6}$ alkoxy (e.g., —OAk, in which Ak is an alkyl group, as defined herein); (2) $C_{1-6}$ alkylsulfinyl (e.g., —S(O)Ak, in which Ak is an alkyl group, as defined herein); (3) $C_{1-6}$ alkylsulfonyl (e.g., —SO$_2$Ak, in which Ak is an alkyl group, as defined herein); (4) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (5) aryl; (6) arylalkoxy (e.g., —OA$^L$Ar, in which A$^L$ is an alkylene group and Ar is an aryl group, as defined herein); (7) aryloyl (e.g., —C(O)Ar, in which Ar is an aryl group, as defined herein); (8) azido (e.g., an —N$_3$ group); (9) cyano (e.g., a —CN group); (10) carboxyaldehyde (e.g., a —C(O)H group); (11) $C_{3-8}$ cycloalkyl; (12) halo; (13) heterocyclyl (e.g., a 5-, 6- or 7-membered ring, unless otherwise specified, containing one, two, three, or four non-carbon heteroatoms (e.g., independently selected from the group consisting of nitrogen, oxygen, phosphorous, sulfur, or halo)); (14) heterocyclyloxy (e.g., —OHet, in which Het is a heterocyclyl group); (15) heterocyclyloyl (e.g., —C(O)Het, in which Het is a heterocyclyl group); (16) hydroxyl (e.g., a —OH group); (17)N-protected amino; (18) nitro (e.g., an —NO$_2$ group); (19) oxo (e.g., an =O group); (20) $C_{3-8}$ spirocyclyl (e.g., an alkylene diradical, both ends of which are bonded to the same carbon atom of the parent group to form a spirocyclyl group); (21) $C_{1-6}$ thioalkoxy (e.g., —SAk, in which Ak is an alkyl group, as defined herein); (22) thiol (e.g., an —SH group); (23) —CO$_2$R$^A$, where R$^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (24) —C(O)NR$^E$R$^G$, where each of R$^B$ and R$^G$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (25) —SO$_2$R$^D$, where R$^D$ is selected from the group consisting of (a) $C_{1-6}$ alkyl, (b) $C_{4-18}$ aryl, and (c) $C_{1-6}$ alk-$C_{4-18}$ aryl; (26) —SO$_2$NR$^E$R$^F$, where each of R$^E$ and R$^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; and (27) —NR$^G$R$^H$, where each of R$^G$ and R$^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group. The alkyl group can be a primary, secondary, or tertiary alkyl group substituted with one or more substituents (e.g., one or more halo or alkoxy). In some embodiments, the unsubstituted alkyl group is a $C_{1-3}$, $C_{1-6}$, $C_{1-12}$, $C_{1-16}$, $C_{1-18}$, $C_{1-20}$, or $C_{1-24}$ alkyl group.

By "alkylene" is meant a multivalent (e.g., bivalent, trivalent, tetravalent, etc.) form of an alkyl group, as described herein. Exemplary alkylene groups include methylene, ethylene, propylene, butylene, etc. In some embodiments, the alkylene group is a $C_{1-3}$, $C_{1-6}$, $C_{1-12}$, $C_{1-16}$, $C_{1-18}$, $C_{1-20}$, $C_{1-24}$, $C_{2-3}$, $C_{2-6}$, $C_{2-12}$, $C_{2-16}$, $C_{2-18}$, $C_{2-20}$, or $C_{2-24}$ alkylene group. The alkylene group can be branched or unbranched. The alkylene group can also be substituted or unsubstituted. For example, the alkylene group can be substituted with one or more substitution groups, as described herein for alkyl.

By "amino" is meant —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group, as defined herein.

By "aryl" is meant a group that contains any carbon-based aromatic group including, but not limited to, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one, two, three, four, or five substituents independently selected from the group consisting of: (1) $C_{1-6}$ alkanoyl (e.g., —C(O)Ak, in which Ak is an alkyl group, as defined herein); (2) $C_{1-6}$ alkyl; (3) $C_{1-6}$ alkoxy (e.g., —OAk, in which Ak is an alkyl group, as defined herein); (4) $C_{1-6}$ alkoxy-$C_{1-6}$ alkyl (e.g., an alkyl group, which is substituted with an alkoxy group —OAk, in which Ak is an alkyl group, as defined herein); (5) $C_{1-6}$ alkylsulfinyl (e.g., —S(O)Ak, in which Ak is an alkyl group, as defined herein); (6) $C_{1-6}$ alkylsulfinyl-$C_{1-6}$ alkyl (e.g., an alkyl group, which is substituted by an alkylsulfinyl group —S(O)Ak, in which Ak is an alkyl group, as defined herein); (7) $C_{1-6}$ alkylsulfonyl (e.g., —SO$_2$Ak, in which Ak is an alkyl group, as defined herein); (8) $C_{1-6}$ alkylsulfonyl-$C_{1-6}$ alkyl (e.g., an alkyl group, which is substituted by an alkylsulfonyl group —SO$_2$Ak, in which Ak is an alkyl group, as defined herein); (9) aryl; (10) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (11) $C_{1-6}$ aminoalkyl (e.g., meant an alkyl group, as defined herein, substituted by an amino group); (12) heteroaryl; (13) $C_{1-6}$ alk-$C_{4-18}$ aryl (e.g., -A$^L$Ar, in which A$^L$ is an alkylene group and Ar is an aryl group, as defined herein); (14) aryloyl (e.g., —C(O)Ar, in which Ar is an aryl group, as defined herein); (15) azido (e.g., an —N$_3$ group); (16) cyano (e.g., a —CN group); (17) $C_{1-6}$ azidoalkyl (e.g., a —N$_3$ azido group attached to the parent molecular group through an alkyl group, as defined herein); (18) carboxyaldehyde (e.g., a —C(O)H group); (19) carboxyaldehyde-$C_{1-6}$ alkyl (e.g., -A$^L$C(O)H, in which A$^L$ is an alkylene group, as defined herein); (20) $C_{3-8}$ cycloalkyl; (21) $C_{1-6}$ alk-$C_{3-8}$ cycloalkyl (e.g., -A$^L$Cy, in which A$^L$ is an alkylene group and Cy is a cycloalkyl group, as defined herein); (22) halo (e.g., F, C$_1$, Br, or I); (23) $C_{1-6}$ haloalkyl (e.g., an alkyl group, as defined herein, substituted with one or more halo); (24) heterocyclyl; (25) heterocyclyloxy (e.g., —OHet, in which Het is a heterocyclyl group); (26) heterocyclyloyl (e.g., —C(O)Het, in which Het is a heterocyclyl group); (16) hydroxyl (e.g., a —OH group); (27) hydroxyl (e.g., a —OH group); (28) $C_{1-6}$ hydroxyalkyl (e.g., an alkyl group, as defined herein, substituted by one to three hydroxyl groups, with the proviso that no more than one hydroxyl group may be attached to a single carbon atom of the alkyl group); (29) nitro (e.g., an —NO$_2$ group); (30) $C_{1-6}$ nitroalkyl (e.g., an alkyl group, as defined herein, substituted by one to three nitro groups); (31)N-protected amino; (32)N-protected amino-$C_{1-6}$ alkyl; (33) oxo (e.g., an =O group); (34) $C_{1-6}$ thioalkoxy (e.g., —SAk, in which Ak is an alkyl group, as defined herein); (35) thio-$C_{1-6}$ alkoxy-$C_{1-6}$ alkyl (e.g., an alkyl group, which is substituted by an thioalkoxy group SAk, in which Ak is an alkyl group, as defined herein); (36) —$(CH_2)_rCO_2R^A$, where r is an integer of from zero to four, and $R^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (37) —$(CH_2)_rCONR^BR^C$, where r is an integer of from zero to four and where each $R^B$ and $R^G$ is independently selected from the group consisting of (a) hydrogen, (b) $C_{1-6}$ alkyl, (c) $C_{4-18}$ aryl, and (d) $C_{1-6}$ alk-$C_{4-18}$ aryl; (38) —$(CH_2)_rSO_2R^D$, where r is an integer of from zero to four and where $R^H$ is selected from the group consisting of (a) $C_{1-6}$ alkyl, (b) $C_{4-18}$ aryl, and (c) $C_{1-6}$ alk-$C_{4-18}$ aryl; (39) —$(CH_2)_rSO_2NR^ER^F$, where r is an integer of from zero to four and where each of $R^E$ and $R^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (40) —$(CH_2)_rNR^GR^B$, where r is an integer of from zero to four and where each of $R^G$ and $R^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group; (41) thiol; (42) perfluoroalkyl (e.g., an alkyl group, as defined herein, having each hydrogen atom substituted with a fluorine atom); (43) perfluoroalkoxy (e.g., —ORf, in which Rf is an alkyl group, as defined herein, having each hydrogen atom substituted with a fluorine atom); (44) aryloxy (e.g., —OAr, where Ar is an optionally substituted aryl group, as described herein); (45) cycloalkoxy (e.g., —OCy, in which Cy is a cycloalkyl group, as defined herein); (46) cycloalkylalkoxy (e.g., —OA$^L$Cy, in which A$^L$ is an alkylene group and Cy is a cycloalkyl group, as defined herein); and (47) arylalkoxy (e.g., —OA$^L$Ar, in which A$^L$ is an alkylene group and Ar is an aryl group, as defined herein). In particular embodiments, an unsubstituted aryl group is a $C_{4-18}$, $C_{4-14}$, $C_{4-12}$, $C_{4-10}$, $C_{6-18}$, $C_{6-14}$, $C_{6-12}$, or $C_{6-10}$ aryl group.

By "azido" is meant an —$N_3$ group.
By "carboxyl" is meant a —$CO_2H$ group.
By "cyano" is meant a —CN group.
By "cycloalkyl" is meant a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1]heptyl and the like. The cycloalkyl group can also be substituted or unsubstituted. For example, the cycloalkyl group can be substituted with one or more groups including those described herein for alkyl.
By "halo" is meant F, Cl, Br, or I.
By "haloalkyl" is meant an alkyl group, as defined herein, substituted with one or more halo.
By "heteroalkyl" is meant an alkyl group, as defined herein, containing one, two, three, or four non-carbon heteroatoms (e.g., independently selected from the group consisting of nitrogen, oxygen, phosphorous, sulfur, or halo).
By "heteroaryl" is meant a subset of heterocyclyl groups, as defined herein, which are aromatic, i.e., they contain 4n+2 pi electrons within the mono- or multicyclic ring system.
By "heterocyclyl" is meant a 5-, 6- or 7-membered ring, unless otherwise specified, containing one, two, three, or four non-carbon heteroatoms (e.g., independently selected from the group consisting of nitrogen, oxygen, phosphorous, sulfur, or halo). The 5-membered ring has zero to two double bonds and the 6- and 7-membered rings have zero to three double bonds. The term "heterocyclyl" also includes bicyclic, tricyclic and tetracyclic groups in which any of the above heterocyclic rings is fused to one, two, or three rings independently selected from the group consisting of an aryl ring, a cyclohexane ring, a cyclohexene ring, a cyclopentane ring, a cyclopentene ring, and another monocyclic heterocyclic ring, such as indolyl, quinolyl, isoquinolyl, tetrahydroquinolyl, benzofuryl, benzothienyl and the like. Heterocyclics include thiiranyl, thietanyl, tetrahydrothienyl, thianyl, thiepanyl, aziridinyl, azetidinyl, pyrrolidinyl, piperidinyl, azepanyl, pyrrolyl, pyrrolinyl, pyrazolyl, pyrazolinyl, pyrazolidinyl, imidazolyl, imidazolinyl, imidazolidinyl, pyridyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl, and the like.

By "hydroxyl" is meant —OH.
By "hydroxyalkyl" is meant an alkyl group, as defined herein, substituted by one to three hydroxyl groups, with the proviso that no more than one hydroxyl group may be attached to a single carbon atom of the alkyl group and is exemplified by hydroxymethyl, dihydroxypropyl, and the like.
By "nitro" is meant an —$NO_2$ group.
By "nitroalkyl" is meant an alkyl group, as defined herein, substituted by one to three nitro groups.
By "nitroso" is meant an —NO group.
By "perfluoroalkyl" is meant an alkyl group, as defined herein, having each hydrogen atom substituted with a fluorine atom. Exemplary perfluoroalkyl groups include trifluoromethyl, pentafluoroethyl, etc.
By "protecting group" is meant any group intended to protect a reactive group against undesirable synthetic reactions. Commonly used protecting groups are disclosed in "Greene's Protective Groups in Organic Synthesis," John Wiley & Sons, New York, 2007 (4th ed., eds. P.G.M. Wuts and T.W. Greene), which is incorporated herein by reference. O-protecting groups include an optionally substituted alkyl group (e.g., forming an ether with reactive group O), such as methyl, methoxymethyl, methylthiomethyl, benzoyloxymethyl, t-butoxymethyl, etc.; an optionally substituted alkanoyl group (e.g., forming an ester with the reactive group O), such as formyl, acetyl, chloroacetyl, fluoroacetyl (e.g., perfluoroacetyl), methoxyacetyl, pivaloyl, t-butylacetyl, phenoxyacetyl, etc.; an optionally substituted aryloyl group (e.g., forming an ester with the reactive group O), such as —C(O)—Ar, including benzoyl; an optionally substituted alkylsulfonyl group (e.g., forming an alkylsulfonate with reactive group O), such as —$SO_2$—$R^{s1}$, where $R^{s1}$ is optionally substituted $C_{1-12}$ alkyl, such as mesyl or benzylsulfonyl; an optionally substituted arylsulfonyl group (e.g., forming an arylsulfonate with reactive group O), such as $SO_2$—$R^{S4}$, where $R^{S4}$ is optionally substituted $C_{4-18}$ aryl, such as tosyl or phenylsulfonyl; an optionally substituted alkoxycarbonyl or aryloxycarbonyl group (e.g., forming a carbonate with reactive group O), such as —C(O)—$OR^{T1}$, where $R^{T1}$ is optionally substituted $C_{1-12}$ alkyl or optionally substituted $C_{4-18}$ aryl, such as methoxycarbonyl, methoxymethylcarbonyl, t-butyloxycarbonyl (Boc), or benzyloxycarbonyl (Cbz); or an optionally substituted silyl group (e.g., forming a silyl ether with reactive group O), such as —Si—(R$^{72}$)$_3$, where each R$^{72}$ is, independently, optionally substituted C$_{1-12}$ alkyl or optionally substituted C$_{4-18}$ aryl, such as trimethylsilyl, t-butyldimethylsilyl, or t-butyldiphenylsilyl. N-protecting groups include, e.g., formyl, acetyl, benzoyl, pivaloyl, t-butylacetyl, alanyl, phenylsulfonyl, benzyl, Boc, and Cbz. Such protecting groups can employ any useful agent to cleave the protecting group, thereby restoring the reactivity of the unprotected reactive group.

By "salt" is meant an ionic form of a compound or structure (e.g., any formulas, compounds, or compositions described herein), which includes a cation or anion compound to form an electrically neutral compound or structure. Salts (e.g., simple salts having binary compounds, double salts, triple salts, etc.) are well known in the art. For example, salts are described in Berge S M et al., "Pharmaceutical salts," J. Pharm. Sci. 1977 January; 66(1):1-19; International Union of Pure and Applied Chemistry, "Nomenclature of Inorganic Chemistry," Butterworth & Co. (Publishers) Ltd., London, England, 1971 (2nd ed.); and in "Handbook of Pharmaceutical Salts: Properties, Selection, and Use," Wiley-VCH, April 2011 (2nd rev. ed., eds. P.H. Stahl and C.G. Wermuth). The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine.

By "spirocyclyl" is meant an alkylene diradical, both ends of which are bonded to the same carbon atom of the parent group to form a spirocyclyl group and also a heteroalkylene diradical, both ends of which are bonded to the same atom.

By "micro" is meant having at least one dimension that is less than 1 mm. For instance, a microstructure (e.g., any structure described herein, such as a microparticle) can have a length, width, height, cross-sectional dimension, circumference, radius (e.g., external or internal radius), or diameter that is less than 1 mm.

By "nano" is meant having at least one dimension that is less than 1 For instance, a nanostructure (e.g., any structure described herein, such as a nanoparticle) can have a length, width, height, cross-sectional dimension, circumference, radius (e.g., external or internal radius), or diameter that is less than 1 µm.

The phrase "effective average particle size" as used herein to describe a multiparticulate (e.g., a porous nanoparticulate) means that at least 50% of the particles therein are of a specified size. Accordingly, "effective average particle size of less than about 2,000 nm in diameter" means that at least 50% of the particles therein are less than about 2,000 nm in diameter. In certain embodiments, nanoparticulates have an effective average particle size of less than about 2,000 nm (i.e., 2 microns), less than about 1,900 nm, less than about 1,800 nm, less than about 1,700 nm, less than about 1,600 nm, less than about 1,500 nm, less than about 1,400 nm, less than about 1,300 nm, less than about 1,200 nm, less than about 1,100 nm, less than about 1,000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods. In certain aspects of the present invention, the particles are monodisperse and generally no greater than about 50 nm in average diameter, often less than about 30 nm in average diameter, as otherwise described herein. The term "D$_{50}$" refers to the particle size below which 50% of the particles in a multiparticulate fall. Similarly, the term "D$_{90}$" refers to the particle size below which 90% of the particles in a multiparticulate fall.

The term "monodisperse" is used as a standard definition established by the National Institute of Standards and Technology (NIST) (Particle Size Characterization, Special Publication 960-1, January 2001) to describe a distribution of particle size within a population of particles, in this case nanoparticles, which particle distribution may be considered monodisperse if at least 90% of the distribution lies within 5% of the median size. See, e.g., Takeuchi S et al., Adv. Mater. 2005; 17(8):1067-72.

The term "lipid" is used to describe the components which are used to form lipid mono-, bi-, or multilayers on the surface of the particles (e.g., a core of the particle), that are used in the present invention (e.g., as lipid-coated particles) and may include a PEGylated lipid. Various embodiments provide nanostructures, that are constructed from nanoparticles, which support one or more lipid layers (e.g., bilayer(s) or multilayer(s)). In embodiments according to the present invention, the nanostructures preferably include, for example, a core-shell structure including a porous particle core surrounded by a shell of one or more lipid bilayer(s). In one non-limiting embodiment, the nanostructure (e.g., a porous silica or alum nanostructure) supports the lipid bilayer membrane structure.

The terms "targeting ligand" and "targeting active species" are used to describe a compound or moiety (e.g., an antigen), which is complexed or covalently bonded to the surface of particle according to the present invention (e.g., either directly on an outer surface of a delivery platform, on an outer lipid layer, or on a supported lipid layer). The targeting ligand, in turn, binds to a moiety on the surface of a cell to be targeted so that the lipid-coated particles may bind to the surface of the targeted cell, enter the cell or an organelle thereof, and/or deposit their contents into the cell. The targeting active species for use in the present invention is preferably a targeting peptide (e.g., a cell penetration peptide, a fusogenic peptide, or an endosomolytic peptide, as otherwise described herein), a polypeptide including an antibody or antibody fragment, an aptamer, or a carbohydrate, among other species that bind to a targeted cell.

By an "effective amount" or a "sufficient amount" of an agent (e.g., a lipid-coated particle, an antiviral compound, a compound, or an antiviral carrier), as used herein, is that amount sufficient to effect beneficial or desired results, such as clinical results, and, as such, an "effective amount" depends upon the context in which it is being applied. For example, in the context of administering an agent that employs an antiviral compound is, for example, an amount sufficient to achieve decreased viral titer of a virus and/or to treat an infection, as compared to the response obtained without administration of the agent. In another example, in the context of administering an antiviral carrier that employs an antiviral compound is, for example, an amount sufficient to achieve decreased viral titer of a virus and/or to treat an infection, as compared to the response obtained without administration of the antiviral carrier. In yet another example, in the context of administering an antiviral carrier that employs an amount of the antiviral compound is, for example, an amount sufficient to achieve decreased viral titer of a virus and/or to treat an infection, as compared to the response obtained with administration of the amount of the antiviral compound without the antiviral carrier. Thus, an effective amount of an antiviral carrier including an antiviral compound can be compared to any useful control (e.g., an effect determined upon administration of an effective amount of the antiviral compound when used alone, an effect determined upon administration of a buffer, or an effect determined without administration of the antiviral carrier).

By "subject" is meant a human or non-human animal (e.g., a mammal).

By "treating" a disease, disorder, or condition in a subject is meant reducing at least one symptom of the disease, disorder, or condition by administrating a therapeutic agent to the subject. By "treating prophylactically" a disease, disorder, or condition in a subject is meant reducing the frequency of occurrence of or reducing the severity of a disease, disorder or condition by administering a therapeutic agent to the subject prior to the onset of disease symptoms. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable.

By "salt" is meant an ionic form of a compound or structure (e.g., any formulas, compounds, or compositions described herein), which includes a cation or anion compound to form an electrically neutral compound or structure. Salts are well known in the art. For example, non-toxic salts are described in Berge S M et al., "Pharmaceutical salts," *J. Pharm. Sci.* 1977 January; 66(1):1-19; and in "Handbook of Pharmaceutical Salts: Properties, Selection, and Use," Wiley-VCH, April 2011 (2nd rev. ed., eds. P.H. Stahl and C.G. Wermuth). The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine. Exemplary salts include pharmaceutically acceptable salts.

By "pharmaceutically acceptable salt" is meant a salt that is, within the scope of sound medical judgment, suitable for use in contact with the tissues of humans and animals without undue toxicity, irritation, allergic response and the like and are commensurate with a reasonable benefit/risk ratio.

By "pharmaceutically acceptable excipient" is meant any ingredient other than a compound or structure (e.g., any formulas, compounds, or compositions described herein) and having the properties of being nontoxic and non-inflammatory in a subject. Exemplary, non-limiting excipients include adjuvants, antiadherents, antioxidants, binders, carriers, coatings, compression aids, diluents, disintegrants, dispersing agents, dyes (colors), emollients, emulsifiers, fillers (diluents), film formers or coatings, flavors, fragrances, glidants (flow enhancers), isotonic carriers, lubricants, preservatives, printing inks, solvents, sorbents, stabilizers, suspensing or dispersing agents, surfactants, sweeteners, waters of hydration, or wetting agents. Any of the excipients can be selected from those approved, for example, by the United States Food and Drug Administration or other governmental agency as being acceptable for use in humans or domestic animals. Exemplary excipients include, but are not limited to alcohol, butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, glycerol, hydroxypropyl cellulose, hydroxypropyl methylcellulose, lactated Ringer's solution, lactose, magnesium stearate, maltitol, maltose, mannitol, methionine, methylcellulose, methyl paraben, microcrystalline cellulose, polyethylene glycol, polyol, polyvinyl pyrrolidone, povidone, pregelatinized starch, propyl paraben, retinyl palmitate, Ringer's solution, shellac, silicon dioxide, sodium carboxymethyl cellulose, sodium chloride injection, sodium citrate, sodium starch glycolate, sorbitol, starch (corn), stearic acid, stearic acid, sucrose, talc, titanium dioxide, vegetable oil, vitamin A, vitamin E, vitamin C, water, and xylitol.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

FIG. 4A-4F shows (A) DLS measurements of ML336 loaded MSNs and loaded LC-MSNs over the course of a week. ML336 loading and release was determined by comparing sample absorbance values at 320 nm to a standard curve in (B) a lipid solution or (C) a PBS solution. (D) ML336 loading was calculated using the following formula: Total mass loaded=Initial mass of ML336 added−[(mass of ML336 in the supernatant after combination with the lipids)+(mass of ML336 in the supernatant of PBS wash 1)+(mass of ML336 in the supernatant of PBS wash 2)]. Also provided are (E) cumulative and (F) percent release (normalized to total ML336 loaded) of ML336 from LC-MSNs in PBS pH 7, PBS pH 5, and methanol (MeOH). Data represent mean±standard deviation, *=significantly different MeOH group at 18 hours, n=5.

FIG. 5A-5D shows that ML336 inhibits TC-83 and VEEV (ZPC738 virulent strain) in a dose-dependent manner. Provided are graphs showing (A) TC-83 viral inhibition in HeLa cells at 24 and 48 hours with increasing concentrations of ML336 (n=3); (B) IC-50 of ML336 is 163 nm for HeLa cells at 24 hours of TC-83 infection; (C) VEEV viral inhibition in HeLa cells at 24 hours with increasing concentrations of ML336; and (D) IC-50 of ML336 is 15 nm for HeLa cells at 24 hours of VEEV infection (n=1).

FIG. 6 shows that ML336 loaded LC-MSNs do not visibly affect cell viability. LIVE (green)/DEAD (red) staining on cells treated with ML336 loaded LC-MSNs, unloaded LC-MSNs, or nothing for 48 hours (scale bar=50 μm; n=3).

µm in (D)). *=Significantly different than no inhibition group; p<0.05; data are depicted as mean±standard deviation, n=3 technical replicates.

Figure 11A:
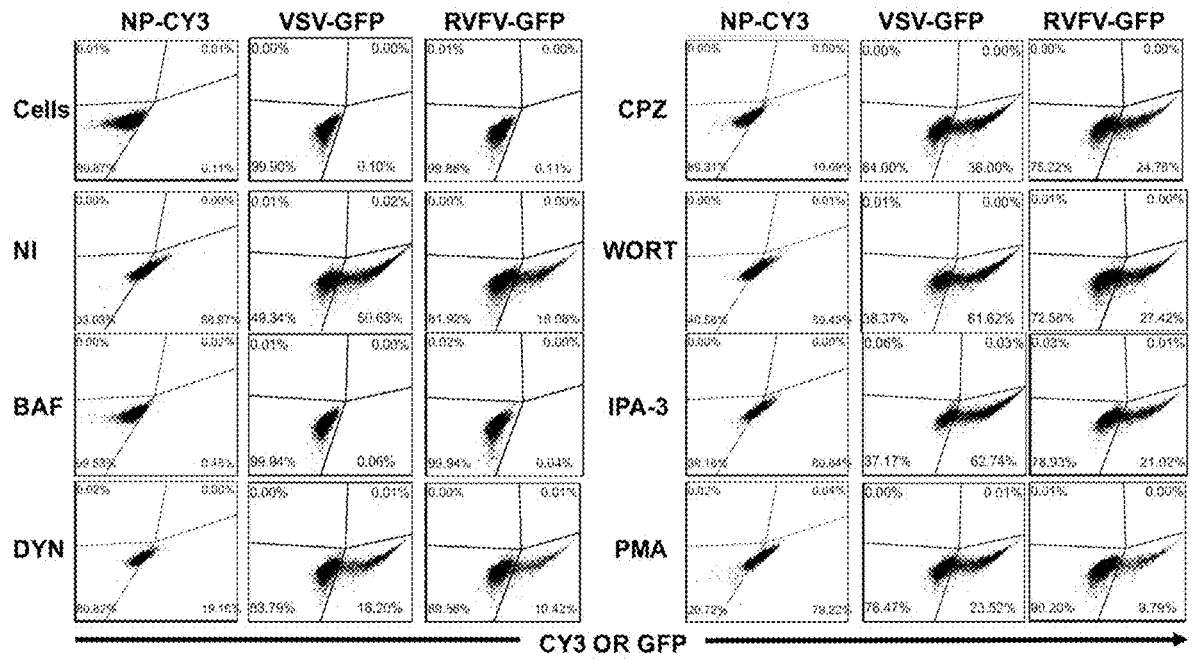
Figure 11B:
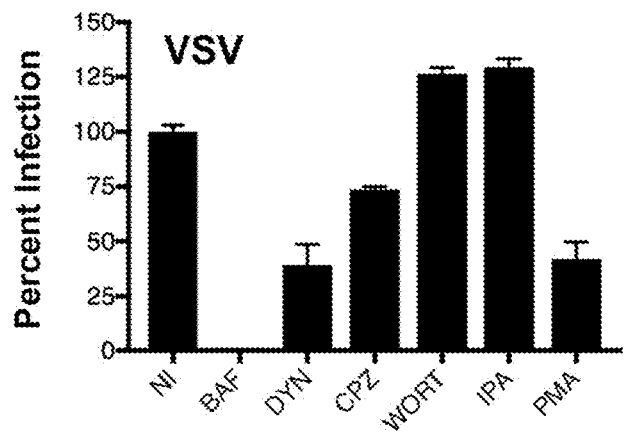
Figure 11C:
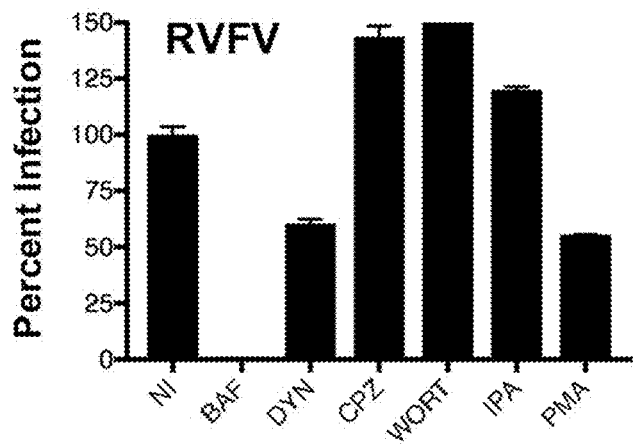

FIG. 11A-11C shows that inhibitors of clathrin-mediated endocytosis reduce both LC-MSN uptake and VSV infection, while inhibitors of caveolae-mediated endocytosis block RVFV and some VSV infection, but not LC-MSN cellular internalization. The inhibitor panel included those targeting pH dependent endocytosis (BAF), clathrin-mediated endocytosis (DYN, CPZ), macropinocytosis (WORT, IPA-3) and caveola-mediated endocytosis (PMA, DYN), while untreated cells with (NI) and without LC-MSN (cells) addition served as controls. (A) HeLa cells were incubated with endocytosis inhibitor treatments for 1 h prior and during incubation with Cy3 labeled LCMSNs (NP-Cy3), Vesicular Stomatitis virus (VSV), or Rift Valley fever virus (RVFV strain MP-12). At 16 h post nanoparticle or virus addition, cells were washed with PBS twice and prepared for flow cytometry analysis. Representative flow data are shown. No inhibitor (NI) control values were used to normalize the treatment conditions as percent infection for (B) VSV or (C) RVFV (n=2). Overall, these treatment conditions specifically distinguish between common endocytic pathways.

Figure 12A:
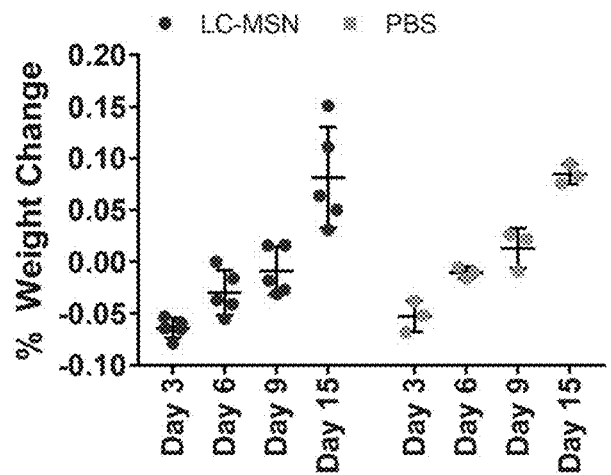
Figure 12B:
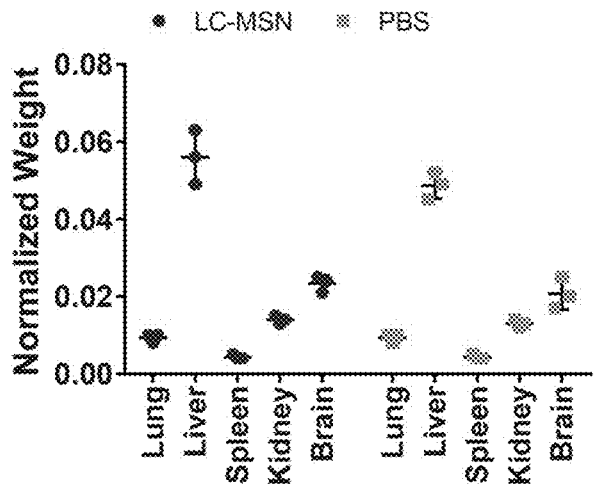
Figure 12C:
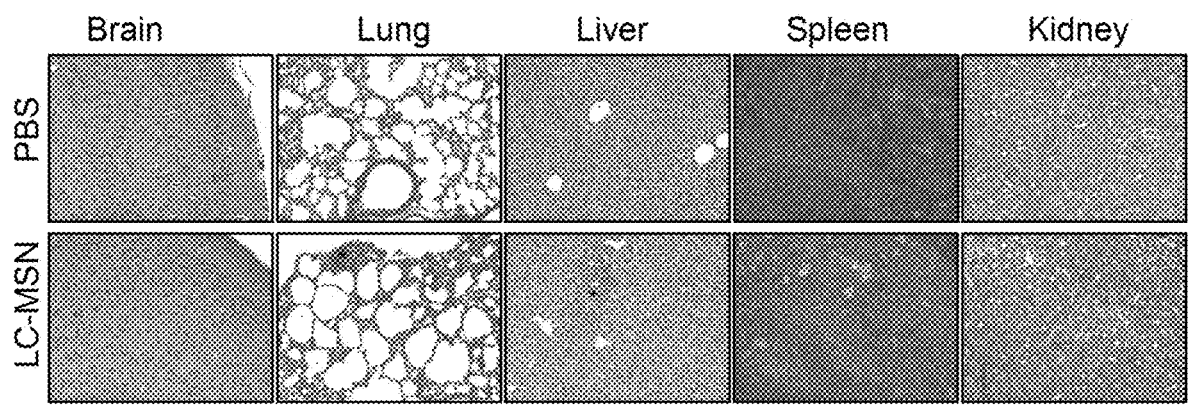

FIG. 12A-12C shows unloaded LC-MSNs do not affect animal weight in safety studies. (A) Percent weight change in animals dosed with unloaded LC-MSNs or PBS alone over the course of 15 days. (B) Normalized weights of lung, liver, spleen, kidney, and brain to total animal weight in animals dosed with unloaded LC-MSNs or PBS alone over the course of 15 days (data are depicted as mean±standard deviation). Provided are (C) histological analysis of LC-MSN dosed C₃H/HeN mice. Mouse tissues were dissected and formalin-fixed on day 15 post-treatment with a vehicle control (PBS) or LC-MSNs at 0.11 g LC-MSNs/kg/day for four days. Histological specimens were prepared through paraffin embedding and sectioning, followed by hematoxylin and eosin staining. Three animals per group were analyzed and representative images are shown. In the brain, the outer cortex is shown and displayed no obvious differences between the LC-MSN dosed and control groups. Similarly, the spleen and kidney sections exhibited normal morphology without signs of toxicity. In some samples, granulomas that contained collections of macrophages embedded in the lung and liver (indicated by asterisks) were identified and indicative of very mild symptoms.

Figure 13A:
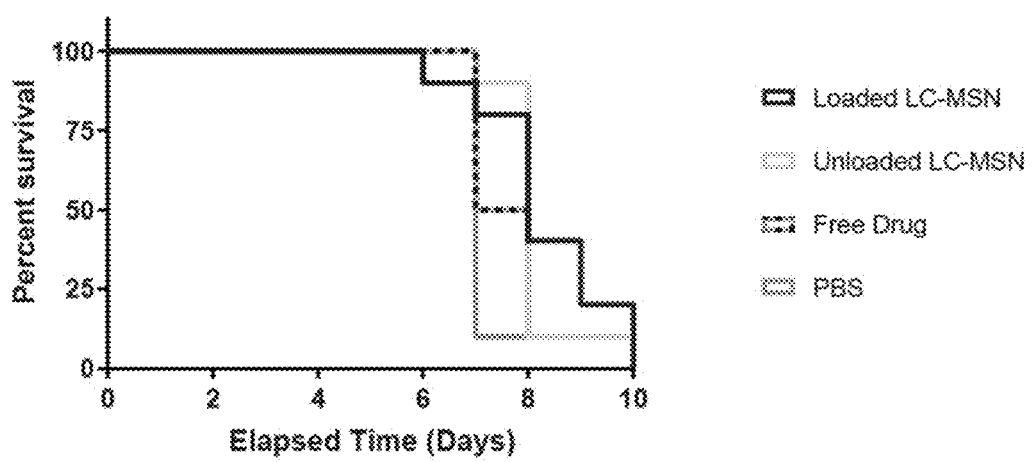
Figure 13B:
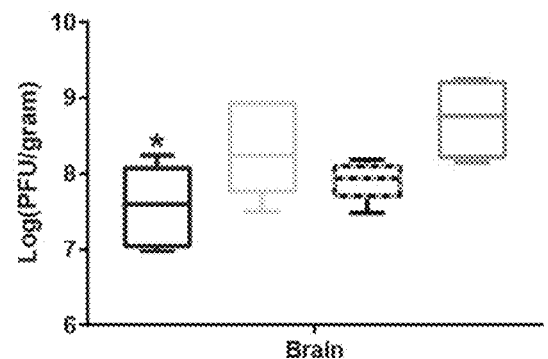
Figure 13C:
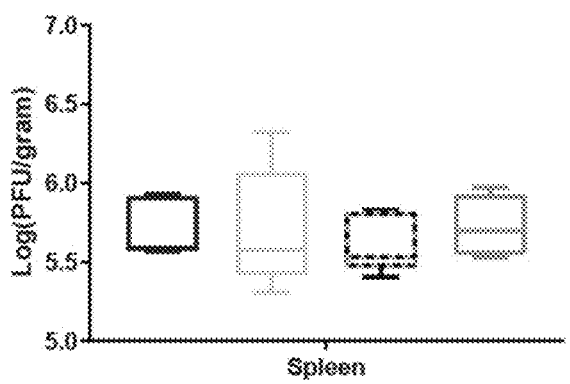

FIG. 13A-13C shows ML336 loaded LC-MSNs show reduction of viral load in vivo. Provided are (A) a survival curve for TC-83 infected animals treated with 1 mg ML336 loaded LC-MSNs twice a day for 4 days, as well as viral load in (B) brain and (C) spleen normalized to organ mass after 4 days of infection and treatment with 1.5 mg ML336 loaded LC-MSNs (*=significantly different from PBS group; p<0.05; data are depicted as mean±standard deviation).

Figure 14A:
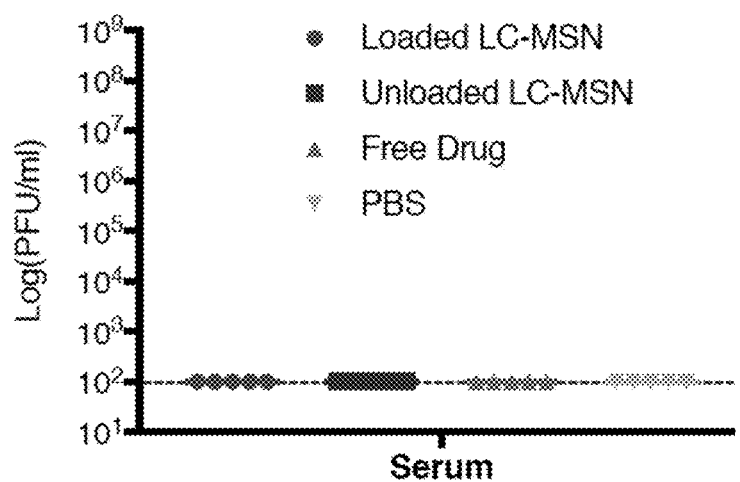
Figure 14B:
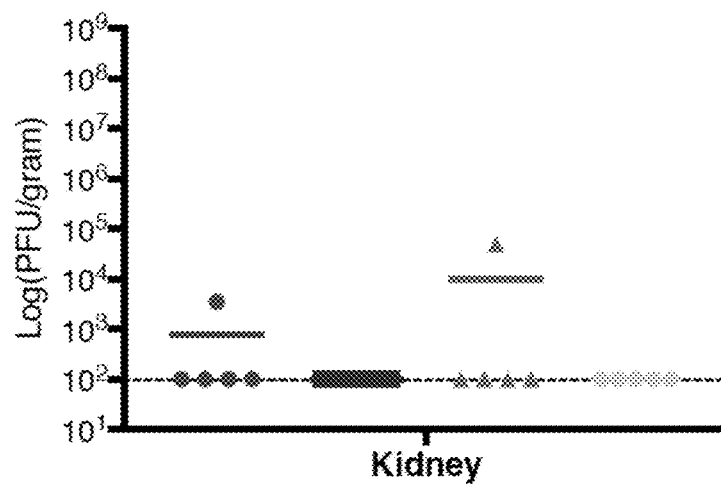
Figure 14C:
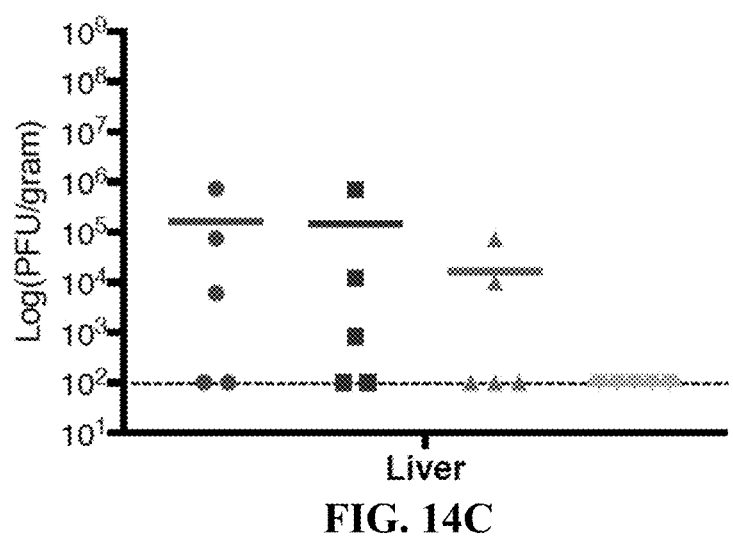

FIG. 14A-14C shows viral titer in tissues of TC-83 infected mice. Provided are the viral loads in (A) serum, (B) kidney, and (C) liver at day 4 post-infection via intranasal challenge of C₃H/HeN mice with VEEV strain TC-83 were measured by standard plaque assays normalized to volume (ml) or organs mass (gram). Viral loads from four treatment conditions are shown for ML-336 loaded LC-MSN (circle), unloaded LC-MSN (square), free ML-336 (triangle), and vehicle only (PBS) (upside down triangle) with mean from 5 samples per condition. The limit of detection (LOD) is 100PFU, and samples at or below this threshold are all listed at LOD.

DETAILED DESCRIPTION OF THE INVENTION

The present invention relates to the use of lipid-coated particles to deliver compounds having reduced stability and/or solubility. In one instance, ML336 is a small molecule inhibitor that displays antiviral activity but has poor stability and solubility characteristics. Here, we show that ML336-loaded lipid coated mesoporous silica nanoparticles (LC-MSNs) possess good colloidal stability. Such particles ML336-loaded LC-MSNs inhibited Venezuelan equine encephalitis virus (VEEV) in vitro in a dose-dependent manner, as compared to untreated controls. In vivo safety studies were conducted in C3H/HeN mice, and LC-MSNs were not toxic when at tested doses. Furthermore, ML336-loaded LC-MSNs showed significant reduction in brain viral titer in VEEV TC-83 infected mice, as compared to PBS treated controls. Overall, these results highlight the utility of LC-MSNs as drug delivery vehicles to treat VEEV infections.

Figure 1A:
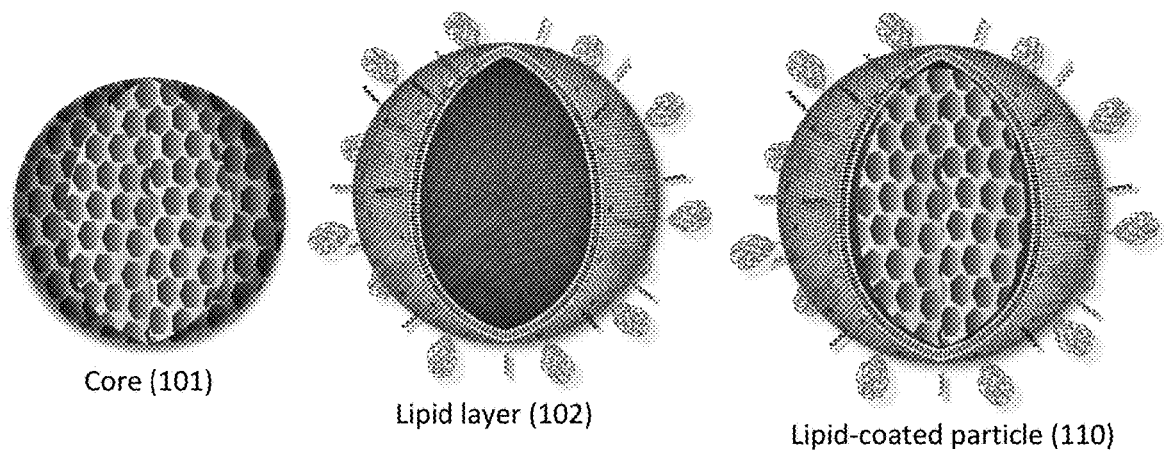
FIG. 1A-1C shows schematics of exemplary particles. Provided are (A) particular components of an exemplary lipid-coated particle 110, including an exemplary core 101 and an exemplary lipid layer 102. Also provided is (B) a schematic of another exemplary lipid-coated particle 1100, including an exemplary core 1001 and an exemplary lipid layer 1002. Provide is (C) a schematic for an exemplary lipid loaded, lipid coated-mesoporous silica nanoparticle (LC-MSN), including exemplary components.

FIG. 1A provides an exemplary lipid-coated particle 110 including an inner core 101 and an outer lipid layer 102 (e.g., a lipid bilayer, a multilamellar lipid layer, etc.) disposed around the core 101. In some non-limiting instances, the core is porous (e.g., including a plurality of cores). In other non-limiting instances, the lipid layer can include any useful lipid (e.g., a PEGylated lipid), useful component (e.g., a cholesterol), and/or useful targeting ligand (e.g., any described herein). Furthermore, the outer lipid layer can include a plurality of layers, in which each layer can be a lipid bilayer. In this manner, the layer can be multilamellar because it includes multiple lamellae (or multiple layers).

Figure 1B:
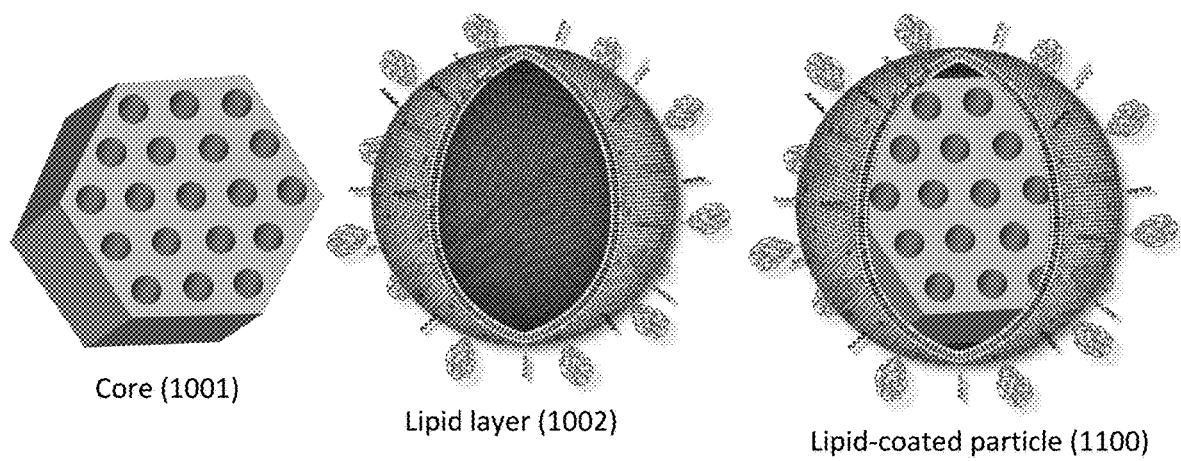

FIG. 1B provided another an exemplary lipid-coated particle 1100 including an inner core 1001 and an outer lipid layer 1002 (e.g., a lipid bilayer, a multilamellar lipid layer, etc.) disposed around the core 1001. As can be seen, the core can have any useful features or characteristics. In one embodiment, the core is a monosized (e.g., polydispersity index <0.1) particle. The core can have any useful shape, morphology, pore size, and pore distribution.

The lipid-coated particle can be characterized by any useful manner either before loading of cargo or after loading of cargo (e.g., overall charge, dimension, dispersity, etc.). Furthermore, components of the particle (e.g., the core or the lipid layer) can also be characterized by any useful manner (e.g., pore size, core size, core charge, lipid layer thickness, lipid layer charge, etc.).

Cargo (e.g., a compound) can be loaded in any useful manner. In one instance, cargo is introduced to the core, and then the loaded core is exposed to a solution containing liposomes, which results in the formation of a lipid layer disposed around the loaded core.

Compounds, Including Antiviral Compounds

The present invention can include the any useful compound (e.g., an antiviral compound). In one instance, the compound has reduced stability and/or reduced solubility, thereby would benefit from the use of a carrier (e.g., any described herein). In yet other embodiments, the compound is hydrophobic (e.g., determined in any useful manner, such as any herein).

In some embodiments, the compound has limited aqueous solubility (e.g., from about 20 µg/mL to about 150 µg/mL, such as from 20 µg/mL to 50 µg/mL, 20 µg/mL to 100 µg/mL, 20 µg/mL to 150 µg/mL, 50 µg/mL to 100 µg/mL, or 50 µg/mL to 150 µg/mL) in an aqueous solvent. Solubility can be determined in any useful manner, such as an automated kinetic solubility method at any useful temperature (e.g., of from about 20° C. to 30° C., such as about 23° C.). In one embodiment of such a solubility method, a saturated pH-buffered aqueous solution is prepared, and the concentration of the compound is determined analytically (e.g., by gas chromatography, UV absorbance, liquid chromatography mass spectrometry (LC-MS), etc.), and the obtained spectrum is compared to a control spectrum for a precipitation-free reference solution. Exemplary aqueous solvents include phosphate buffered saline (PBS, 137 mM NaCl, 2.7 mM KCl, 10 mM sodium phosphate dibasic, 2 mM potassium phosphate monobasic and a pH of 7.4) or a cell medium (e.g., a cytopathic effect (CPE) medium including high glucose DMEM (Dulbecco's Modified Eagle's Medium) with 10% fetal bovine serum and 1× penicillin streptomycin solution (Pen/Strep)).

In some embodiments, the compound has limited aqueous stability (e.g., of about 80% or less of a remaining amount of the compound after incubating in mouse plasma for about 3 hours; from about 20% to about 80% remaining amount of the compound after incubating in mouse plasma for about 3 hours; or from about 20% to 90% remaining amount of the compound after incubating at PBS, pH 7.4). Stability can be determined in any useful manner. In one instance, the compound is dissolved in a solvent (e.g., at 10 µM in PBS at pH 7.4 with 1% dimethylsulfoxide (DMSO), human plasma, or mouse plasma) and analyzed at various timepoints (e.g., numerous timepoints from 0 to 48 hours). The concentration of the compound is determined analytically (e.g., by gas chromatography, UV absorbance, LC-MS, etc.), and absolute areas under the curve can be employed at each time point to determine the relative percent of the remaining parent compound. For experiments including plasma, stability can be determined at about 37° C. with optional incubation at these temperature, centrifugation, and shaking.

In some embodiments, the compound has a computed hydrophobicity XLogP3-AA of from about 2 to about 10 (e.g., from 2 to 3, 2 to 4, 2 to 5, 2 to 6, 2 to 7, 2 to 8, 2 to 9, 3 to 4, 3 to 5, 3 to 6, 3 to 7, 3 to 8, 3 to 9, 3 to 20, 4 to 5, 4 to 6, 4 to 7, 4 to 8, 4 to 9, 4 to 10, 5 to 6, 5 to 7, 5 to 8, 5 to 9, 5 to 10, 6 to 7, 6 to 8, 6 to 9, 6 to 10, 7 to 8, 7 to 9, 7 to 10, 8 to 9, 8 to 10, and 9 to 10). Hydrophobicity values can be determined in any useful manner, e.g., XLogP3-AA, which is a computationally generated octanol-water partition coefficient or distribution coefficient including an additive model, e.g., that can be determined according to Cheng T et al., "Computation of octanol-water partition coefficients by guiding an additive model with knowledge," *J. Chem. Inf. Model.* 2007; 47:2140-8; ACD/Log P, which is another computationally generated octanol-water partition coefficient or distribution coefficient having correction factors, e.g., that can be determined according to Petrauskas A A et al., "ACD/Log P method description," *Perspect. Drug Discovery Des.* 2000; 19:99-116 and/or Walker M J, "Training ACD/Log P with experimental data," *QSAR Comb. Sci.* 2004; 23:515-20; and/or topological polar surface area (TPSA), which can be computed using an algorithm according to Ertl P et al., "Fast calculation of molecular polar surface area as a sum of fragment-based contributions and its application to the prediction of drug transport properties," *J. Med. Chem.* 2000; 43:3714-7, each of which is incorporated herein by reference in its entirety.

Non-limiting, exemplary antiviral compounds include, e.g., (E)-2-((1,4-dimethylpiperazin-2-ylidene)amino)-5-nitro-N-phenylbenzamide; (E)-5-cyano-2-((1,4-dimethylpiperazin-2-ylidene)amino)-N-phenylbenzamide; (E)-2-((1,4-dimethylpiperazin-2-ylidene)amino)-N-(4-methoxyphenyl)-5-nitrobenzamide; (E)-2-((1,4-dimethylpiperazin-2-ylidene) amino)-N-(2-fluorophenyl)-5-nitrobenzamide; (E)-4-chloro-5-cyano-2-((1,4-dimethylpiperazin-2-ylidene) amino)-N-phenylbenzamide; (E)-2-((1-ethyl-4-methylpiperazin-2-ylidene)amino)-5-nitro-N-phenylbenzamide; (E)-2-((1,4-dimethylpiperazin-2-ylidene) amino)-5-fluoro-N-phenylbenzamide; (E)-5-cyano-2-((1,4-dimethylpiperazin-2-ylidene)amino)-N-(2-fluorophenyl) benzamide; (E)-5-cyano-2-((1,4-dimethylpiperazin-2-ylidene)amino)-N-(3-fluorophenyl)-benzamide; (E)-2-((1,4-dimethylpiperazin-2-ylidene)amino)-N-(4-methoxyphenyl)-5-nitrobenzamide; (E)-2-((1,4-dimethylpiperazin-2-ylidene) amino)-N-(3-fluorophenyl)-5-nitrobenzamide; (E)-2-((1,4-dimethylpiperazin-2-ylidene)amino)-N-phenyl-5-(trifluoromethyl)benzamide; (E)-2-((1,4-dimethylpiperazin-2-ylidene)amino)-N-(4-fluorophenyl)-5-nitrobenzamide; (E)-2-((1,4-dimethylpiperazin-2-ylidene)amino)-N-(2-methoxyphenyl)-5-nitrobenzamide; (E)-2-((1,4-dimethylpiperazin-2-ylidene)amino)-N-(3-methoxyphenyl)-5-nitrobenzamide; (E)-2-((1,4-dimethylpiperazin-2-ylidene) amino)-N-isopropyl-5-nitrobenzamide; (E)-N-benzyl-2-((1, 4-dimethylpiperazin-2-ylidene)amino)-5-nitrobenzamide; (E)-4-((1,4-dimethylpiperazin-2-ylidene)amino)-N-phenylpyridazine-3-carboxamide; (E)-methyl 4-((1,4-dimethylpiperazin-2-ylidene)amino)-3-(phenylcarbamoyl)benzoate; (E)-2-((1,4-dimethylpiperazin-2-ylidene)amino)-5-nitro-N-(thiophen-3-yl)benzamide; (E)-2-((1,4-dimethylpiperazin-2-ylidene)amino)-4,5-difluoro-N-phenylbenzamide; (E)-5-cyano-2-((1,4-dimethylpiperazin-2-ylidene)amino)-4-fluoro-N-phenylbenzamide; (E)-2-((1, 4-dimethylpiperazin-2-ylidene)amino)-N-methyl-5-nitrobenzamide; 2-[(1,4-dimethylpiperazin-2-ylidene) amino]-5-nitro-N-phenylbenzamide (ML336, XLogP3-AA of 2.1, cLogP of 3.4, Topological Polar Surface Area (TPSA) of 93.8 Å$^2$); 2-[(4-ethylpiperazin-1-yl)methyl]-3-(2-fluorophenyl)-6-nitroquinazolin-4-one (XLogP3-AA of 2.6, TPSA of 85 Å$^2$); 6,7-difluoro-3-phenyl-2-(piperazin-1-ylmethyl) quinazolin-4-one (XLogP3-AA of 2, TPSA of 47.9 Å$^2$); 2-(1,3-diazinan-1-ylmethyl)-6-nitro-3-phenylquinazolin-4-one (XLogP3-AA of 2.1, TPSA of 93.8 Å$^2$) 2-[(1,4-dimethylpiperazin-2-ylidene)amino]-N-(2-fluorophenyl)-5-nitrobenzamide (XLogP3-AA of 2.2, TPSA of 93.8 Å$^2$); 5-cyano-2-[(1,4-dimethylpiperazin-2-ylidene)amino]-N-phenylbenzamide (XLogP3-AA of 2, TPSA of 71.7 Å$^2$); 2-(N-methyl-4-phenylmethoxyanilino)pyrido[3,2-e][1,3] thiazin-4-one (XLogP3-AA of 4.1, TPSA of 80.1 Å$^2$); 2-[(1, 4-dimethylpiperazin-2-ylidene)amino]-N-(4-methoxyphenyl)-5-nitrobenzamide (XLogP3-AA of 2, TPSA of 103 Å$^2$); 2-[(1,4-dimethylpiperazin-2-ylidene)amino]-N-(2-fluorophenyl)-5-nitrobenzamide (XLogP3-AA of 2.2, TPSA of 93.8 Å$^2$); N-[1-[2-[2-chloro-6-(4-chlorophenoxy)pyridin-4-yl]-4-methyl-1,3-thiazol-5-yl]ethylideneamino]aniline (A5, XLogP3-AA of 7.6, TPSA of 87.6 Å$^2$); N-(1,3-benzothiazol-2-yl)-N-methyl-2-thiophen-2-ylacetamide; N-(4,5,6,7-tetrahydro-1,3-benzothiazol-2-yl)-2-thiophen-2-ylacetamide (XLogP3-AA of 2.9, TPSA of 98.5 Å$^2$); N-(4,5,6,7-tetrahydro-1,3-benzothiazol-2-yl)-3-fluoro-2-thiophen-2-ylacetamide; N-phenyl-N-(4,5,6,7-tetrahydro-1,3-benzothiazol-2-yl)-2-thiophen-2-ylacetamide (XLogP3-AA of 4.6, TPSA of 89.7 Å$^2$); 2-[(4-ethylpiperazin-1-yl)methyl]-3-(2-fluorophenyl)-6-nitroquinazolin-4-one (XLogP3-AA of 2.6, TPSA of 85 Å$^2$); 2-(4-phenylmethoxyanilino)pyrido[3,2-e][1,3]thiazin-4-one (XLogP3-AA of 3.9, TPSA of 88.9 Å$^2$); N-[4-[[4-[9-[4-[(4-acetamidophenyl)sulfonylamino]phenyl]fluoren-9-yl]phenyl]sulfamoyl]phenyl]acetamide (compound AN-329/40863801, XLogP3-AA of 6.1, TPSA of 167 Å$^2$); N—[(Z)-1-[4-(dimethylamino)phenyl]-3-(3-imidazol-1-yl-propylamino)-3-oxoprop-1-en-2-yl]benzamide (compound 1111684, XLogP3-AA of 2.9, TPSA of 79.3 Å$^2$); (6Z)-3-[2-[4-(2-methoxyphenyl)piperazin-1-yl]ethoxy]-6-(4-phenyl-1,2-dihydropyrazol-3-ylidene)cyclohexa-2,4-dien-1-one (compound 6052346, XLogP3-AA of 4.2, TPSA of 66.1 Å$^2$); 9H-fluoren-9-ylmethyl N-1-[[1-[[1-(2-((1-carboxy-3-methylbutyl)carboxamido) pyrrolidinyl]H2-(t-butoxy)methyl]-1-oxoethan-2-yl]amino]-5-[[amino-[(4-methoxy-2,3,6-trimethylphenyl)sulfonylamino]methylidene]amino]-1-oxopentan-2-yl]carbamate (compound JFD02946); rintatolimod (Ampligen®); 4-(6,8-dihydro-5H-pyrido[3,4-d]pyrimidin-7-ylmethyl)-2-(5-methylfuran-2-yl)-1,3-thiazole (Z1139230991, XLogP3-AA of 1.8, TPSA of 83.3 Å$^2$); 2-(furan-2-yl)-4-[(2-methyl-6,8-dihydro-5H-pyrido[3,4-d]pyrimidin-7-yl)methyl]-1,3-thiazole (Z1139583813, XLogP3-AA of 1.8, TPSA of 83.3 Å$^2$); 3-(3,5-dimethyl-1,2-oxazol-4-yl)-N-[4-(2-oxo-1,3-dihydroindol-5-yl)-1,3-thiazol-2-yl]propenamide (Z70927013, XLogP3-AA of 2.1, TPSA of 125 Å$^2$); 4-ethyl-N-(3-methoxypropyl)-7,8,9,10-tetrahydro-4H-[1]benzothieno[3,2-f]pyrrolo[1,2-a][1,4]diazepine-5(6H)-carboxamide (G281-1564, Log P of 3.6, ACD/Log P of 4.85, 74.74 Å$^2$); N-(3-ethoxypropyl)-4-isopropyl-7,8,9,10-tetrahydro-4H-[1]benzothieno[3,2-f]pyrrolo[1,2-a][1,4]diazepine-5(6H)-carboxamide (G281-1485, Log P of 4.276, ACD/Log P of 5.73, Polar Surface Area (PSA) of 74.74 Å$^2$), as well as salts thereof. Further antiviral compounds are disclosed in U.S. Pat. No. 9,580,393; U.S. Pat. Pub. No. 2013/085133; Chung D H et al., "Discovery of a broad-spectrum antiviral compound that inhibits pyrimidine biosynthesis and establishes a type 1 interferon-independent antiviral state," *Antimicrob. Agents Chemother.* 2016; 60(8):4552-62; Schecter S et al., "Novel inhibitors targeting Venezuelan equine encephalitis virus capsid protein identified using In Silico Structure-Based-Drug-Design," *Sci. Rep.* 2017; 7:art. no. 17705 (16 pp.); Thomas D R et al., "Identification of novel antivirals inhibiting recognition of Venezuelan equine encephalitis virus capsid protein by the importin α/β1 heterodimer through high-throughput screening," *Antiviral Res.* 2018; 151:8-19; Chung D H et al., "Discovery of a novel compound with anti-Venezuelan equine encephalitis virus activity that targets the nonstructural protein 2," *PLoS Pathog.* 2014; 10(6):e1004213; Julander J G et al., "Treatment of Venezuelan equine encephalitis virus infection with (−)-carbodine," *Antiviral Res.* 2008; 80(3):309-15; Julander J G et al., "C3H/HeN mouse model for the evaluation of antiviral agents for the treatment of Venezuelan equine encephalitis virus infection," *Antiviral Res.* 2008; 78(3):230-41; Kehn-Hall K et al., "Modulation of GSK-3beta activity in Venezuelan equine encephalitis virus infection," *PLoS One* 2012; 7(4):e34761; Langsjoen R M et al., "Host oxidative folding pathways offer novel anti-chikungunya virus drug targets with broad spectrum potential," *Antiviral Res.* 2017; 143:246-51; and Madsen C et al., "Small molecule inhibitors of Ago2 decrease Venezuelan equine encephalitis virus replication," *Antiviral Res.* 2014; 112:26-37, each of which is incorporated herein by reference in its entirety.

In yet other embodiments, the compound or antiviral compound is from a class of quinazolinone-based inhibitors. In particular embodiments, the compound has a structure of formula (I), (II), or (III), or a salt thereof (FIG. 2B). In some embodiments, $R_2$ includes any substituent including an aryl or heterocyclyl moiety. In particular embodiments, each $R_2$ is, independently, optionally substituted aryl, optionally substituted heterocyclyl, optionally substituted alkaryl, or optionally substituted alkheterocyclyl.

In some embodiments, each of $R_1$, $R_3$, $R_4$, $R_5$, $R_7$, and $R_8$ is any useful substituent (e.g., any described herein, such as H, optionally substituted alkyl, optionally substituted aryl, optionally substituted heterocyclyl, optionally substituted alkaryl, optionally substituted alkheterocyclyl, halo, nitro, amino, azido, cyano, hydroxyl, optionally substituted hydroxyalkyl, optionally substituted haloalkyl, optionally substituted perfluoroalkyl, optionally substituted cycloalkyl, or optionally substituted spirocyclyl for two nearby R groups taken together). In particular embodiments, each $R_1$ is, independently, H or optionally substituted alkyl. In some embodiments, each $R_2$ is, independently, optionally substituted aryl, optionally substituted heterocyclyl, optionally substituted alkaryl, or optionally substituted alkheterocyclyl. In other embodiments, each $R_4$, $R_5$, $R_7$, and $R_8$ is, independently, H, optionally substituted alkyl, halo, nitro, amino, azido, cyano, hydroxyl, optionally substituted hydroxyalkyl, optionally substituted haloalkyl, optionally substituted perfluoroalkyl, or optionally substituted cycloalkyl, or in which $R_4$ and $R_5$, taken together, or $R_7$ and $R_8$, taken together, form an optionally substituted spirocyclyl. In some embodiments, each $R_3$ and $R_6$ is, independently, H, optionally substituted alkyl, halo, nitro, nitroso, amino, azido, carboxyl, cyano, hydroxyl, optionally substituted hydroxyalkyl, optionally substituted haloalkyl, optionally substituted perfluoroalkyl, or optionally substituted cycloalkyl.

Other exemplary cargos include an acidic, basic, and hydrophobic drug (e.g., antiviral agents, antibiotic agents, etc.); a protein (e.g., antibodies, carbohydrates, etc.); a nucleic acid (e.g., DNA, RNA, small interfering RNA (siRNA), minicircle DNA (mcDNA), small hairpin RNA (shRNA), complementary DNA (cDNA), naked DNA, and plasmid, as well as chimeras, single-stranded forms, duplex forms, and multiplex forms thereof and including nucleic acid sequences encoding any of these and including one or more modified nucleic acids); a CRISPR component, a nuclease, a plasmid, a plasmid that encodes a CRISPR component, a ribonucleoprotein complex, a Cas enzyme or an ortholog or homolog thereof, a guide RNA, as well as a nucleic acid sequence encoding any of these or a complement thereof); a diagnostic/contrast agent, like quantum dots, iron oxide nanoparticles, gadolinium, and indium-111; a small molecule; a carbohydrate; a drug, a pro-drug, a vitamin, an antibody, a protein, a hormone, a growth factor, a cytokine, a steroid, an anticancer agent, a fungicide, an antimicrobial, an antibiotic, an antiviral agent, etc.; a morphogen; a toxin, e.g., a bacterial protein toxin; a peptide, e.g., an antimicrobial peptide; an antigen; an antibody; a detection agent (e.g., a particle, such as a conductive particle, a microparticle, a nanoparticle, a quantum dot, a latex bead, a colloidal particle, a magnetic particle, a fluorescent particle, etc.; or a dye, such as a fluorescent dye, a luminescent dye, a chemiluminescent dye, a colorimetric dye, a radioactive agent, an electroactive detection agent, etc.); a label (e.g., a quantum dot, a nanoparticle, a microparticle, a barcode, a fluorescent label, a colorimetric label, a radio label (e.g., an RF label or barcode), avidin, biotin, a tag, a dye, a marker, an electroactive label, an electrocatalytic label, and/or an enzyme that can optionally include one or more linking agents and/or one or more dyes); a capture agent (e.g., such as a protein that binds to or detects one or more markers (e.g., an antibody or an enzyme), a globulin protein (e.g., bovine serum albumin), a nanoparticle, a microparticle, a sandwich assay reagent, a catalyst (e.g., that reacts with one or more markers), and/or an enzyme (e.g., that reacts with one or more markers, such as any described herein)); as well as combinations thereof.

Core

The present invention relates, in part, to a particle having a core. The core can provide any useful benefit. In particular non-limiting embodiments, the core provides a surface upon which a lipid layer can be supported. In other non-limiting embodiments, the core provides a charged surface that allows for electrostatic interactions with the cargo and/or the lipid layer, or a portion thereof.

The core can be characterized in any useful manner. In one instance, the core can be characterized by a first dimension (e.g., core circumference, pore size of the core, core diameter, core length, or core width). Exemplary values for a core dimension (e.g., core circumference, core diameter, core length, or core width, as well as an average or mean value for any of these) include, without limitation, greater than about 1 nm (e.g., greater than about 5 nm, 10 nm, 20 nm, 30 nm, 40 nm, 50 nm, 60 nm, 70 nm, 80 nm, 90 nm, 100 nm, 125 nm, 150 nm, 200 nm, 300 nm, 500 nm, 750 nm, 1 µm, 2 µm, 5 µm, 10 µm, 20 µm, or more), including of from about 5 nm to about 300 nm (e.g., from 5 nm to 20 nm, 5 nm to 30 nm, 5 nm to 40 nm, 5 nm to 50 nm, 5 nm to 75 nm, 5 nm to 100 nm, 5 nm to 150 nm, 5 nm to 200 nm, 5 nm to 250 nm, 10 nm to 20 nm, 10 nm to 30 nm, 10 nm to 40 nm, 10 nm to 50 nm, 10 nm to 75 nm, 10 nm to 100 nm, 10 nm to 150 nm, 10 nm to 200 nm, 10 nm to 250 nm, 10 nm to 300 nm, 25 nm to 30 nm, 25 nm to 40 nm, 25 nm to 50 nm, 25 nm to 75 nm, 25 nm to 100 nm, 25 nm to 150 nm, 25 nm to 200 nm, 25 nm to 250 nm, 25 nm to 300 nm, 50 nm to 75 nm, 50 nm to 100 nm, 50 nm to 150 nm, 50 nm to 200 nm, 50 nm to 250 nm, 50 nm to 300 nm, 75 nm to 100 nm, 75 nm to 150 nm, 75 nm to 200 nm, 75 nm to 250 nm, 75 nm to 300 nm, 100 nm to 150 nm, 100 nm to 200 nm, 100 nm to 250 nm, 100 nm to 300 nm, 150 nm to 200 nm, 150 nm to 250 nm, 150 nm to 300 nm, 200 nm to 250 nm, 200 nm to 300 nm, 250 nm to 300 nm, or 275 nm to 300 nm). In one instance, the particle includes a porous core (e.g., a silica core that is spherical and ranges in diameter from about 10 nm to about 250 nm (e.g., having a mean diameter of about 150 nm)). In particular embodiments, the silica core is monodisperse or polydisperse in size distribution. The core can be further characterized by an electrostatic property. In some embodiments, the core has a negative charge (e.g., a net negative charge), such as a zeta potential of from about −10 mV to about −200 mV (e.g., from −10 mV to −100 mV, −10 mV to −75 mV, −10 mV to −50 mV, −10 mV to −30 mV, −15 mV to −100 mV, −15 mV to −75 mV, −15 mV to −50 mV, −15 mV to −30 mV, −20 mV to −100 mV, −20 mV to −75 mV, −20 mV to −50 mV, −20 mV to −30 mV, −30 mV to −100 mV, −30 mV to −75 mV, −30 mV to −50 mV, −40 mV to −100 mV, −40 mV to −75 mV, −40 mV to −50 mV, −50 mV to −100 mV, −50 mV to −75 mV, −60 mV to −100 mV, or −60 mV to −75 mV).

The core can be porous. In particular embodiments, the pore has a dimension (e.g., average pore size, pore diameter, pore radius, pore circumference, pore length, pore width, or pore depth) that is greater than about 0.5 nm (e.g., of from about 0.5 nm to about 30 nm, including from 0.5 nm to 10 nm, 0.5 nm to 20 nm, 0.5 nm to 25 nm, 1 nm to 10 nm, 1 nm to 15 nm, 1 nm to 20 nm, 1 nm to 25 nm, 1 nm to 30 nm, 2 nm to 5 nm, 2 nm to 10 nm, 2 nm to 20 nm, 2 nm to 25 nm, or 2 nm to 30 nm).

A particle or a portion thereof (e.g., a core) may have a variety of shapes and cross-sectional geometries that may depend, in part, upon the process used to produce the particles. The core or particle can be a nanoparticle (e.g., having a diameter less than about 1 µm) or a microparticle (e.g., having a diameter greater than or equal to about 1 µm).

In one embodiment, a core or particle may have a shape that is a sphere, a donut (toroidal), a rod, a tube, a flake, a fiber, a plate, a wire, a cube, or a whisker. A collection of cores may have two or more of the aforementioned shapes. In one embodiment, a cross-sectional geometry of the core may be one or more of circular, ellipsoidal, triangular, rectangular, or polygonal. In one embodiment, a core may consist essentially of non-spherical cores. For example, such cores may have the form of ellipsoids, which may have all three principal axes of differing lengths, or may be oblate or prelate ellipsoids of revolution. Non-spherical cores alternatively may be laminar in form, wherein laminar refers to particles in which the maximum dimension along one axis is substantially less than the maximum dimension along each of the other two axes. Non-spherical cores may also have the shape of frusta of pyramids or cones, or of elongated rods. In one embodiment, the cores may be irregular in shape. In one embodiment, a plurality of cores may consist essentially of spherical cores. Particles and cores for use in the present invention may be PEGylated and/or aminated as otherwise described in Int. Pub. Nos. WO 2015/042268 and WO 2015/042279, which is incorporated herein by reference in their entirety.

The particle size distribution (e.g., size of the core for the particle or a size of the silica carrier), according to the present invention, depends on the application, but is principally monodisperse (e.g., a uniform sized population varying no more than about 5-20% in diameter, as otherwise described herein). In certain embodiments, particles or cores can range, e.g., from around 1 nm to around 500 nm in size, including all integers and ranges there between. The size is measured as the longest axis of the core. In various embodiments, the cores are from around 5 nm to around 500 nm and from around 10 nm to around 100 nm in size. In certain alternative embodiments, the cores or particles are monodisperse and range in size from about 25 nm to about 300 nm. The sizes used preferably include 50 nm (+/−10 nm) and 150 nm (+/−15 nm), within a narrow monodisperse range, but may be more narrow in range.

When the core is porous, the pores can be from around 0.5 nm to about 25 nm in diameter, often about 1 to around 20 nm in diameter, including all integers and ranges there between. In one embodiment, the pores are from around 1 to around 10 nm in diameter. In one embodiment, around 90% of the pores are from around 1 to around 20 nm in diameter. In another embodiment, around 95% of the pores are around 1 to around 20 nm in diameter.

In certain embodiments, preferred cores or particles according to the present invention: are monodisperse and range in size from about 25 nm to about 300 nm; exhibit stability (colloidal stability); have single cell binding specification to the substantial exclusion of non-targeted cells; are anionic, neutral or cationic for specific targeting (preferably cationic); are optionally modified with agents such as PEI (polyethylene imine), $NMe^{3+}$, dye, crosslinker, ligands (ligands provide neutral charge); and optionally, are used in combination with a cargo to be delivered to the target.

In certain alternative embodiments, the present invention is directed to cores or particles of a particular size (diameter) ranging from about 0.5 to about 30 nm, about 1 nm to about 30 nm, often about 5 nm to about 25 nm (preferably, less than about 25 nm), often about 10 to about 20 nm, for administration in any useful route. In some embodiments, these cores or particles are often monodisperse and provide colloidally stable compositions. These compositions can be used to target host cells because of enhanced biodistribution/bioavailability of these compositions, and optionally, specific cells, with a wide variety of therapeutic and/or diagnostic agents that exhibit varying release rates at the site of activity.

The cores can be produced in any useful manner. In one instance, cores are formed by templating with a surfactant, a cross-linked micelle, a detergent, or any other useful molecule (see, e.g., Gao F et al., *J. Phys. Chem. B.* 2009; 113:1796-804; Lin Y S et al., Chem. Mater. 2009; 21(17): 3979-86; and Zhang K et al., *J. Am. Chem. Soc.* 2013 Feb. 20; 135(7):2427-30). In yet another instance, cores are formed by dendritic growth (see, e.g., Shen D et al., *Nano Lett.* 2014 Feb. 12; 14(2):923-32). Each batch of cores or particles can be characterized in any useful manner, such as by assessment of size and surface charge using dynamic light scattering (DLS) (NIST-NCL PCC-1 and PCC-2) and electron microscopy (NIST-NCL PCC-7 and PCC-15) and verification of low endotoxin contamination per health industry product standards (NCL STE-1.1). Resultant cores can be further processed, such as by modifying core condensation (e.g., by using acidified ethanol for silica), modifying core surface charge (e.g., by use of amine-containing silanes, such as APTES), etc.

The core can be formed of any useful material (e.g., a metal oxide, alum, silica, including mesoporous forms thereof). In particular embodiments, the core is composed of a mesoporous silica nanoparticle (MSN). Exemplary, non-limiting MSNs for use in the present invention are described in Int. Pub. Nos. WO 2015/042268 and WO 2015/042279, each of which is incorporated herein in its entirety.

Lipid Layer

The present invention relates to a lipid layer disposed around a core. The lipid layer can be characterized in any useful manner, such as by the thickness of the layer (e.g., of from about 5 nm to about 50 nm), the number of layers within the lipid layer (e.g., two, three, four, five, six, seven, or more lipid bilayers), and/or the net charge of the lipid layer (e.g., a net non-negative charge, such as a net positive charge; or as determined by the composition of the lipid layer, such as a layer formed by use of a liposome formulation having more than about 20 mol. % of a cationic lipid, such as any herein (e.g., DOTAP)).

The lipid layer can include any useful component, including a cationic lipid, a pegylated lipid, a zwitterionic lipid, and/or a cholesterol. For instance, the lipid layer can include any useful lipid or combination of lipids or component, such as one or more lipids selected from the group of 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-distearoyl-sn-glycero-3-phosphoethanolamine (DSPE), 1,2-dilauroyl-sn-glycero-3-phosphocholine (DLPC), 1,2-dimyristoyl-sn-glycero-3-phosphocholine (DMPC), 1-palmitoyl-2-oleoyl-sn-glycero-3-phosphocholine (POPC), 1-stearoyl-2-oleoyl-sn-glycero-3-phosphocholine (SOPC), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-oleoyl-2-[12-[(7-nitro-2-1,3-benzoxadiazol-4-yl)amino]lauroyl]-sn-glycero-3-phosphocholine (18:1-12:0 NBD PC), 1,2-di stearoyl-sn-glycero-3-phosphoethanolamine-N-[methoxy-(polyethylene glycol)-2000] (DSPE-PEG$_{2000}$), 1-palmitoyl-2-{12-[(7-nitro-2-1,3-benzoxadiazol-4-yl)amino]lauroyl}-sn-glycero-3-phosphocholine (16:0-12:0 NBD PC), a sterol (e.g., cholesterol, desmosterol, diploptterol, cholestanol, cholic acid, 12-deoxycholic acid, 7-deoxycholic acid, or a derivative thereof, such as cholesterol sulfate), and mixtures thereof and conjugated forms thereof (e.g., conjugated to PEG moieties, peptides, polypeptides, including immunogenic peptides, proteins and antibodies, and nucleic acids (e.g., RNA and DNA) by way of a covalent bond or by way of any useful linker (e.g., any described herein).

Exemplary, non-limiting sterols include cholesterol (e.g., from ovine wool or from plant sources), campestanol, campesterol, cholestanol, cholestenone, desmosterol, 7-dehydrodesmosterol, dehydroepiandrosterone (DHEA), desmosterol, diosgenin, FF-MAS (14-demethyl-14-dehydrolanosterol), lanosterol, lathosterol, pregnenolone, sitostanol, sitosterol, stigmasterol, zymosterol, zymostenol, zymosterone, as well as derivatives thereof, such as sulfates thereof, esters thereof, stereoisomers thereof, deuterated forms thereof, sulfonated forms thereof, phosphorylated forms thereof, unsaturated forms thereof, keto forms thereof, oxidized forms thereof, an oxysterol thereof, PEGylated forms thereof (e.g., cholesterol-(polyethylene glycol-600)), or substituted forms thereof (e.g., having one or more hydroxyl, epoxy, alkyl, phospho, and/or halo, such as fluoro) .

Cores, lipids, and cargos can be PEGylated with a variety of polyethylene glycol-containing compositions as described herein. PEG molecules can have a variety of lengths and molecular weights and include, but are not limited to, PEG 200, PEG 1000, PEG 1500, PEG 2000, PEG 4600, PEG 5000, PEG 10,000, PEG-peptide conjugates or combinations thereof.

In one instance, the lipid layer includes DOPE and DOTAP. In another instance, the lipid layer includes a zwitterionic lipid (e.g., DOPC, DPPC, DOPE, DPPE, DSPE, DLPC, DMPC, POPC, or SOPC) with an optional PEG (e.g., PEG, PEG-2000 PE, PEG conjugated to DOPE, PEG conjugated to DPPE, PEG conjugated to DSPE, etc.).

In yet another instance, the lipid layer includes DOTAP and cholesterol in a 1:1 molar ratio. In another instance, the lipid layer includes PEG. In yet another instance, the lipid layer includes DOPE. In one instance, the lipid layer includes DOTAP in combination with about 4 mol. % DOPE, about 47 mol. % cholesterol, and about 2 mol. % DSPE-PEG$_{2000}$. In another instance, the lipid layer includes about 10 to about 50 mol. % DOTAP, about 40 to 50 mol. % cholesterol, about 0 to 40 mol. % DOPE, and about 1 to 5 mol. % of a PEGylated lipid.

The lipid layer can be formed by employing any useful lipid formulation. A non-limiting exemplary formulation can include the following: about 1 mol. % to about 5 mol. % of a PEGylated lipid (e.g., from 1 mol. % to 3 mol. %, 1 mol. % to 4 mol. %, 2 mol. % to 3 mol. %, 2 mol. % to 4 mol. %, 2 mol. % to 5 mol. %, 3 mol. % to 4 mol. %, or 3 mol. % to 5 mol. %); about 30 mol. % to about 60 mol. % of a sterol (e.g., from 30 mol. % to 50 mol. %, 35 mol. % to 50 mol. %, 35 mol. % to 60 mol. %, 40 mol. % to 50 mol. %, 40 mol. % to 60 mol. %, 45 mol. % to 50 mol. %, 45 mol. % to 60 mol. %, 50 mol. % to 60 mol. %, or 55 mol. % to 60 mol. %); about 20 mol. % to about 90 mol. % of a cationic lipid (e.g., from 20 mol. % to 30 mol. %, 20 mol. % to 40 mol. %, 20 mol. % to 50 mol. %, 20 mol. % to 60 mol. %, 20 mol. % to 70 mol. %, 20 mol. % to 80 mol. %, 30 mol. % to 40 mol. %, 30 mol. % to 50 mol. %, 30 mol. % to 60 mol. %, 30 mol. % to 70 mol. %, 30 mol. % to 80 mol. %, 30 mol. % to 90 mol. %, 40 mol. % to 50 mol. %, 40 mol. % to 60 mol. %, 40 mol. % to 70 mol. %, 40 mol. % to 80 mol. %, 40 mol. % to 90 mol. %, 50 mol. % to 60 mol. %, 50 mol. % to 70 mol. %, 50 mol. % to 80 mol. %, 50 mol. % to 90 mol. %, 60 mol. % to 70 mol. %, 60 mol. % to 80 mol. %, 60 mol. % to 90 mol. %, 70 mol. % to 80 mol. %, 70 mol. % to 90 mol. %, or 80 mol. % to 90 mol. %); and about 0 mol. % to about 40 mol. % of a zwitterionic lipid (e.g., 0 mol. % to 3 mol. %, 0 mol. % to 5 mol. %, 0 mol. % to 7 mol. %, 0 mol. % to 10 mol. %, 0 mol. % to 15 mol. %, 0 mol. % to 20 mol. %, 0 mol. % to 25 mol. %, 0 mol. % to 30 mol. %, 0 mol. % to 35 mol. %, 3 mol. % to 5 mol. %, 3 mol. % to 7 mol. %, 3 mol. % to 10 mol. %, 3 mol. % to 15 mol. %, 3 mol. % to 20 mol. %, 3 mol. % to 25 mol. %, 3 mol. % to 30 mol. %, 3 mol. % to 35 mol. %, 3 mol. % to 40 mol. %, 7 mol. % to 10 mol. %, 7 mol. % to 15 mol. %, 7 mol. % to 20 mol. %, 7 mol. % to 25 mol. %, 7 mol. % to 30 mol. %, 7 mol. % to 35 mol. %, 73 mol. % to 40 mol. %, 10 mol. % to 15 mol. %, 10 mol. % to 20 mol. %, 10 mol. % to 25 mol. %, 10 mol. % to 30 mol. %, 10 mol. % to 35 mol. %, 10 mol. % to 40 mol. %, 15 mol. % to 20 mol. %, 15 mol. % to 25 mol. %, 15 mol. % to 30 mol. %, 15 mol. % to 35 mol. %, 15 mol. % to 40 mol. %, 20 mol. % to 25 mol. %, 20 mol. % to 30 mol. %, 20 mol. % to 35 mol. %, 20 mol. % to 40 mol. %, 25 mol. % to 30 mol. %, 25 mol. % to 35 mol. %, 25 mol. % to 40 mol. %, 30 mol. % to 35 mol. %, 30 mol. % to 40 mol. %, or 35 mol. % to 40 mol. %), or salts of any of these (e.g., pharmaceutically acceptable salts, such as any described herein).

In particular embodiments, the ratio of the sterol to the cationic lipid is about 1:1. In other embodiments, the lipid formulation includes about 2% of the PEGylated lipid. In yet other embodiments, the lipid formulation includes about 30 mol. % to about 60 mol. % of the cationic lipid.

The lipid formulation can include any useful lipid or component. Exemplary PEGylated lipids (e.g., a lipid having a poly(ethylene glycol) moiety)) include PEGylated DSPE (e.g., 1,2-distearoyl-sn-glycero-3-phosphoethanolamine-N-[amino(polyethylene glycol)-X] (DSPE X) or N-[carbonyl-2',3'-bis(methoxypolyethyleneglycol X)]-1,2-distearoyl-sn-glycero-3-phosphoethanolamine (DSPE-2arm PEGX)), PEGylated phosphoethanolamine (PE) (e.g., 1,2-dioleoyl-sn-glycero-3-phosphoethanolamine-N-[methoxy (polyethylene glycol)-X] (18:1 PEGX PE), 1,2-distearoyl-sn-glycero-3-phosphoethanolamine-N-[methoxy (polyethylene glycol)-X] (18:0 PEGX PE), 1,2-dimyristoyl-sn-glycero-3-phosphoethanolamine-N-[methoxy (polyethylene glycol)-X] (14:0 PEGX PE), or 1,2-dipalmitoyl-sn-glycero-3-phosphoethanolamine-N-[methoxy(polyethylene glycol)-5000] (16:0 PEGX PE)), PEGylated DPPE (e.g., N-(carbonyl-methoxypolyethyleneglycol X)-1,2-dipalmitoyl-sn-glycero-3-phosphoethanolamine), PEGylated DMPE (e.g., N-(carbonyl-methoxypolyethyleneglycol X)-1,2-dimyristoyl-sn-glycero-3-phosphoethanolamine), PEGylated DPG (e.g., 1,2-dipalmitoyl-sn-glycerol, methoxypolyethylene glycol), PEGylated DSG (e.g., 1,2-distearoyl-sn-glycerol, methoxypolyethylene glycol), PEGylated DOG (e.g., 1,2-dioleoyl-sn-glycerol, methoxypolyethylene glycol), or PEGylated DMG (e.g., 1,2-dimyristoyl-sn-glycerol, methoxypolyethylene glycol), where X indicates an approximate weight average molecular weight (Mw) or approximate number average molecular weight (Mn), and where can be X 500, 3000, 2000, 1000, 750, 550, or 350.

Exemplary sterols include, e.g., cholesterol, a derivative thereof, or any described herein. Exemplary zwitterionic lipids include DOPC, DPPC, DOPE, DPPE, POPC, DLPC, DSPC, DMPC, SOPC, or any described herein.

Exemplary cationic lipids include 1,2-dioleoyl-3-trimethylammonium-propane (DOTAP), 1,2-stearoyl-3-trimethylammonium-propane (18:0 TAP), 1,2-dipalmitoyl-3-trimethylammonium-propane (16:0 TAP), 1,2-dimyristoyl-3-trimethylammonium-propane (14:0 TAP), 1,2-di-O-octadecenyl-3-trimethylammonium propane (DOTMA), N1-[2-((1S)-1-[(3-aminopropyl)amino]-4-[di(3-amino-propyl)amino]butylcarboxamido)ethyl]-3,4-di[oleyloxy]-benzamide (MVL5), ethylphosphocholine (ethyl PC) (e.g., 1,2-dimyristoleoyl-sn-glycero-3-ethylphosphocholine, 1-palmitoyl-2-oleoyl-sn-glycero-3-ethylphosphocholine, 1,2-dioleoyl-sn-glycero-3-ethylphosphocholine, 1,2-distearoyl-sn-glycero-3-ethylphosphocholine, 1,2-dipalmitoyl-sn-glycero-3-ethylphosphocholine, 1,2-dimyristoyl-sn-glycero-3-ethylphosphocholine, or 1,2-dilauroyl-sn-glycero-3-ethylphosphocholine), dimethyldioctadecylammonium (DDAB), 1,2-dipalmitoyl-sn-glycero-O-ethyl-3-phosphocholine (EDPPC), or any described herein.

The lipid layer of the particle can be composed of lipids and components in an amount similar to that provided by the lipid formulation. For instance, an exemplary lipid formulation comprising about 47 mol. % of a cationic lipid can provide a lipid layer (for a lipid-coated particle) that comprises 47 mol. % of that cationic lipid. Thus, any composition provided for a lipid formulation herein also provides a composition for the lipid layer.

Targeting Ligands

The lipid-coated particle can include one or more cell targeting species, cell penetrating peptides, fusogenic peptides, and/or targeting peptides. Such species can be included within the cargo, configured to be expressed by a plasmid of the cargo, located within the lipid layer, and/or provided by an external surface of the lipid layer (e.g., provided by the outer lipid layer). The composition of the lipid layer can include one or more components that facilitate ligand orientation, maximize cellular interaction, provide lipid stability, and/or confer enhanced cellular entry.

In some instances, the targeting ligand can be a cell penetration peptide, a fusogenic peptide, or an endosomolytic peptide, which are peptides that aid a particle in translocating across a lipid bilayer, such as a cellular membrane or endosome lipid bilayer of the host cell. In one embodiment, the targeting ligand is optionally crosslinked onto a lipid layer surface of the outer lipid layer.

Endosomolytic peptides are a sub-species of fusogenic peptides as described herein. Representative and preferred electrostatic cell penetration (fusogenic) peptides include an 8 mer polyarginine ($NH_2$-RRRRRRRR-COOH, SEQ ID NO:1), among others known in the art, which are included in or on particles in order to enhance the penetration of into cells. Representative endosomolytic fusogenic peptides ("endosomolytic peptides") include H5WYG peptide ($NH_2$-GLFHAIAHFIHGGWHGLIHGWYGGC-COOH, SEQ ID NO:2), RALA peptide ($NH_2$-WEARLARALARALARHLARALARALRAGEA-COOH, SEQ ID NO:3), KALA peptide ($NH_2$-WEAKLAKALAKALAKHLAKALAKA-LKAGEA-COOH), SEQ ID NO:4), GALA ($NH_2$-WEAA-LAEALAEALAEHLAEALAEALEALAA-COOH, SEQ ID NO:5) and INF7 ($NH_2$-GLFEAIEGFIENGWEG-MIDGWYG-COOH, SEQ ID NO:6), or fragments thereof, among others. In one instance, the targeting ligand includes an amino acid sequence having at least 80% sequence identity (e.g., at least 85%, 90%, 95%, or 99% sequence identity) to any one of SEQ ID NOs:1-6, or a fragment thereof.

Proteins gain entry into the nucleus through the nuclear envelope. Yet other ligands can include a nuclear localization sequence (NLS), e.g., NH$_2$-GNQSSNFGPMKGGNFG-GRSSGPY GGGGQYFAKPRNQGGYGGC-COOH (SEQ ID NO:9), RRMKWKK (SEQ ID NO:10), PKKKRKV (SEQ ID NO:11), and KR[PAATKKAGQA]KKKK (SEQ ID NO:12), the NLS of nucleoplasmin, a prototypical bipartite signal comprising two clusters of basic amino acids, separated by a spacer of about 10 amino acids. Numerous other nuclear localization sequences are well known in the art. See, for example, LaCasse E C et al., "Nuclear localization signals overlap DNA- or RNA-binding domains in nucleic acid-binding proteins," *Nucl. Acids Res.* 1995; 23:1647-56; Weis, K, "Importins and exportins: how to get in and out of the nucleus," [*published erratum appears in Trends Biochem. Sci.* 1998 July; 23(7):23.5] Trends Biochem. Sci. 1998; 23:185-9; and Cokol M et al., *EMBO Rep.* 2000 Nov. 15; 1(5): 411-5, each of which is incorporated herein by reference in its entirety.

Preferred ligands which may be used to target cells include peptides, affibodies, and antibodies (including monoclonal and/or polyclonal antibodies). In certain embodiments, targeting ligands selected from the group consisting of Fcγ from human IgG (which binds to Fcγ receptors on macrophages and dendritic cells), human complement C$_3$ (which binds to CR1 on macrophages and dendritic cells), ephrin B2 (which binds to EphB4 receptors on alveolar type II epithelial cells), SP94 peptide (which binds to unknown receptor(s) on hepatocyte-derived cells), and MET receptor binding peptide. Exemplary, non-limiting SP94 peptides include SP94 free peptide (H2N-SFSIILT-PILPL-COOH, SEQ ID NO:13), a SP94 peptide modified with C-terminal Cys for conjugation (H2N-SFSIILTPIL-PLGGC-COOH, SEQ ID NO:14), and a further modified SP94 peptide (H2N-SFSIILTPILPLEEEGGC-COOH, SEQ ID NO:15). Exemplary MET binding peptides include ASVHFPP (SEQ ID NO:16), TATFWFQ (SEQ ID NO:17), TSPVALL (SEQ ID NO:18), IPLKVHP (SEQ ID NO:19), and WPRLTNM (SEQ ID NO:20).

Other exemplary targeting ligands include poly-L-arginine, including (R)n, where 6<n<12, such as an R$_{12}$ peptide (e.g., RRRRRRRRRRRR (SEQ ID NO:21)) or an R$_9$ peptide (e.g., RRRRRRRRR (SEQ ID NO:22)); a poly-histidine-lysine, such as a (KH)$_9$ (e.g., KHKHKHKHKHKHKHKH (SEQ ID NO:23)); a Tat protein or derivatives and fragments thereof, such as RKKRRQRRR (SEQ ID NO:24), GRKKRRQRRRPQ (SEQ ID NO:25), GRKKRRQRRR (SEQ ID NO:26), GRKKRRQRRRPPQ (SEQ ID NO:27), YGRKKRRQRRR (SEQ ID NO:28), and RKKRRQRRRRKKRRQRRR (SEQ ID NO:29); a Cady protein or derivatives and fragments thereof, such as Ac-GLWRALWRLLRSLWRLLWRA-cysteamide (SEQ ID NO:30); a penetratin protein or derivatives and fragments thereof, such as RQIKIWFQNRRMKWKKGG (SEQ ID NO:31), RQIRIWFQNRRMRWRR (SEQ ID NO:32), and RQIKIWFQNRRMKWKK (SEQ ID NO:33); an antitrypsin protein or derivatives and fragments thereof, such as CSIPPEVKFNKPFVYLI (SEQ ID NO:34); a temporin protein or derivatives and fragments thereof, such as FVQWFSKFLGRIL-NH$_2$ (SEQ ID NO:35); a MAP protein or derivatives and fragments thereof, such as KLALKLA-LKALKAALKLA (SEQ ID NO:36); a RW protein or derivatives and fragments thereof, such as RRWWRRWRR (SEQ ID NO:37); a pVEC protein or derivatives and fragments thereof, such as LLIILRRRIRKQAHAHSK (SEQ ID NO:38); a transportan protein or derivatives and fragments thereof, such as GWTLNSAGYLLGKIN LKALAALAK-KIL (SEQ ID NO:39); a MPG protein or derivatives and fragments thereof, such as GALFLGFL-GAAGSTMGAWSQPKKKRKV (SEQ ID NO:40); a Pep protein or derivatives and fragments thereof, such as KETWWETWWTEWSQPKKKRKV (SEQ ID NO:41), Ac-KETWWETWWTEWSQPKKKRKV-cysteamine (SEQ ID NO:42), and WKLFKKILKVL-amide (SEQ ID NO:43); a Bp100 protein or derivatives and fragments thereof, such as KKLFKKILKYL (SEQ ID NO:44) and KKLFKKIL-KYL-amide (SEQ ID NO:45); a maurocalcine protein or derivatives and fragments thereof, such as GDC(acm)L-PHLKLC (SEQ ID NO:46); a calcitonin protein or derivatives and fragments thereof, such as LGTYTQDFNKFHTFPQTAIGVGAP (SEQ ID NO:47); a neurturin protein or derivatives and fragments thereof, such as GAAEAAARVYDLGLRRLRQRRRLRRERVRA (SEQ ID NO:48); and a human P1 protein or derivatives and fragments thereof, such as MGLGLHLLV-LAAALQGAWSQPKKKRKV (SEQ ID NO:49).

In one instance, the targeting ligand includes an amino acid sequence having at least 80% sequence identity (e.g., at least 85%, 90%, 95%, or 99% sequence identity) to any one of SEQ ID NOs:10-12 and 21-49 or a fragment thereof (e.g., having a length of about 4, 5, 6, 7, 8, 9, 10, 11, 12, 13, 14, 15, 16, 17, 18, 19, 20, 22, 24, 26, 28, 30, 32, 34, 36, 38, 40, or more amino acids).

Particle Characteristics and Surface Properties

The lipid-coated particle can be characterized by any useful characteristic (e.g., overall charge, dimension, dispersity, etc.). In some embodiments, one or more optional targeting ligands can be present in or on a lipid layer. The particle can have any useful dimension, such as diameter, circumference, length, width, height, etc. Exemplary values for dimensions include, without limitation, greater than about 10 nm (e.g., greater than about 20 nm, 30 nm, 40 nm, 50 nm, 60 nm, 70 nm, 80 nm, 90 nm, 100 nm, 125 nm, 150 nm, 200 nm, 300 nm, 500 nm, 750 nm, 1 μm, 2 μm, 5 μm, 10 μm, 20 μm, or more) or of from about 2 nm to 500 nm (e.g., from 2 nm to 50 nm, 2 nm to 100 nm, 2 nm to 150 nm, 2 nm to 200 nm, 2 nm to 300 nm, 2 nm to 400 nm, 10 nm to 50 nm, 10 nm to 100 nm, 10 nm to 150 nm, 10 nm to 200 nm, 10 nm to 300 nm, 10 nm to 400 nm, 10 nm to 500 nm, 20 nm to 50 nm, 20 nm to 100 nm, 20 nm to 150 nm, 20 nm to 200 nm, 20 nm to 300 nm, 20 nm to 400 nm, 20 nm to 500 nm, 50 nm to 100 nm, 50 nm to 150 nm, 50 nm to 200 nm, 50 nm to 300 nm, 50 nm to 400 nm, 50 nm to 500 nm, 100 nm to 150 nm, 100 nm to 200 nm, 100 nm to 300 nm, 100 nm to 400 nm, 100 nm to 500 nm, 150 nm to 200 nm, 150 nm to 300 nm, 150 nm to 400 nm, 150 nm to 500 nm, 200 nm to 300 nm, 200 nm to 400 nm, or 200 nm to 500 nm).

In particular embodiments, a plurality of particles is monodisperse, such as by having a polydispersity index (PdI) that is less than about 0.2 or by having a PdI that is of from about 0.05 to about 0.2 (e.g., from 0.05 to 0.1, 0.05 to 0.15, 0.1 to 0.15, 0.1 to 0.2, or 0.15 to 0.2). In some embodiments, the monodisperse particles range in a size of from about 20 nm to about 300 nm (e.g., from 50 nm (+1-10 nm) to 150 nm (+1-15 nm)). In other embodiments, the particle (or a plurality of particles) has a charge (or a net charge) that is near neutral (e.g., a zeta potential of from about +5 mV to −5 mV).

In certain alternative embodiments, the present invention is directed to particles of a particular size (diameter) ranging from about 0.5 to about 30 nm, about 1 nm to about 30 nm, often about 5 nm to about 25 nm (preferably, less than about 25 nm), often about 10 to about 20 nm, for administration via intravenous, intramuscular, intraperitoneal, retro-orbital, and subcutaneous injection routes. These particles can be monodisperse and provide colloidally stable compositions.

The surface properties of the particle can be optimized in any useful manner. For instance, the lipid layer can have an appropriate charge (e.g., approximately net neutral charge), can include appropriate targeting ligands to promote their cell-specific binding and internalization, and can include useful ligand (e.g., to promote endosomal escape or nuclear localization within host cells).

Any useful ligand can be employed. The type and density of targeting ligands can be optimized to enhance uptake by the target. Exemplary ligands include a peptide that binds to ephrin B2, which we identified using phage display, to target Vero cells; Fcγ to target THP-1 cells and primary alveolar macrophages; the 'GE11' peptide (see, e.g., Li Z et al., *FASEB J* 2005; 19: 1978-85) to target A549 cells and primary alveolar epithelial cells; the 'SP94' peptide (see, e.g., Lo A et al., *Molec. Cancer Therap.* 2008; 7:579-89) to target HepG2 cells and primary hepatocytes; human complement $C_3$, which binds to receptors on macrophages and dendritic cells; or the 'H5WYG' peptide, which ruptures the membranes of acidic intracellular vesicles via the 'proton sponge' mechanism (see, e.g., Moore N M et al., *J. Gene. Med.* 2008 10: 1134-49).

Other ligands include a peptide (e.g., a peptide zip code or a cell penetrating peptide), an endosomolytic peptide, an antibody (including fragments thereof), affibodies, a carbohydrate, an aptamer, a cluster of differentiation (CD) protein, or a self-associated molecular pattern (SAMP) (e.g., as described in Lambris J D et al., *Nat. Rev. Microbiol.* 2008; 6(2):132; and Poon I K H, *Cell Death Differ.* 2010; 17:381-97, each of which is incorporated herein by reference in its entirety). Exemplary CD proteins include CD47 (OMIM Entry No. 601028, a marker of self that allows RBC to avoid phagocytosis), CD59 (OMIM Entry No. 107271, a marker that prevents lysis by complement), C1 inhibitor (C1INH, OMIM Entry No. 606860, a marker that suppresses activation of the host's complement system), CD200 (OMIM Entry No. 155970, an immunosuppressive factor), CD55 (OMIM Entry No. 125240, a marker that inhibits the complement cascade), CD46 (OMIM Entry No. 120920, a marker that inhibits the complement cascade), and CD31 (OMIM Entry No. 173445, an adhesion regulator and a negative regulator of platelet-collagen interactions). Each recited OMIM Entry is incorporated herein by reference in its entirety.

Any other useful ligand can be employed, such as those identified by the 'BRASIL' (Biopanning and Rapid Analysis of Selective Interactive Ligands) method (see, e.g., Giordano R J et al., *Nat. Med.* 2001; 7:1249-53; Giordano R J et al., *Proc. Natl Acad. Sci.USA* 2010; 107(11):5112-7; and Kolonin M G et al., *Cancer Res.* 2006; 66:34-40) to identify novel targeting peptides and single-chain variable fragments (scFvs) via phage display (see, e.g., Giordano R J et al., *Chem. Biol.* 2005; 12:1075-83; Giordano R J et al., *Proc. Natl Acad. Sci. USA* 2010; 107(11):5112-7; Kolonin M G et al., *Cancer Res.* 2006; 66:34-40; Tonelli R R et al., *PLoS Negl. Dis.* 2010; 4:e864; Lionakis M S et al., *Infect. Immun.* 2005; 73:7747-58; and Barbu E M et al., *PLoS Pathog.* 2010; 6:e1000726).

Methods

The lipid-coated particles herein can be employed in any useful manner. The present particles can be adapted to recognize the target and, if needed, deliver the one or more cargos to treat that target. Exemplary targets include a cell, a pathogen, an organ (e.g., dermis, vasculature, lymphoid tissue, liver, lung, spleen, kidneys, heart, brain, bone, muscle, etc.), a cellular target (e.g., targets of the subject, such as a human subject, including host tissue, host cytoplasm, host nucleus, etc., in any useful cell, such as e.g., hepatocytes, alveolar epithelial cells, and innate immune cells, etc.); as well as targets for exogenous cells and organisms, such as extracellular and/or intracellular components of a pathogen, e.g., bacteria), a molecular target (e.g., within the subject or the exogenous cell/organism, such as pathogen DNA, host DNA, pathogen RNA, pathogen proteins, surface proteins or carbohydrates of any subject or exogenous cell), etc.

In one instance, the particle is employed to target a host (e.g., a subject), a pathogen, or both (e.g., thereby treating the subject and/or the target). Exemplary pathogens include a bacterium, such as *Bacillus* (e.g., *B. anthracis*), Enterobacteriaceae (e.g., *Salmonella, Escherichia coli, Yersinia pestis, Klebsiella*, and *Shigella*), *Yersinia* (e.g., *Y. pestis* or *Y. enterocolitica*), *Staphylococcus* (e.g., *S. aureus*), *Streptococcus, Gonorrheae, Enterococcus* (e.g., *E. faecalis*), *Listeria* (e.g., *L. monocytogenes*), *Brucella* (e.g., *B. abortus, B. melitensis*, or *B. suis*), *Vibrio* (e.g., *V. cholerae*), *Corynebacterium diphtheria, Pseudomonas* (e.g., *P. pseudomallei* or *P. aeruginosa*), *Burkholderia* (e.g., *B. mallei* or *B. pseudomallei*), *Shigella* (e.g., *S. dysenteriae*), *Rickettsia* (e.g., *R. rickettsii, R. prowazekii*, or *R. typhi*), *Francisella tularensis, Chlamydia psittaci, Coxiella burnetii, Mycoplasma* (e.g., *M. mycoides*), etc.; mycotoxins, mold spores, or bacterial spores such as *Clostridium botulinum* and *C. perfringens*; a virus, including DNA or RNA viruses, such as Adenoviridae (e.g., adenovirus), Arenaviridae (e.g., Machupo virus), Bunyaviridae (e.g., Hantavirus or Rift Valley fever virus), Coronaviridae, Orthomyxoviridae (e.g., influenza viruses), Filoviridae (e.g., Ebola virus and Marburg virus), Flaviviridae (e.g., Japanese encephalitis virus, hepatitis C virus, and Yellow fever virus), Hepadnaviridae (e.g., hepatitis B virus), Herpesviridae (e.g., herpes simplex viruses, herpesvirus, cytomegalovirus, Epstein-Barr virus, or varicella zoster viruses), Papillomaviridae (e.g., papilloma viruses), Papovaviridae (e.g., papilloma viruses), Paramyxoviridae (e.g., respiratory syncytial virus, measles virus, mumps virus, or parainfluenza virus), Parvoviridae, Picornaviridae (e.g., polioviruses and hepatitis A virus), Polyomaviridae, Poxviridae (e.g., variola viruses or vaccinia virus), Reoviridae (e.g., rotaviruses), Retroviridae (e.g., human T cell lymphotropic viruses (HTLV) and human immunodeficiency viruses (HIV)), Rhabdoviridae (e.g., rabies virus), and Togaviridae (e.g., encephalitis viruses, yellow fever virus, and rubella virus)); a protozoon, such as *Cryptosporidium parvum, Encephalitozoa, Plasmodium, Toxoplasma gondii, Acanthamoeba, Entamoeba histolytica, Giardia lamblia, Trichomonas vaginalis, Leishmania*, or *Trypanosoma* (e.g., *T. brucei* and *T. Cruzi*); a helminth, such as cestodes (tapeworms), trematodes (flukes), or nematodes (roundworms, e.g., *Ascaris lumbricoides, Trichuris trichiura, Necator americanus*, or *Ancylostoma duodenale*); a parasite (e.g., any protozoa or helminths described herein); or a fungus, such as Aspergilli, Candidae, *Coccidioides immitis*, and Cryptococci. Other pathogens include a multidrug resistant (MDR) pathogen, such as MDR forms of any pathogen described herein. Additional pathogens are described in Cello J et al., *Science* 2002; 297:1016-8; Gibson D G et al., *Science* 2010; 329:52-6; Jackson R J et al., *J. Virol.* 2001; 75:1205-10; Russell C A et al., *Science* 2012; 336:1541-7; Tumpey T M et al., *Science* 2005; 310:

77-80; and Weber N D et al., *Virology* 2014; 454-455:353-61, each of which is incorporated herein by reference in its entirety.

The present invention can be employed to treat an infection (e.g., a viral infection). Exemplary infections include an encephalitis infection, a viral infection, a bacterial infection, etc. Infections can arise from a virus, such as a mosquito-borne viral pathogen, an encephalitis virus (e.g., Venezuelan equine encephalitis virus (VEEV)), herpes virus (e.g., herpes simplex virus, varicella-zoster virus, and Epstein-Barr virus), rabies virus, poliovirus, measles virus, an arbovirus (e.g., St. Louis encephalitis virus and West Nile encephalitis virus), bunyavirus (e.g., La Crosse strain, California encephalitis virus, etc.), arenavirus (e.g., lymphocytic choriomeningitis virus), reovirus (e.g., Colorado tick virus), henipavirus, flavivirus (e.g., Japanese encephalitis virus (JEV), St. Louis encephalitis virus, etc.), enterovirus, and Powassan virus. Alternatively, the infection can arise from bacteria, fungi, and/or protozoa.

Compositions and Formulations

The present lipid-coated particles can be formulated in any useful manner. For instance, the formulation can be optimized for subcutaneous (SC), intranasal (IN), aerosol, intravenous (IV), intramuscular (IM), intraperitoneal (IP), oral, topical, transdermal, or retro-orbital delivery. Any useful dosages can be employed within the formulations. Exemplary dosages include, e.g., 200 mg/kg. The formulation or composition can include a plurality of particles (e.g., an effective amount thereof) and an optional pharmaceutically acceptable excipient (e.g., any described herein).

In some instances, the pharmaceutical composition includes a population of particles (e.g., any described herein) in an amount effective for modulating or modifying a target gene within a subject in combination with a pharmaceutically acceptable carrier, additive, or excipient. In other instances, the composition further includes a drug, a therapeutic agent, etc., which is not disposed as cargo within the particle.

The composition can be formulated in any useful manner with a plurality of particles. Such formulations can be included with any useful medium, excipient (e.g., lactose, saccharide, carbohydrate, mannitol, leucine, PEG, trehalose, etc.), additive, propellant, solution (e.g., aqueous solution, such as a buffer), additive, preservative, carrier (e.g., aqueous saline, aqueous dextrose, glycerol, or ethanol), binder (e.g., saccharide, cellulose preparation, starch paste, or methyl cellulose), filler, or disintegrator.

Pharmaceutical compositions according to the present invention include an effective population of lipid-coated particles herein formulated to effect an intended result (e.g., immunogenic result, therapeutic result and/or diagnostic analysis, including the monitoring of therapy) formulated in combination with a pharmaceutically acceptable carrier, additive or excipient. The particles within the population of the composition may be the same or different depending upon the desired result to be obtained. Pharmaceutical compositions according to the present invention may also comprise an addition bioactive agent or drug, such as an antibiotic or antiviral agent.

Formulations and compositions containing the particles according to the present invention may take the form of liquid, solid, semi-solid or lyophilized powder forms, such as, for example, solutions, suspensions, emulsions, sustained-release formulations, tablets, capsules, powders, suppositories, creams, ointments, lotions, aerosols, patches or the like, preferably in unit dosage forms suitable for simple administration of precise dosages.

Methods for preparing such dosage forms are known or apparent to those skilled in the art; for example, see Remington's Pharmaceutical Sciences (17th Ed., Mack Pub. Co., 1985). The composition to be administered will contain a quantity of the selected compound in a pharmaceutically effective amount for therapeutic use in a biological system, including a patient or subject according to the present invention.

EXAMPLES

Example 1: Lipid-Coated Mesoporous Silica Nanoparticle Technology for the Delivery of the ML336 Antiviral to Inhibit Encephalitic Alphavirus Infection New World alphaviruses affect North, South, and Central America and pose a major public health threat as they are highly infectious and can result in fatal encephalitis in humans [1-3]. One of these alphaviruses, the Venezuelan Equine Encephalitis Virus (VEEV), is classified as a Category B Agent by the CDC and NIAID due to its amenability to aerosolization while remaining highly infectious and the lack of controlled vaccines and antivirals against the virus [3]. Because of its potentially debilitating health consequences, low infectious dose in humans, and stability in storage, VEEV is a potential bioterrorism agent and has been previously stockpiled in the US and USSR [2, 3].

In addition to its use as a bioterrorism agent, natural VEEV outbreaks result in equine and human infections in North and South America, causing high rates of fatality in equines (85%) and chronic neurological complications in humans [3-5]. Infected humans experience influenza-like symptoms, and 14% of infections result in neurological complications and sequelae, including disorientation, ataxia, depression, and convulsions [2, 5]. In one percent of cases, human infections result in mortality [4, 5]. Thus, developing strategies to inhibit VEEV infection is critical to minimizing fatalities and complications in cases of bioterrorism and natural outbreaks. For all these reasons, VEEV poses a major public health risk due to its amenability to use as a bioterrorism agent and its severe health consequences in humans and equines.

Several small molecule drugs have been developed that inhibit VEEV, but many are limited by high toxicity or low efficacy [6-11]. Recently, a highly effective small molecule inhibitor of VEEV was developed with the assistance of a high throughput, cell-based screen [4, 6]. Referred to as ML336, this molecule was found to have a $EC_{90}$ of 170 nM against a VEEV vaccine strain (TC-83) and reduce viral titer by 630,000-fold at nanomolar concentrations. In addition, intraperitoneal administration of ML336 to mice infected with TC-83 resulted in a 71% survival rate as compared to the 14% survival rate observed in untreated mice. While the potency of this drug at nanomolar concentrations and in in vivo studies is encouraging, ML336 has limited solubility (0.04 mg/mL in PBS, pH 7.4) and limited stability (reduction of 17% and 35% of drug in PBS and mouse plasma, respectively, after 3 hours) in aqueous solutions [4], potentially reducing its effectiveness.

Thus, ML336 is a recently developed small molecule inhibitor of VEEV, shown to effectively reduce VEEV strain TC-83 both in vitro and in vivo, but its limited solubility and stability could hinder its use in future applications. To improve drug solubility and stability, we investigated utilizing a nanoparticle based platform to deliver ML336 for VEEV inhibition both in vitro and in vivo. In particular, lipid-coated mesoporous silica nanoparticles (LC-MSNs) were employed. The large surface area of the MSN core promotes hydrophobic drug loading, while the liposome coating enables enhanced circulation time and biocompatibility, thereby providing a platform for ML336 delivery.

Mesoporous silica nanoparticles (MSNs) have been used in drug delivery systems to improve drug stability and solubility, protect cargo, target specific tissues, and enhance drug circulation time and controlled release [12, 13]. MSNs have a narrow size distribution and can be optimized for various drug delivery applications by tuning particle size, pore size, surface properties, and the porous structure [14, 15]. Established methods enable formation of MSNs with uniform and tunable pore size, endowing MSNs with a large and uniform surface area for drug adsorption (600-1000 $m^2/g$) [12-15]. This property is particularly advantageous for loading water insoluble or unstable drugs, as the large surface area acts as a reservoir for hydrophobic drug in aqueous solution and can improve drug efficacy in vivo [16, 17]. In addition, MSNs are stable in non-aqueous solutions and permit loading of hydrophobic drugs in organic solvents, giving them a distinct advantage over polymeric or liposomal nanoparticle delivery systems [18].

While MSNs are a promising carrier for ML336, drug-loaded MSNs can have low colloidal stability and are subject to aggregation in physiological solutions, reducing circulation time and preventing desirable cell uptake [19, 20]. In addition, premature release of cargo from MSNs can be problematic [21]. In order to overcome these challenges, we investigated the application of a lipid-based coating to the exterior of ML336-loaded MSNs.

MSNs coated with supported lipid bilayers (lipid-coated MSNs (LC-MSNs)) have been employed in drug and protein delivery applications to improve colloidal stability and subsequent circulation time, biocompatibility, cargo loading and release, and tissue-specific targeting [19, 21-23]. The application of a supported lipid bilayer to the exterior of the MSN (essentially encapsulating the MSN with a liposome) can improve colloidal stability in physiological solutions [19, 20] and prevent cargo release prior to cell internalization or some other external trigger [21]. In addition, a lipid bilayer coating offers an additional surface that can be functionalized independently of the MSN surface for tissue-specific targeting [19, 21, 22, 24]. Finally, the inherent instability and broad size distribution of liposomes can be overcome when combined with MSNs to form LC-MSNs [21, 22, 25]. Thus, LC-MSNs harness the advantages and overcome the obstacles associated with MSNs and liposomes in one versatile platform for small molecule delivery.

Figure 2A:
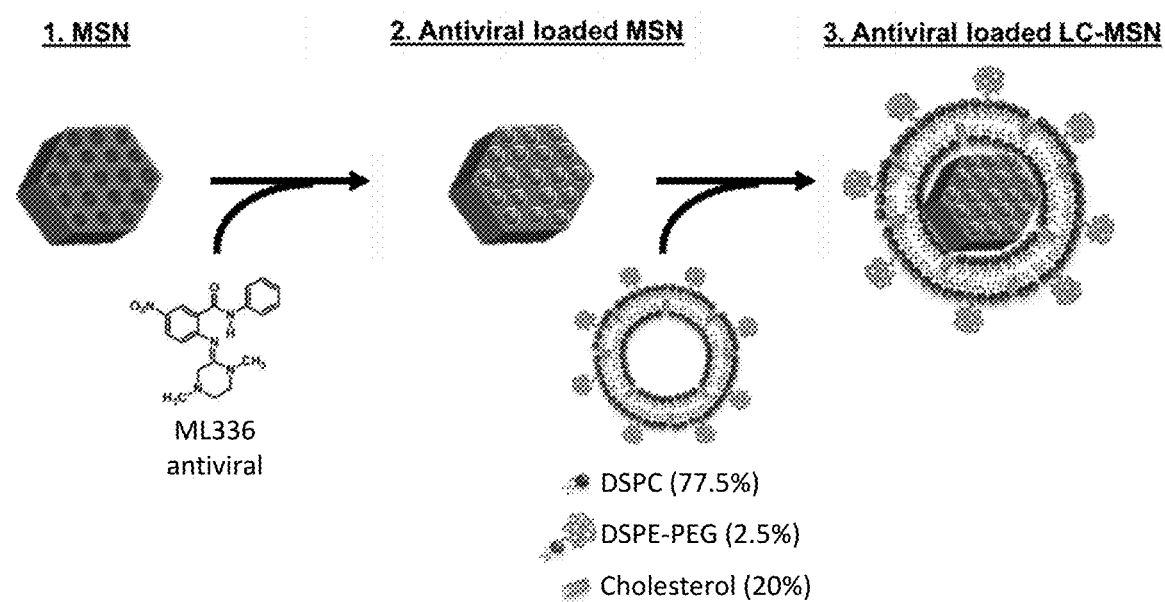
FIG. 2A-2B shows (A) a schematic of ML336 loaded LC-MSN fabrication. The antiviral ML336 was incubated overnight at 4° C. with MSNs at a 10% mass ratio. Liposomes, prepared by combining 77.5% DSPC:2.5% DSPEPEG200:20% cholesterol at mole ratios, were fused to ML336 loaded MSN cores under bath sonication at a 5:1 mass ratio of liposomes:nanoparticles to form ML336 loaded LC-MSNs. Also provided is a schematic (B) of formula (I) and (II) for an exemplary class of quinazolinone-based inhibitors.
Figure 2B:
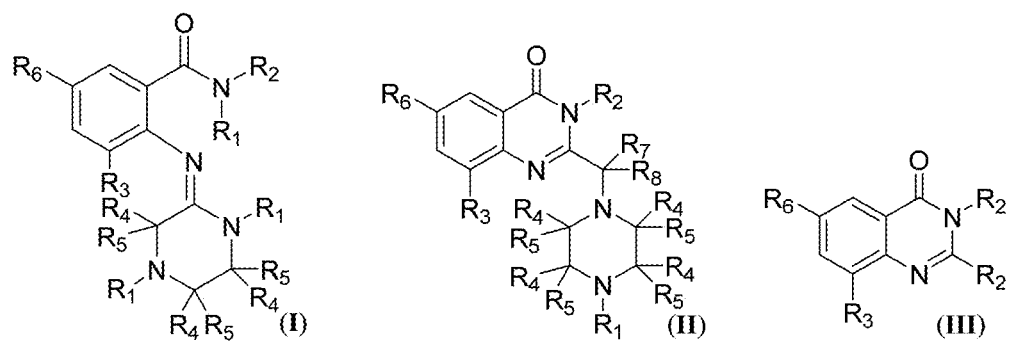

Here, we highlight the use of LC-MSNs for ML336 delivery to inhibit VEEV (see, e.g., FIG. 2). LC-MSN characterization revealed uniformly sized particles coated with a lipid bilayer and good colloidal stability, as assessed by dynamic light scatter analysis, zeta potential measurements, and cryogenic electron microscopy. The delivery vehicle was able to load and release ML336 in a manner that inhibited virus in vitro. In particular, LC-MSNs were found to load 20±3.4 μg ML336/mg LC-MSN and to release 6.6±1.3 μg/mg over the course of 24 hours. ML336-loaded LC-MSNs inhibited VEEV in vitro in a dose-dependent manner and by about 4-6 orders of magnitude as compared to untreated controls. In addition, in vitro studies suggested that additional release of ML336 occurs after cellular internalization, in which studies suggest that this was mediated through a clathrin-mediated endocytosis pathway.

Finally, ML336 loaded LC-MSNs showed viral inhibition in an in vivo murine model of VEEV infection. In vivo safety studies in $C_3H/HeN$ mice shows that LC-MSNs were not toxic when dosed at 0.11 mg LC-MSNs/kg daily for four days. In addition, ML336-loaded LC-MSNs showed significant reduction in brain viral titer in VEEV TC-83 infected mice as compared to PBS treated controls. Overall, to our knowledge, this work demonstrates the first use of a nanoparticle-based system for the delivery of ML336. The successful inhibition of virus achieved with this platform could have widespread benefit in combatting VEEV and other viral infections resulting from bioterrorism or natural causes. Additional details follow.

Example 2: Materials and Methods

The following provide exemplary materials and methods employed for data described herein.

MSN fabrication and characterization: Both small and large batch syntheses of monosized hexagonally-structured MSNs were prepared as previously described [19,41,42] with modifications. MSNs (up-scaled batch of hexagonal small pore particles) were synthesized in a large batch format by dissolving 1.45 g of cetyl trimethylammonium bromide (CTAB) (Sigma) in 750 mL of a 0.32 M aqueous ammonium hydroxide solution in a parafilm covered beaker (1L). The beaker was placed in a 50° C. silicon oil bath for 2 hr (hours) with continuously stirring at high speed (650 rpm). A tetraethyl orthosilicate (TEOS) solution, prepared at 0.88M by combining 3 mL of TEOS (Sigma) with 12 mL of 100% ethanol, was subsequently added to the CTAB surfactant solution. The reaction was stirred vigorously for 1 hr uncovered and then incubated overnight (~18 hrs) in a 50° C. silicone oil bath without stirring. The remaining volume was transferred to a 500 mL glass bottle for an overnight hydrothermal treatment at 70° C. The MSN solution was aliquoted into eight 50 mL tubes and centrifuged at 50K×g for 15 minutes (min). The pellets were resuspended, washed twice with 100% ethanol, and combined into 4 tubes for a second wash. After washing, CTAB removal was achieved by resuspending particles in 100 mL of 6 g/L ammonium nitrate in ethanol. Tubes were placed in a 60° C. bath with sonication for 1.5 hr or at 40° C. with sonication for 30 min. Particles were collected by centrifugation, washed with ethanol (with 90% ethanol and then 100% ethanol; or with 95% ethanol), collected by centrifugation, resuspended in 100 mL of a 1% HCl in ethanol solution, and sonicated for 1.5 hr at 60° C. or twice for 30 min at 40° C. Particles were once again collected by centrifugation, washed with 90% ethanol and then by 100% ethanol, collected by centrifugation and resuspended in 40 mL of 100% ethanol. The MSN suspension was passed through a 1 μm filter to remove large aggregates and weighed after particle desiccation. Size and zeta potential were measured using a Zetasizer instrument (Malvern).

Fluorescently labeled (Cy3) nanoparticles were synthesized in a small scale format by dissolving 250 mg of CTAB in 150 mL of 0.32 M ammonium hydroxide solution in a 250 ml beaker. The reaction was covered with parafilm and heated to 50° C. in a silicone oil bath for 1 hr with continuously stirring at high speed (650 rpm). A Cy3 dye solution was prepared by dissolving 3 mg of Cy3-NHS (ThermoFisher) in 1 ml of 100% ethanol using sonication, followed by the addition of 2.5 μL of APTES (Sigma). The Cy3 solution was allowed to incubate at room temperature without light for 1 hr. A TEOS solution composed of 3 ml of 0.88 M TEOS, was combined with the Cy3-APTES solution, and then added to the CTAB solution and stirred uncovered at 50° C. After 1 hr, the solution was left overnight (~18 hr)

in the 50° C. oil bath without stirring. The remaining volume was transferred to a 100 mL glass bottle for an overnight hydrothermal treatment at 70° C. All centrifugation steps were carried out at 50,000×g for 15 min. The MSN solution was collected by centrifugation and particles were washed twice with 100% ethanol.

CTAB removal was carried out by resuspending particles in 20 mL of a 6 g/L ammonium nitrite in ethanol, and sonicated at 40° C. for 20 min. Particles were collected by centrifugation, washed with 95% ethanol, collected by centrifugation, resuspended in 20 mL of an ethanolic HCl solution (1%) and sonicated twice for 20 min at 40° C. Cy3-labelled particles were washed with 90% ethanol followed by 100% ethanol, collected by centrifugation and resuspended in 12 mL of 100% ethanol.

Prior to use, all MSN suspensions were passed through a 1 µm filter to remove any eventual large aggregates. Quantification was carried out by weight after desiccation of three 500 µL aliquots. Size and zeta potential were measured using a Zetasizer instrument (Malvern Instruments, Ltd). Morphology was assessed with TEM (JEOL 2010). For porosimetry measurements nitrogen sorption data was collected at 77 K with a Quantachrome AutoSorb-iQ2 sorption analyzer, after degassing the samples under vacuum at 333 K. Surface areas were determined using the Brunauer-Emmett-Teller (BET) model. Non-Local Density Functional Theory (NLDFT) was used to calculate pore size distributions and surface areas assuming the surface to be silica with cylindrical pores. Pore size distributions were also calculated according to the Barrett Joyner Halenda (BJH) method. The SEM analysis was carried out using a probe-corrected Hitachi HF5000 TEM/STEM at 200 kV in STEM mode. The STEM unit is equipped with a secondary electron (SE) detector in addition to the annular dark field (ADF), annular bright field (ABF) and bright field (BF) detectors, which allow simultaneous secondary and transmitted election imaging to obtain information from the surface (SE) and bulk (ADF and BF) of the nanomaterial.

LC-MSN fabrication and characterization: Liposomes were prepared by combining 77.5 mol % 1,2-distearoyl-sn-glycero-3-phosphocholine (DSPC), 20 mol % cholesterol, and 2.5 mol % 1,2-distearoyl-sn-glycero-3-phosphoethanolamine-N-[methoxy(polyethylene glycol)-2000] (DSPE-PEG2000) (Avanti Polar Lipids) in chloroform at a 5 mg/mL concentration. Lipid films were prepared using a rotary evaporator (Buchi Corp.), incubated under vacuum overnight, and rehydrated at a 5 mg/mL concentration in a 0.5×PBS (Gibco/Life Technologies), 4 mM $MgCl_2$ solution for 30 minutes at 55° C. The lipid solution was purged with nitrogen for two minutes and then dispersed with an ultrasonication probe (Branson Sonifier, Emerson US). Lipids were sonicated under nitrogen at 10-12 watts for 4 min, followed by a 2 min rest period, repeated twice. Lipids were centrifuged at 16,000 RCF for 20 min to remove any debris deposited into the lipid solution from the sonication probe.

Loaded LC-MSNs were prepared by resuspending 1 mg MSNs in 10 µL water followed by overnight incubation at 4° C. in 100 µl of 1 mg/mL ML336 (Caymen Chemicals) in dimethyl sulfoxide (DMSO) (100 µL DMSO for unloaded LC-MSN groups). To form LC-MSNs, the resulting liposomes were combined with MSNs under bath sonication while pipetting at a 5:1 mass ratio of liposomes:nanoparticles. Particles were then centrifuged at 21,000 RCF to remove liposomes that were not fused with MSNs. When used immediately, resulting LC-MSNs were rinsed twice by resuspending in 1 mL PBS, centrifuging at 21,000 RCF, and removing supernatant. For storing LC-MSNs, particles were rinsed once in PBS and then resuspended in a 9 wt % sucrose solution in PBS, flash frozen in liquid nitrogen, and stored at −80° C. Prior to use (e.g. cryo-EM analysis and all in vitro and in vivo studies), particles were thawed and rinsed once in PBS. For animal studies with viral infection, LC-MSNs were prepared in 2 mg aliquots, combined, and redistributed into 1 or 1.5 mg aliquots before freezing for storage.

Dynamic light scattering (DLS) for particle hydrodynamic diameter and polydispersity index (PDI), and zeta potential measurements were obtained using a Malvern Zetasizer. For cryo-EM analysis, unloaded and loaded LC-MSNs were vitrified using Vitrobot (Thermo Fisher Scientific) as previously described [43]. Briefly, 3 µL of particles suspension was placed on a C-flat grid (Protochips, Inc.) with 2 µm diameter holes, blotted with filter paper, and plunged into liquid ethane for flash freezing. Frozen grids were stored under liquid nitrogen and were transferred to electron microscope JEM 2200FS (JEOL Ltd). Grids were imaged at 200 keV using DE-20 (Direct Detector Inc.) direct electron detector camera. The 2200FS microscope had Field Emission electron source and an omega-type electron energy filter to remove inelastically scattered electrons from image formation. The energy selecting slit was set to 20 eV. DE-20 camera was used in "movie" mode with frame rate of 25 frames/s. Off-line frame alignment was performed with DE_process_frames.py script provided by Direct Electron Inc. Images were collected at 40,000× indicated magnification, the pixel size on the specimen scale corresponded to 1.5 Å/pixel. Images were collected with 1.5 to 2.6 µm defocus range. Cryo-EM images were analyzed for lipid bilayer thickness using ImageJ. Fifty particles were analyzed from each of the ML336 loaded LC-MSN and unloaded LC-MSN groups.

Figure 4A:
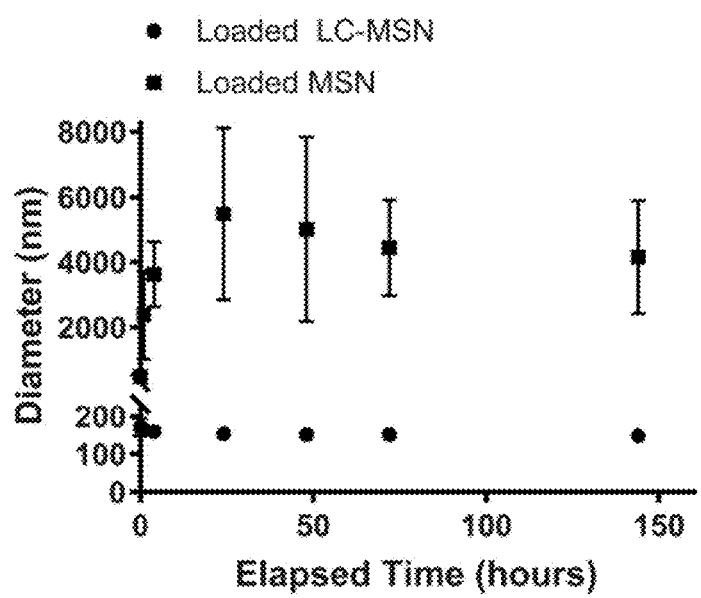

LC-MSN ML336 loading and release studies: The concentration of ML336 was determined by correlating sample (supernatants) spectroscopic absorption measurements at 320 nm (Nanodrop, ThermoFisher Scientific) with ML336 standard curves prepared in the 5 mg/mL liposome solution (described above) or PBS (FIG. 4C). Loading of ML336 in LCMSNs was calculated using the following formula: Total mass loaded=Initial mass of ML336 added −[(mass of ML336 in the supernatant after combination with the lipids)+(mass of ML336 in the supernatant of PBS wash 1)+(mass of ML336 in the supernatant of PBS wash 2)]. A dataset of six replicates highlights further how loading and release was calculated FIG. 4D). Briefly, to determine the mass of ML336 loaded, the mass of ML336 in the supernatant from each wash step (one after lipid application and two in PBS, labeled A, B, and C, respectively, in FIG. 4D) was subtracted from the total mass of ML336 loaded, 100 µg (100 µg−(A+B+C); FIG. 4D). The total loading was then reported on a per mass LC-MSN basis.

For release studies, rinsed LC-MSNs were resuspended in 1 mL of PBS and incubated at room temperature. Release of ML336 was measured by removing 100 µL aliquots from each sample, centrifuging the aliquot at 21,000 RCF, and measuring the concentration of ML336 in the supernatant at 0.25, 0.5, 0.75, 1, 2, 3, 4, 24, and 96 hr timepoints. Cumulative mass released was calculated by averaging the mass observed in each sample at each timepoint. Cumulative percent released was calculated by averaging the percent released for each sample at each timepoint using the following formula: Percent released=100%*(mass released at timepoint X/total mass loaded).

LC-MSN internalization studies: All cells were maintained at 37° C. and 5% $CO_2$. Cells were maintained in Dulbecco's Modified Eagle Medium (DMEM, Gibco/Life Technologies; HeLas) or Minimum Essential Medium α (αMEM, Gibco/Life Technologies; Veros) supplemented with 10 vol % FBS (Hyclone), 10,000 IU/mL penicillin, and 10,000 μg/ml streptomycin (MP Biomedicals).

For endocytosis inhibitor studies with LC-MSNs, HeLa cells were plated overnight in complete medium on 12-well plates for image analysis or flow cytometry. Unless otherwise indicated, all inhibitors were purchased from EMD Millipore. The following inhibitors were initially resuspended in DMSO and were then diluted in complete medium to obtain the final concentrations indicated: the vacuolar Ht ATPase inhibitor bafilomycin A (BAF)(100 nM), the cationic amphiphilic compound chlorpromazine (CPZ; 6.5 μg/ml; Sigma), dynamin 2 inhibitor dynasore (DYN) (80 μM), wortmannin (Wort) (150 ng/ml), p21-activated kinase inhibitor III (IPA-3) (10 μM), and phorbol 12-myristate 13-acetate (PMA) (10 μM). Cells were incubated with inhibitor treatments for 1 h prior and during incubation with Cy3 labeled LC-MSNs, or the pathogens Vesicular Stomatitis virus (VSV strain Indiana 1) and Rift Valley fever virus (RVFV strain MP-12) used as specificity controls for clathrin-mediated endocytosis and caveola-mediated endocytosis, respectively.

For image analysis studies, the cells were washed at 5 hr post-LC-MSN addition with PBS twice and then subjected to brightfield and fluorescent microscopy.

For flow cytometry experiments, cells were washed with PBS twice at 16 hr post LC-MSN addition or virus infection, then prepared for analysis on a BD Accuri C6 instrument (Becton, Dickerson and Company). Flow cytometry data was analyzed by FCS Express v6 software (De Novo Software).

For confocal microscopy imaging of cellular association with LC-MSNs, HeLa cells were seeded overnight onto No. 1.5 glass cover slips in 6-well plates at a density of $0.75 \times 10^5$ cells per well. Fluorescent LC-MSNs were then added at 25 μg MSN/well for 45 min or 20 hr. After incubation, cells were washed with PBS, fixed with 4% paraformaldehyde in PBS for 15 min with prewarmed solutions followed by overnight storage at 4° C., washed twice with PBS, and made permeable with 0.1% Triton-X in PBS for 15 min. Cells were then blocked with 1% BSA in PBS for 20 min and then labeled with 5 units/1 ml Alexa Fluor 647 phalloidin (ThermoFisher) and Alexa Fluor 488 anti-α-tubulin antibody (Invitrogen) in blocking buffer for 1 hr. After washing with PBS, slides were mounted using Prolong Gold with DAPI (ThermoFisher). Confocal images were acquired with a 63X/1.4NA oil objective in sequential scanning mode using a Leica TCS SP8 confocal microscope. Three-dimensional cell images were isosurface rendered using the Leica Application Suite Advanced Fluorescence 3D analysis software.

In vitro viral inhibition: All cells were maintained at 37° C. and 5% $CO_2$. Cells were maintained in Dulbecco's Modified Eagle Medium (DMEM, Gibco/Life Technologies; HeLas) or Minimum Essential Medium α (αMEM, Gibco/Life Technologies; Veros) supplemented with 10 vol % FBS (Hyclone), 10,000 IU/mL penicillin, and 10,000 μg/ml streptomycin (MP Biomedicals).

The TC-83 virus was obtained through the NIH Biodefense and Emerging Infections Research Resources Repository, NIAID, NIH (NR-63), and was propagated in Vero cells. Cells were infected at a multiplicities of infection (MOI) of 0.1 and cultured for two days. Supernatant was collected and the concentration of plaque forming units (PFUs) was determined using a standard plaque assay with an agarose overlay (1:1 2× Modified Eagle Medium (Gibco/Life Technologies; 8 vol % FBS, 10,000 IU/mL penicillin, and 10,000 μg/ml streptomycin):1.5 wt % agarose (Invitrogen)). Cells were fixed and stained with an ethanol-based crystal violet solution (0.14 wt % crystal violet (Sigma-Aldrich), 21 vol % ethanol) and plaques were counted manually to determine PFU/mL.

HeLa cells at 80-90% confluency in 12 well plates were pretreated with 25 μg LC-MSNs in 100 μL Opti-MEM Reduced Serum Media (Gibco/Life Technologies) for 1 hr, then infected with TC-83 at 0.1 MOI for 30-60 min. Virus was then removed, cells were rinsed three times in PBS, and treatments were added back for the remainder of the time course in 1 mL DMEM. Supernatants were taken at 24, 48, and 72 hrs. Phase images were taken at the same timepoints using an inverted microscope (Olympus-IX70).

For experiments with pre-released LC-MSNs, LC-MSNs were incubated in Opti-MEM at a concentration of 2.5 μg/mL for 4 hrs at room temperature. LC-MSNs were then centrifuged at 20,000 RCF, and supernatant was collected. Particles were resuspended at 2.5 μg/mL in Opti-MEM and immediately added to cell cultures as described above. The supernatant of 25 μg of particles (100 μL) was also immediately added to cells.

The concentration of PFUs in supernatants was determined using a standard plaque assay on VERO cells in 12 well plates as described above. Serial dilutions of supernatants were prepared in αMEM and used to infect cells for 30-60 min. Due to the minimum concentration of virions in supernatants required for detection in plaque assays, the limit of detection (indicated on each graph) was 100 PFU/mL.

In vivo viral inhibition: All animal work was conducted in accordance with protocols approved by the Lawrence Livermore National Laboratory Institution Animal Care and Use Committee. For safety studies, five 6-8 week old $C_3$H/HeN mice were injected intraperitoneal (IP) with 1 mg LC-MSNs in 200 μL PBS, and three mice were injected with 200 μL PBS only. Mice were monitored for 15 days and weighed on days 3, 6, 9, and 15. At day 15, animals were euthanized; and lungs, livers, spleens, kidneys, and brains were dissected from three animals in each group.

An established $C_3$H/HeN mice model of VEEV infection was used to assess the ability of ML336-loaded LC-MSNs to inhibit viral infection [8]. In the first animal study, animals were divided into four groups of ten animals each: ML336 loaded LC-MSNs, unloaded LC-MSNs, free drug, and PBS groups. For ML336 loaded and unloaded LC-MSNs groups, 1 mg of LC-MSNs was mixed with 200 μL 1 wt % carboxymethylcellulose sodium (Sigma-Aldrich) in PBS. For free drug groups, 20 μL of 1 mg/mL ML336 in DMSO was mixed into 200 μL of 1 wt % carboxymethylcellulose sodium in PBS, resulting in 20 μg ML336 per injection, similar to what is loaded in 1 mg ML336-loaded LC-MSNs. Mice were injected twice a day IP for 4 days. Four hours after the first injection on day 1, the mice were infected with an intranasal instillation of 50 μl of TC-83 containing a total of $10^8$ PFU.

Mice were monitored for weight and clinical signs of disease each day post-infection and assigned a clinical score from 0-4 (mild to severe): 0=bright, alert, responsive and active, animals exhibit normal grooming and social behavior, no loss of appetite; 1=mild clinical signs of infection such as coat ruffling and loss of appetite; 2=pronounced decrease in activity and responsiveness to stimulation, ruffled coat and rapid, shallow breathing, obvious neurological impairment such as trouble ambulating and hunching; 3=moribund, eyes closed completely, labored breathing, no activity and unresponsive to tail tug, or animals that have lost>25% of their body weight, in which mice that met this criterion were euthanized; and 4=found dead.

The second animal study was conducted as described above with the following changes. LC-MSN masses for both loaded and unloaded LC-MSN groups were increased to 1.5 mg. For free drug groups, 15 μL of 2 mg/mL ML336 in DMSO was mixed into 185 μL of 1 wt % carboxymethylcellulose in PBS, resulting in 30 μg ML336 per injection, similar to what is loaded in 1.5 mg ML336-loaded LC-MSNs. On day 5, five mice from each group were euthanized and dissected for brain, spleen, kidney, liver, and serum. Organs were homogenized using disposable tissue grinders, and tissue lysate was assessed for viral load using a standard plaque assay as described above.

Statistical Analysis: All results are depicted as mean±standard deviation. Analysis of Variance (ANOVA) was used to identify significant factors and interactions, then Tukey's post hoc test (significance level p<0.05) was used to generate pairwise comparisons between means of individual sample groups and determine statistical significance (GraphPad Prism 7).

Example 3: ML336 Loaded LC-MSNs

Figure 1C:
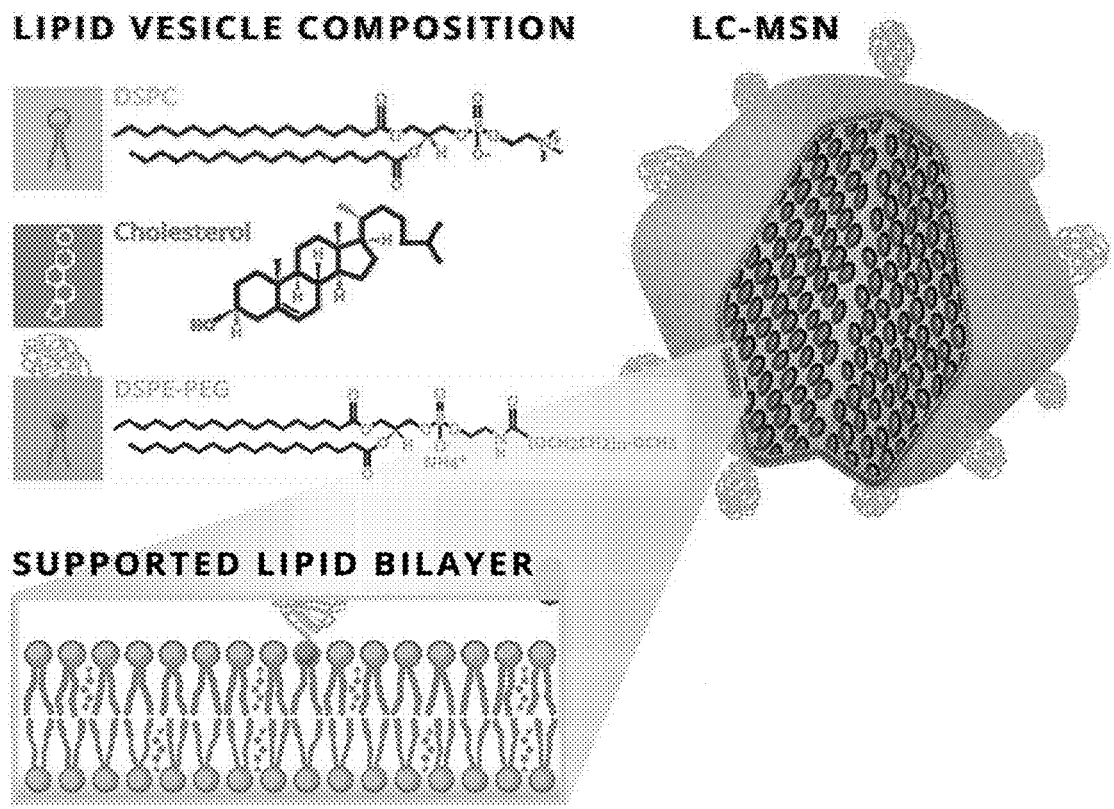

The small molecule ML336 was recently discovered to have antiviral drug properties against VEEV [4]. While proven effective both in vivo and in vitro, it has limited solubility in aqueous solution, necessitating a delivery vehicle to improve drug stability and enable controlled release. Thus, we utilized a hybrid liposome-mesoporous silica nanoparticle technology that takes advantage of the loading capabilities and uniformity of MSNs and the biocompatibility and retention capabilities of liposomes in one drug delivery platform (FIG. 1C) [19, 22, 26, 27]. Referred to as LC-MSNs (see, e.g. [22]), these particles have the potential to protect and control the release of ML336 as well as be modified for tissue-specific targeting in future iterations of the LC-MSN technology [19, 20].

Figure 3A:
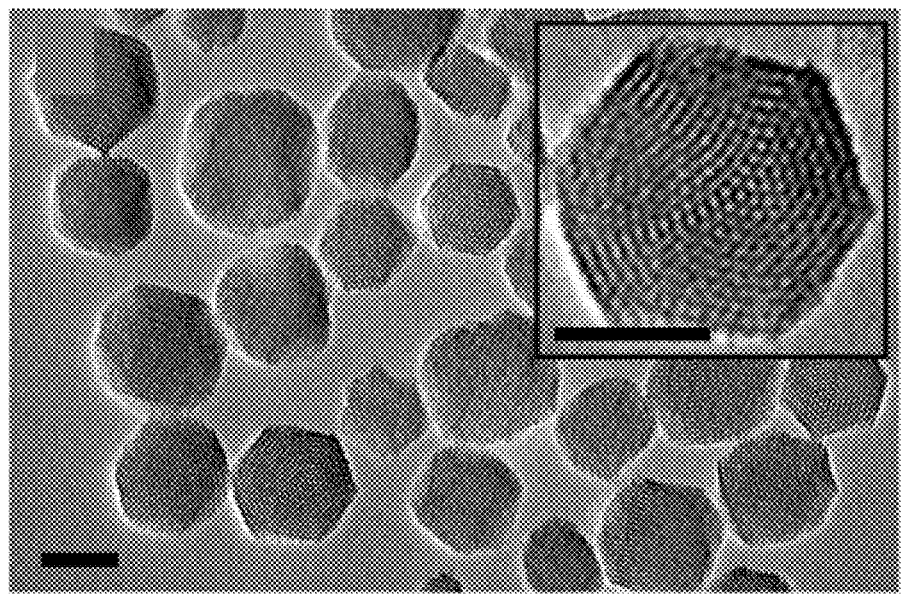
FIG. 3A-3I shows characterization of ML336 LC-MSNs. Provided are (A) TEM images and (B) SEM images of MSNs (all scale bars=50 nm; except (B) bottom left scale bar=100 nm). Also provided are cryo-EM images of (C) ML336 loaded LC-MSNs and (D) unloaded LC-MSNs (scale bar=50 nm). Gray arrows point out examples of the lipid bilayer. Also provided are graphs showing (E) cumulative and (F) percent release (normalized to total ML336 loaded) of ML336 from LC-MSNs. Data represent mean±standard deviation, n=6. Also provided are ultrastructure and pore analysis of mesoporous silica nanoparticles, in which shown are (G,H) SEM images of the hexagonal porous structure of MSNs with different projections. As seen in (G), hexagonal structure is highlighted by the honey comb-like arrangement (A1) and tubular channels (A2). Axis (z) is parallel to the pore's plan. As seen in (H), a tilted image shows tubular channels in a hexagonal arrangement ending by cargo-accessible openings (pore mouth). Provided are (I) graphs of $N_2$ adsorption-desorption isotherm and pore size distribution (inset) for hexagonal small pore MSN.

LC-MSNs formation was modified based on past methods [19, 20]. First, monosized sub-150 nm MSNs were produced by up-scaling previous synthesis protocols. Optimized large batch synthesis procedures yielded highly homogeneous nanoparticles without alteration in structure or size. As shown by transmission electron microscopy (TEM) (FIG. 3A), the nanoparticles of approximately 75 nm were narrow in size distribution and displayed a hexagonal porous structure (FIG. 3A, inset). Their homogeneous colloidal size was also confirmed by DLS (95.9±2.1 nm, PDI=0.07±0.01) (Table 1).

Figure 3B:
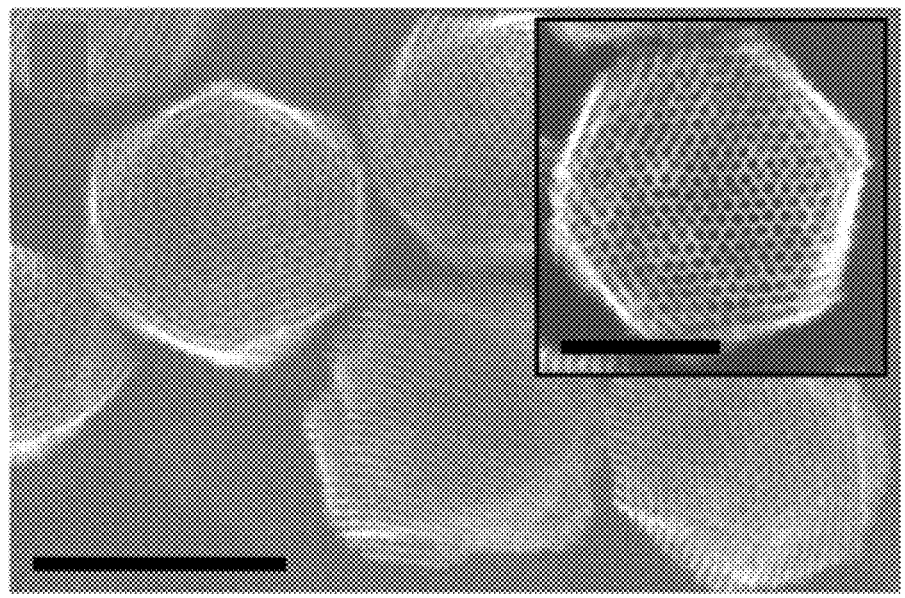

Additionally, scanning electron microscopy (SEM) analysis (FIG. 3B) was performed in order to highlight the 3D hexagonal shape of the MSNs and, importantly, the open porous structure. As demonstrated in FIG. 3B (insert) and FIG. 3G-3I, surface accessible pores were clearly observed. In addition to SEM observation, $N_2$ sorption also provided evidence on the pore shape and its surface accessibility. The resulting isotherm (FIG. 3I) showed a steep increase in adsorption characteristic of a capillary condensation in mesopores capillary evaporation on the desorption branch, supporting the presence of uniform cylindrical mesopore open at both ends (surface-accessible). Accessibility of the pores was indirectly confirmed by the high (BET) accessible surface area found for these MSNs. Furthermore, 100 pore diameters were measured on the SEM micrograph; and their average was found to be 2.65±0.29 nm, which is in the same order of magnitude of the average pore size found by $N_2$ sorption using DFT theory (~3.5 nm) (FIG. 3G-3I).

Liposomes were composed of 77.5:20:2.5 DSPC:Cholestrol:DSPE-PEG(2000) (mol %), a lipid composition chosen to ensure formation of a stable bilayer and to enhance colloidal stability of the resulting LC-MSNs. The primary lipid component, DSPC, was chosen due to its saturated acyl chain, as previous work has indicated that unsaturated lipids may contribute to reduced colloidal stability of LCMSNs over time [19]. Cholesterol was used to improve control over bilayer fluidity and leakage [22, 28], and a pegylated DSPE was included to increase circulation time and reduce protein adsorption to the LC-MSN surface [19, 22, 26, 27]. To assemble LC-MSNs, liposomes were applied to MSNs under sonication at a 5:1 liposomes:MSN (mass ratio), a similar ratio to those used previously (2:1-4:1) to produce high quality LC-MSNs [19]. Fusion between the negatively charged MSN and the zwitterionic liposome occurs due to electrostatic interactions and the lipophilic nature of the MSNs [15, 19, 29, 30].

To ensure successful formation of LC-MSNs, particles were evaluated for size, charge, and morphology. In previous studies, increased particle size upon addition of a lipid bilayer to MSNs has been observed and is indicative of successful bilayer formation [19, 21, 28, 31, 32]. Results were similar in this work, as application of the lipid bilayer increased MSN particle diameter from ~96 nm to ~150 nm and 164 nm for unloaded and ML336 loaded particles, respectively, while maintaining a low PDI and thus good uniformity (Table 1, FIG. 3A-3C).

TABLE 1

Z-average diameter, PDI, and zeta potential for MSNs, liposomes, unloaded LC-MSNs, loaded MSNs, and loaded LC-MSNs

| Particle Type | Medium | Z-average Diameter (nm) | PDI | Zeta Potential (mV) |
|---|---|---|---|---|
| MSN | Water | 95.9 ± 2.1 | 0.072 ± 0.01 | −25.0 ± 0.42 |
| Liposome | 50:50 PBS:Water | 125.03 ± 2.1 | 0.090 ± 0.01 | −0.78 ± 0.20 |
| Unloaded LC-MSN | PBS | 149.5 ± 1.5 | 0.116 ± 0.01 | −0.263 ± 0.41 |
| Loaded MSN | PBS | 487.4 ± 108 | 0.351 ± 0.06 | NA |
| Loaded LC-MSN | PBS | 164 ± 1.5 | 0.144 ± 0.02 | −1.76 ± 0.26 |

A neutralized surface charge of particles is another measure of successful MSN-liposome fusion [31, 33], as a reduction of MSN surface charge is observed due to charge shielding of deprotonated silanols on the MSN surface by the zwitterionic lipid bilayer [19]. Here, uncoated MSNs had zeta potential of −25.0±0.42 mV, similar to what has been reported in literature previously [13, 19, 20], which increased to nearly neutral levels when coated with a lipid bilayer (−0.263±0.41 mV, Table 1).

Figure 3C:
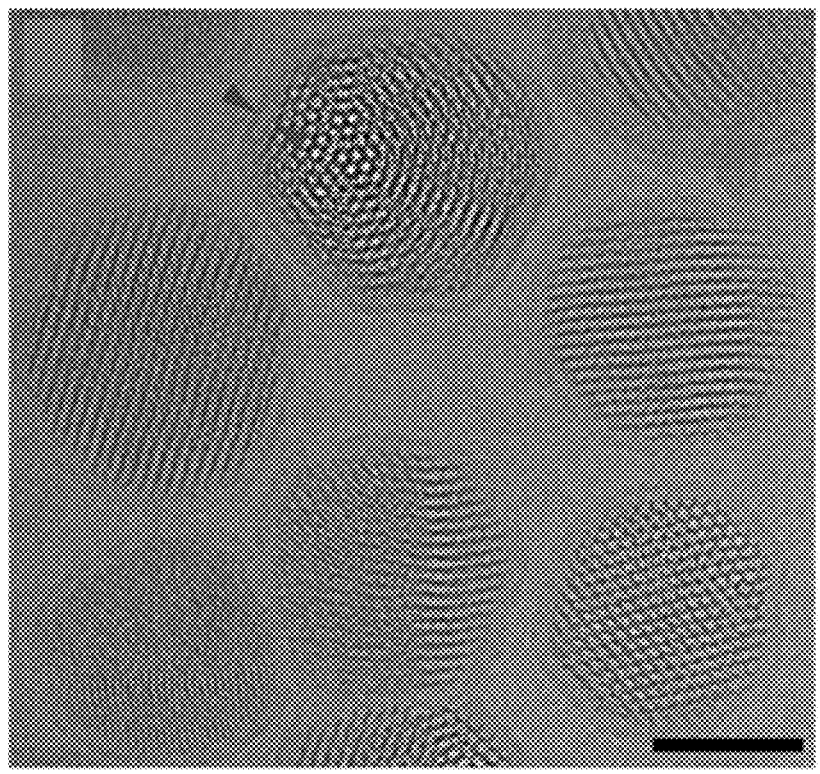
Figure 3D:
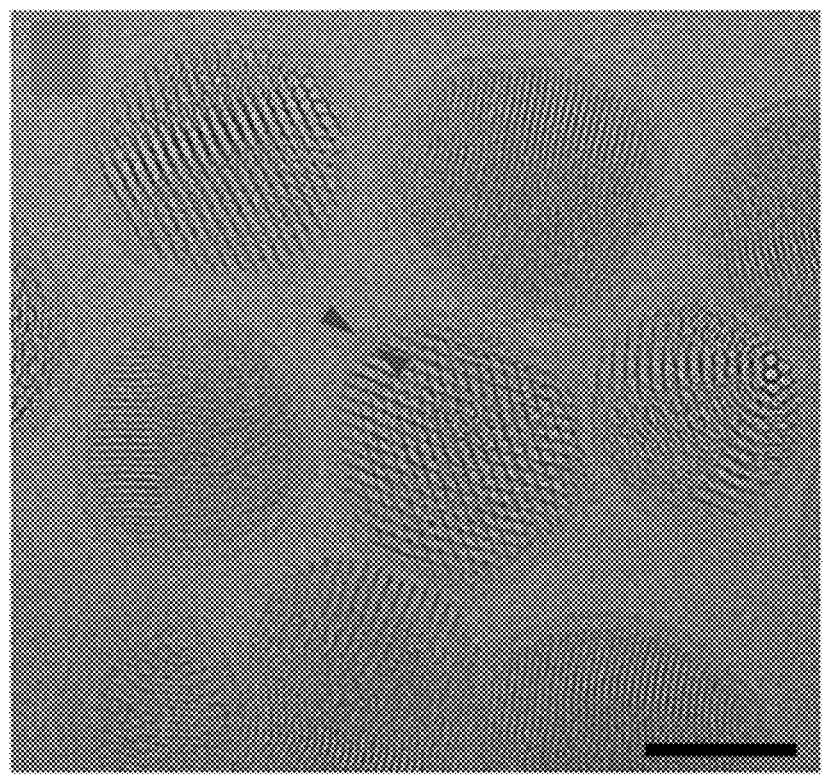

As a final confirmation of successful bilayer application, a uniform lipid bilayer was observed in cryo-EM images (FIG. 3C-3D). Analysis of the cryo-EM images indicated a LC-MSN diameter of 88.1±11.8 nm and 86.5±12.0 nm and a bilayer thickness of 6.0±0.94 nm and 5.4±0.91 nm for loaded and unloaded LC-MSNs, respectively. The smaller diameter of the LC-MSNs determined by cryo-EM compared to DLS is consistent with previous reports [19]. The larger diameter observed in loaded LC-MSNs via DLS size analysis (Table 1) suggests the surface adsorbed ML336 may affect the hydrodynamic radius of the particle due to changes in surface hydrophobicity. Overall, ML336-loaded LC-MSNs were successful fabricated.

While MSNs are highly advantageous for small molecule delivery [12-15], aggregation of MSNs without surface modification or external coatings is commonly observed in high ionic strength physiologically relevant media due to a reduction in the Debye length and correspondingly the degree of electrostatic repulsion [12, 17, 20]. As might be predicted, ML336 loaded MSNs that were not coated with a lipid bilayer aggregated immediately in PBS (Table 1, FIG. 4A). In contrast, loaded LC-MSNs maintained colloidal stability for at least four days (FIG. 4A), indicating their utility in both in vitro and in vivo applications. Taken as a whole, zeta-potential, cryo-EM and stability studies indicate the formation of a complete, conformal and uniform lipid bilayer on ML336 loaded LC-MSNs.

Figure 3E:
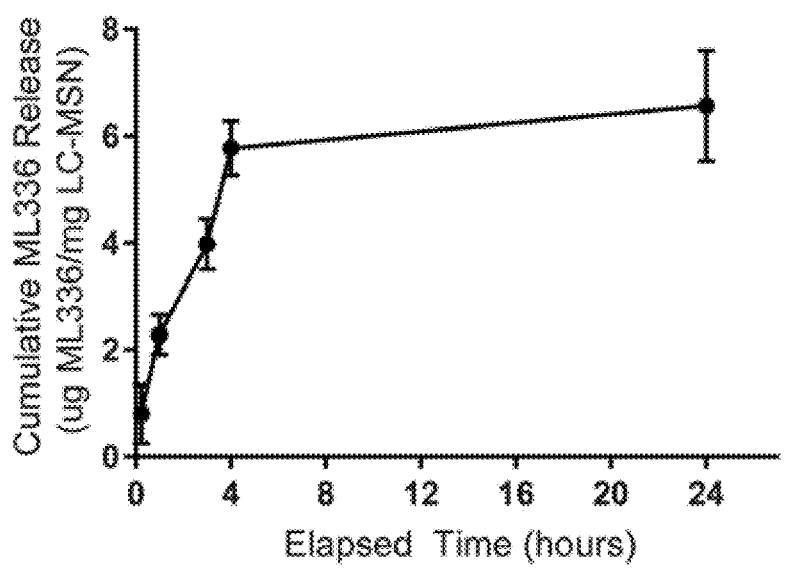
Figure 3F:
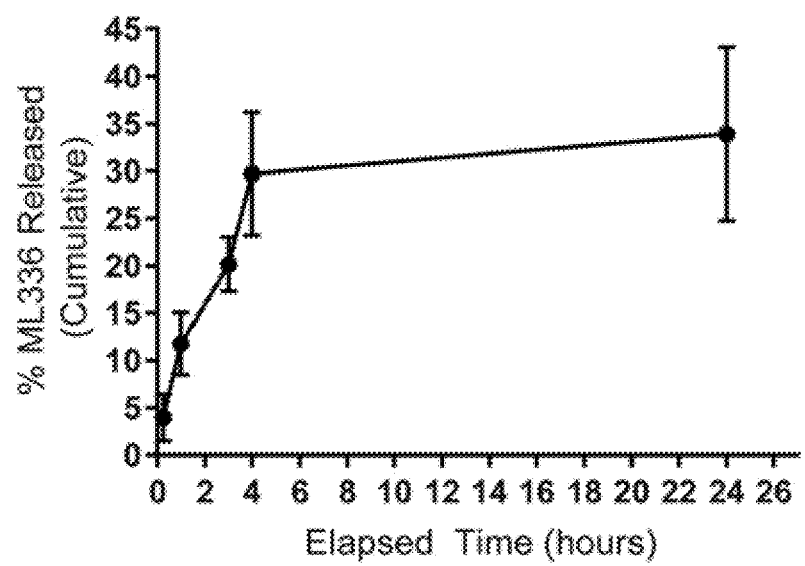
Figure 3G:
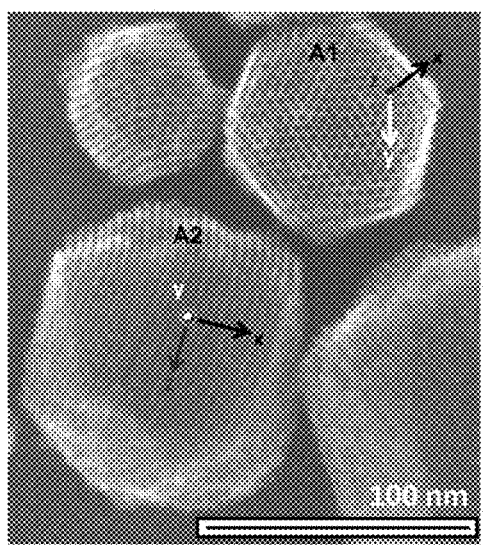
Figure 3H:
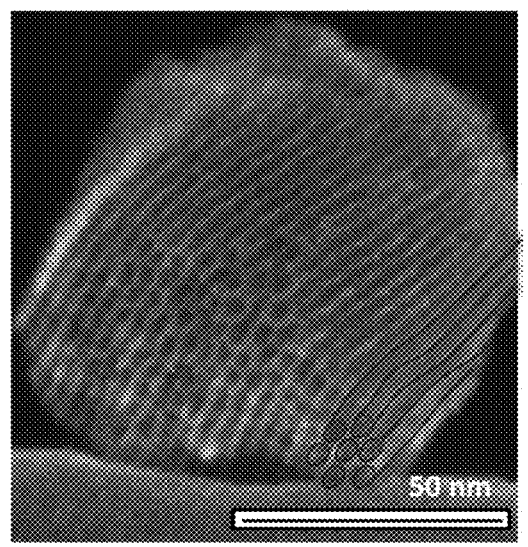
Figure 3I:
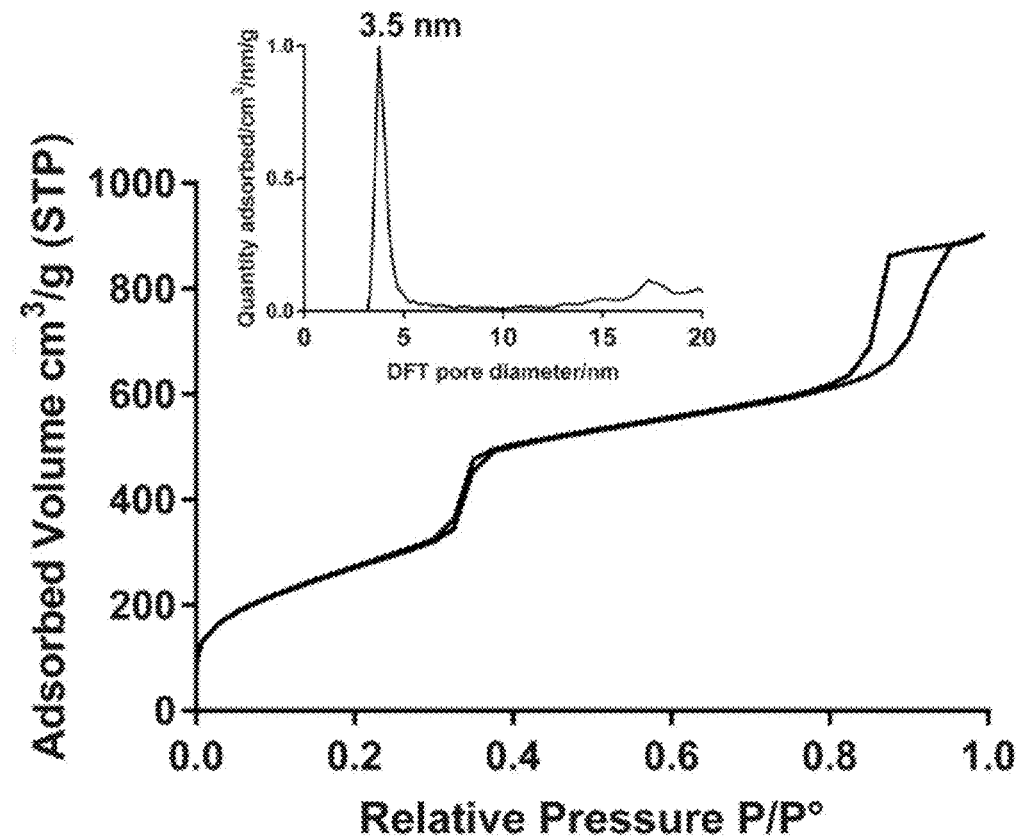

ML336 loading in LC-MSNs was determined to be about 20 µg ML336/mg LC-MSN, as measured by subtracting the amount of ML336 lost in the post-lipid-coating and loading washes from the total mass of ML336 loaded (FIG. 4B-4D). A linear burst release of ML336 was observed to occur in the first 4 hours, with little additional release thereafter (FIG. 3E-3F). Overall, LC-MSNs released about 6.6 µg ML336/ mg LC-MSNs in 24 hours, which correlated to 34% release of ML336 loaded (FIG. 3E-3F; Table 2). No additional release was observed after 4 additional days.

TABLE 2

Summary of ML336 Release from LC-MSNs

| Total ML336 Loaded (µg ML336/mg LC-MSN) | % ML336 Loaded | Total ML336 Released (µg ML336/mg LC-MSN) | % ML336 Released |
|---|---|---|---|
| 20 ± 3.4 | 20 ± 3.4 | 6.6 ± 1.3 | 33.5 ± 6.6 |

Similar release was observed when LC-MSNs were incubated in PBS pH 5, which mimics the intracellular endosome, while about 100% release was observed when LC-MSNs were incubated in methanol. The ML336 release observed here was similar to small molecule release from lipid coated MSNs in previous studies, where 0-35% release of loaded cargo was observed in ~10 hrs at pH 7 for several different lipid bilayer compositions [19, 21, 31-33]. When the pH was dropped to 5, no additional release was observed, confirming what has been observed for a similar lipid bilayer composition previously [19]. In other reports where additional and sometimes nearly complete release of cargo from lipid-coated MSNs has been reported at low pH [32,33], specific acid-sensitive lipids have been employed to promote cargo release under acidic conditions. While still under investigation, the technology presented here could be modified to be acid-sensitive by adjusting the lipid composition of the lipid bilayer. However, the limited release at low pH observed in these studies could be beneficial, as it minimizes premature release and degradation of cargo in the endosomal compartment.

Figure 4E:
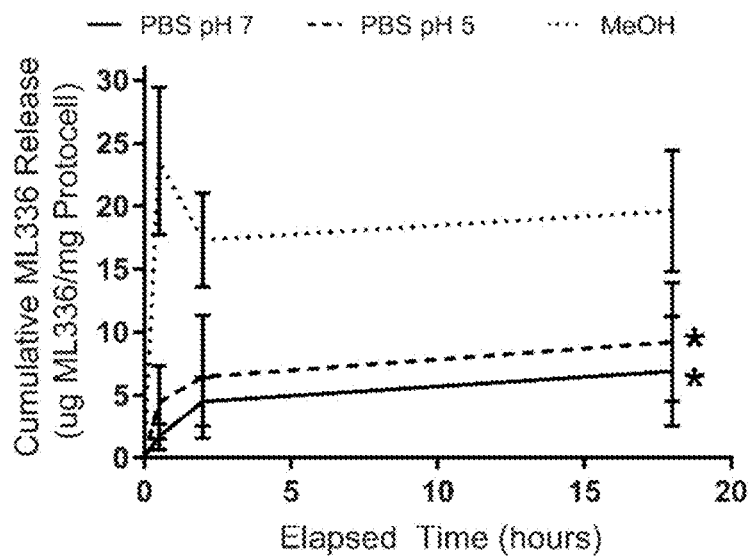
Figure 4F:
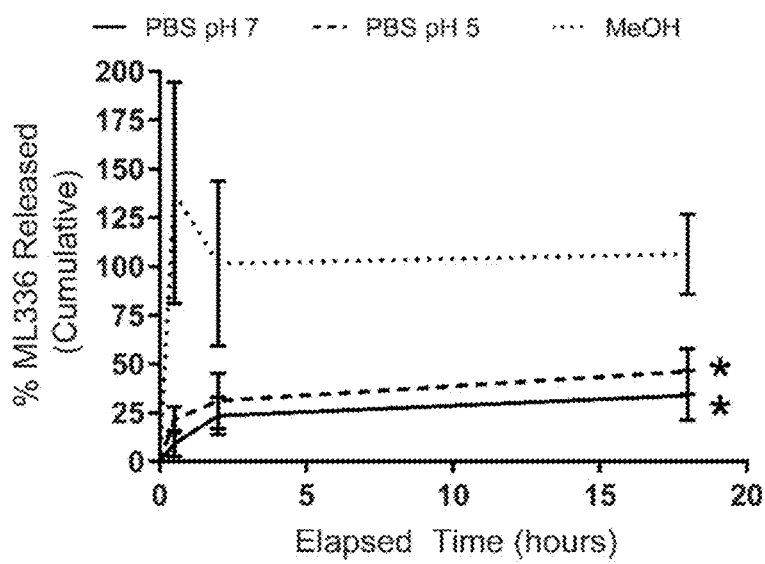

Complete ML336 release was observed when LC-MSNs were incubated in methanol, which is expected to disrupt the lipid bilayer and effectively extract ML336 from the MSN (FIG. 4E-4F). This result suggests that the limited solubility of ML336 in aqueous solution could prevent its release from the MSN core even after the expected disruption of the lipid bilayer at pH 5 [33]. Previously, MSNs loaded with hydrophobic drugs have shown reduced wettability, possibly retarding or preventing drug release prior to self-erosion of the silica matrix [33]. As degradation of the silica matrix is highly dependent upon surface functionalization, loaded cargo, relative concentration of particles, and the surrounding environment [34, 35], cargo release from LC-MSNs will be dependent upon specific conditions in both in vitro and in vivo environments.

To enhance loading and release in future iterations of this technology, the MSN surface could be modified to optimize interactions between the MSN and ML336 [14, 15, 36]. The hydrophobicity of ML336 requires loading in a non-polar solvent (DMSO was used in these studies), while release occurs in physiological conditions (buffered aqueous solutions). As different properties dictate the interactions between ML336 and MSNs in aqueous versus non-aqueous solvents, it may be possible to maximize MSN-ML336 interactions in DMSO to enhance loading while minimizing MSN-ML336 interactions in PBS (or other aqueous solutions) to enhance release [36]. Overall, the results presented here indicate successful loading and release of ML336 from uniform LC-MSNs of high colloidal stability, providing an excellent prototype for future optimization and additional analysis in in vitro and in vivo studies.

Example 4: ML336 Loaded LC MSN Viral Inhibition In Vitro

Figures 5A, 5B, 5C, 5D, 6:
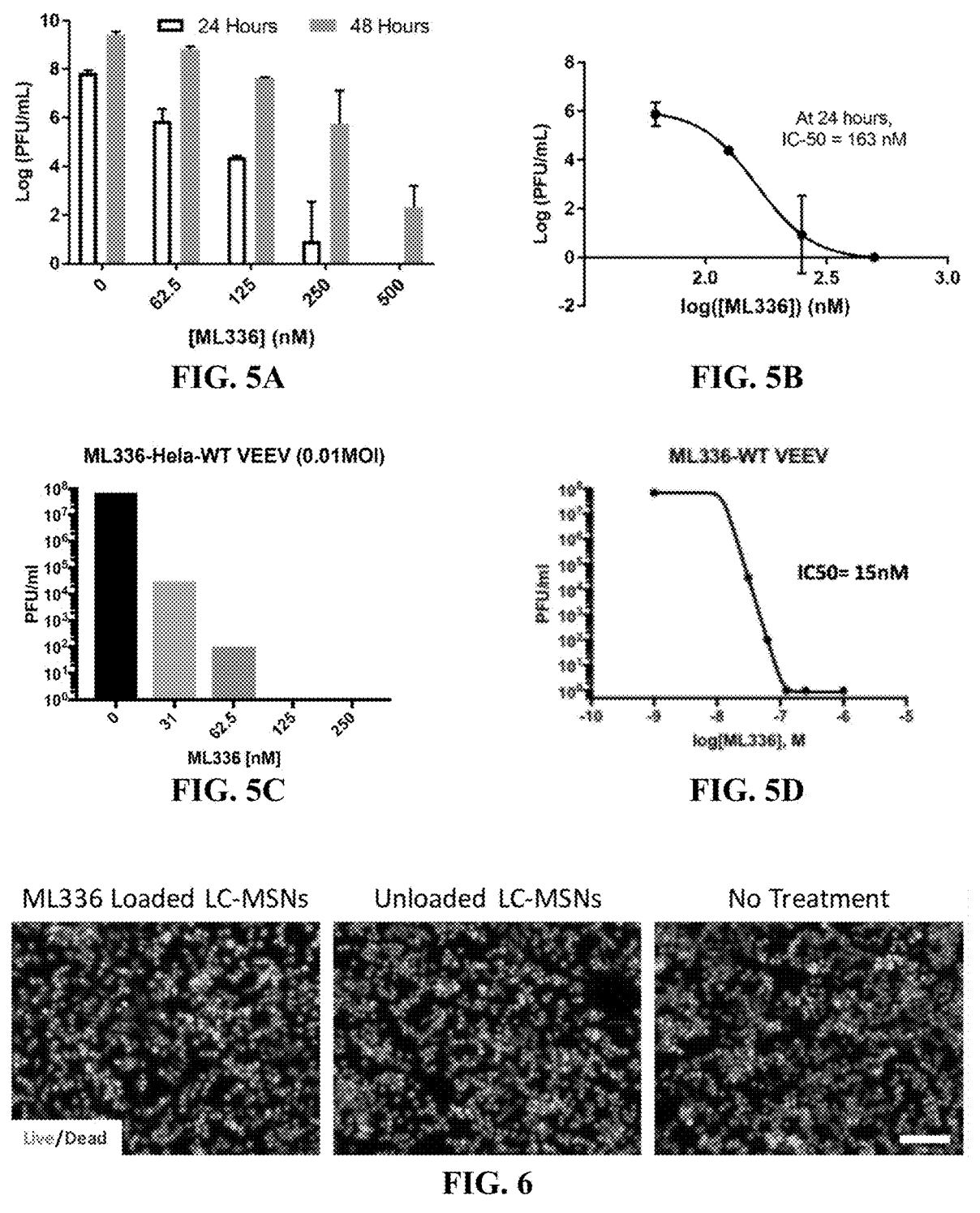

To evaluate the performance of ML336-loaded LC-MSNs in vitro, their ability to inhibit virus in infected HeLa cells was assessed. First, a baseline was determined using soluble ML336, which inhibited TC-83 virus in a dose-dependent manner on HeLa cells with an IC-50 of 163 nM at 24 hrs (FIG. 5A-5B). The wildtype VEEV, a BSL-3 agent, was inhibited by ML336 in a similar manner (FIG. 5C-5D) but was not used in subsequent studies due to associated high risk. The inhibition of VEEV by ML336 observed here was similar to previous studies [4].

Figure 7:
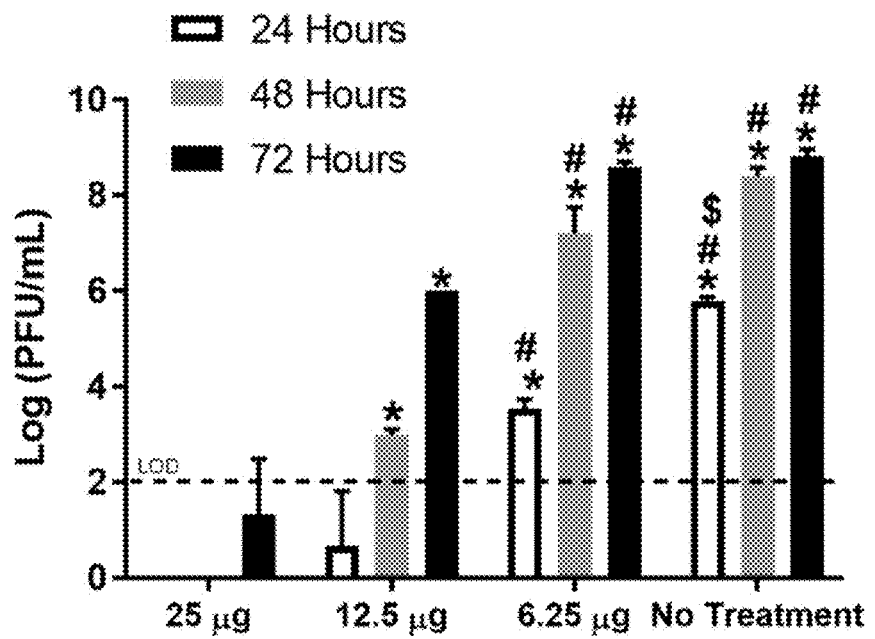
FIG. 7 shows that ML336 loaded LC-MSNs inhibit virus in a dose-dependent manner. *=Significantly different than 25 μg group at same timepoint, #=significantly different than 12.5 μg at the same timepoint, $=significantly different than 6.25 μg group at the same timepoint; p<0.05; data are depicted as mean±standard deviation; n=3.
Figure 8A:
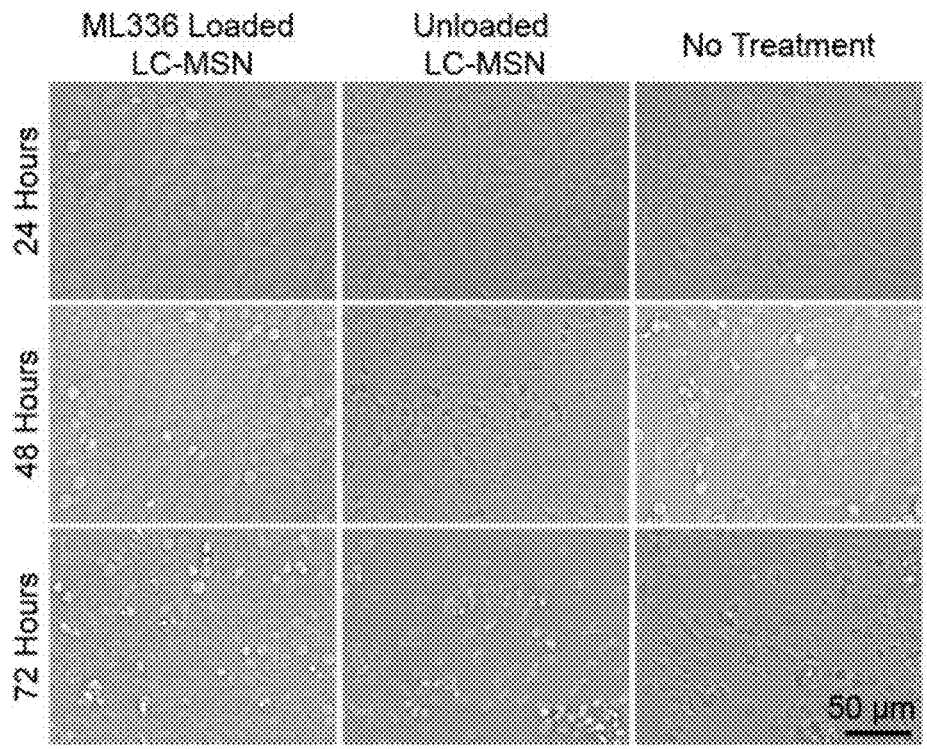
FIG. 8A-8C shows that ML336 loaded LC-MSNs inhibited virus in vitro. Provided are (A) phase microscopy images of cells 24, 48, and 72 hours post infection. Noticeable cell death is observed in the unloaded LC-MSN and no treatment groups, as compared to loaded LC-MSN treatment group; and (B) PFU/mL for loaded, unloaded, and untreated groups. *=Significantly different than loaded group at same timepoint, #=significantly different than unloaded group at the same timepoint; n=3 technical replicates and 3 biological replicates. Also provided is (C) PFU/mL for loaded, supernatant, pre-released, and untreated groups. *=Significantly different than loaded group at same timepoint, #=significantly different than supernatant group at the same timepoint, $=significantly different than pre-released group at the same timepoint; p<0.05; data are depicted as mean±standard deviation, n=3 technical replicates and 5 biological replicates.
Figure 8B:
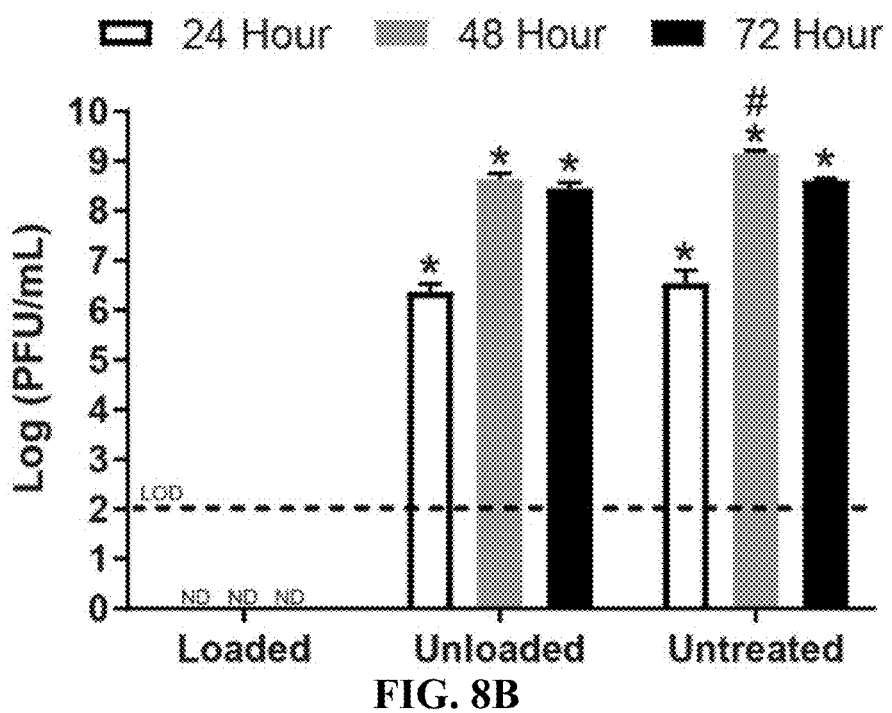
Figure 8C:
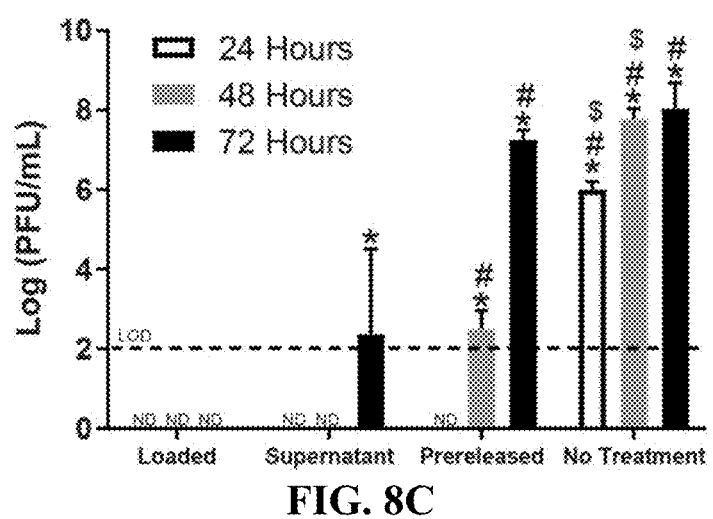
Figure 9A:
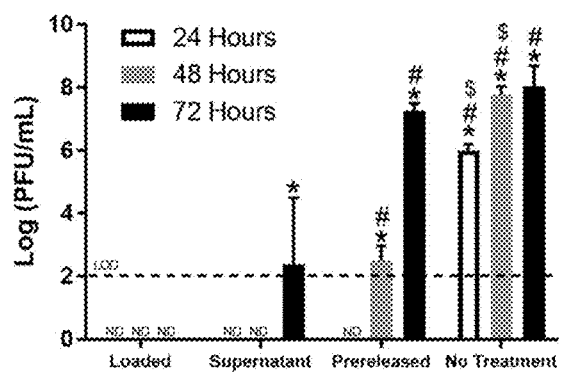
FIG. 9A-9D shows repeatability studies for LC-MSN viral inhibition in vitro. Provided are PFU/mL for loaded, supernatant, pre-released, and untreated groups for (A, C) batch 1 and (B, D) batch 2 in (A, B) study 1 and (C, D) study 2. Note that (A) is also depicted in FIG. 8C. *=Significantly different than loaded group at same timepoint, #=significantly different than supernatant group at the same timepoint, $=significantly different than pre-released group at the same timepoint; p<0.05; data is depicted as mean±standard deviation; n=3 technical replicates and 5 biological replicates.
Figure 9B:
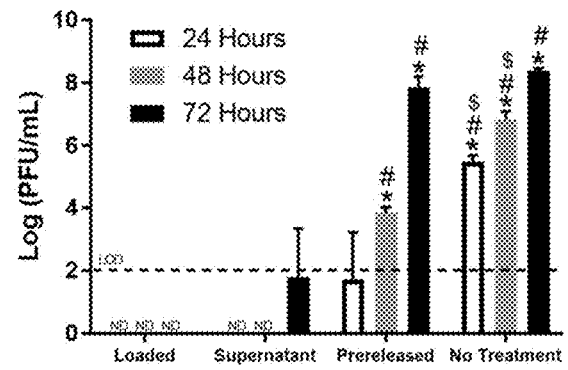
Figure 9C:
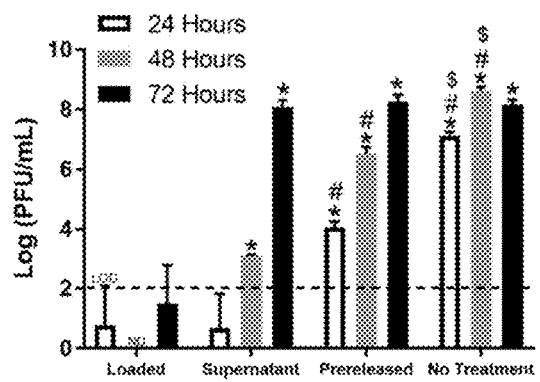
Figure 9D:
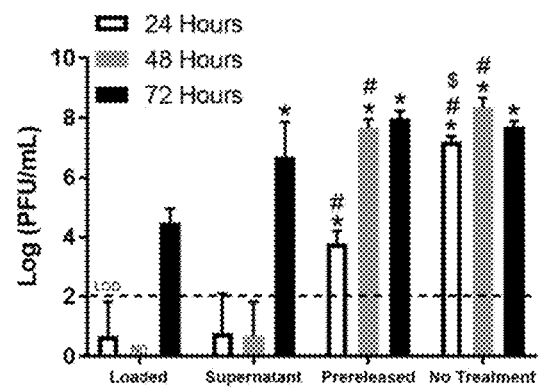

Cytotoxicity of ML336-loaded and unloaded LC-MSNs was assessed with HeLa cells. No visible differences in viability at 48 hrs was observed via LIVE/DEAD staining (FIG. 6), in line with the high biocompatibility observed in cells treated with LC-MSNs previously [19, 33, 37] and with the limited toxicity observed when cells are treated with MSNs at a concentration less than 100 µg/mL [13]. To determine if ML336-loaded LC-MSNs inhibited virus, HeLa cells infected with the TC-83 virus were treated with ML336-loaded and unloaded LC-MSNs. Similar to soluble ML336, ML336-loaded LC-MSNs also inhibited virus in a dose-dependent manner, indicating that total ML336 release is proportional to LC-MSN mass and providing a method to tune drug dosage in a facile manner (FIG. 7). ML336 loaded LC-MSNs significantly decreased viral load by at least 4 orders of magnitude after 24 hrs and 6 orders of magnitude after 48 and 72 hrs (FIG. 8A-8B), a greater reduction than previously observed for other small molecule VEEV inhibitors [9, 11] and similar to what has been observed for soluble ML336 [4]. Overall, these results indicate that ML336 loaded LCMSNs can successfully inhibit VEEV.

As discussed above, little to no additional ML336 release from LC-MSNs incubated in PBS was observed after four hours (FIG. 3E-3F). However, release of hydrophobic ML336 could depend heavily on the local microenvironment, especially if partially controlled by silica degradation [34, 35]. In order to evaluate if LC-MSNs were effective after the initial 4 hour burst release in vitro, ML336 loaded LC-MSNs were incubated in Opti-MEM for 4 hours, called "Pre-released LC-MSNs", and then separated from the supernatant. TC-83 infected HeLa cells were then treated with LC-MSN supernatant and pre-released LC-MSNs and compared to cells treated with loaded LC-MSNs and untreated cells. LC-MSN supernatant inhibited virus at a similar level to ML336 loaded LC-MSNs until the 72 hr timepoint, at which point loaded LC-MSNs inhibited virus to a greater extent (FIG. 8C, FIG. 9A-9D). This indicates that while released ML336 remains bioactive, it is possible that LC-MSNs protect ML336 over time and/or continually release additional ML336 in a manner different from our test tube release studies.

While pre-released LC-MSNs inhibited virus in a similar manner to loaded LC-MSNs and LC-MSN supernatant at 24 hrs, by 48 hrs the extent of viral inhibition was significantly lower than cells treated with loaded LC-MSNs or LC-MSN supernatant. By 72 hrs, pre-released LC-MSNs showed no additional inhibition as compared to cells with no treatment (FIG. 8C, FIG. 9A-9D). This indicates that LC-MSNs release additional ML336 after the initial four hour burst release, which may either be undetectable in the loading and release studies or does not occur prior to cell internalization and disruption of the lipid bilayer [33]. Taken as a whole, this data suggests that release from LC-MSNs occurs for longer than four hrs (possibly up to 48 hrs) and may depend on intracellular uptake. In addition, these studies were reproducible across multiple studies that employed different batches of particles (FIG. 9A-9D), indicating the robustness of the technology as a whole.

Example 5: LC-MSN Cellular Entry Mechanism

To begin to understand the dependency of LC-MSN cellular internalization on lipid bilayer disruption and complete drug cargo release, we first investigated whether LC-MSNs enter cells through endocytosis. LC-MSNs conjugated with affinity ligands are known to enter cells using trafficking pathways of the targeting receptor. For example, cholera toxin B conjugated LC-MSNs use caveolin-mediated endocytosis for internalization after binding the GM1 ganglioside receptor [20]. LC-MSNs have also been formulated to avoid non-specific uptake in blood circulation [19]. However, LC-MSN uptake in static conditions represented in these studies is not well understood.

Figure 10A:
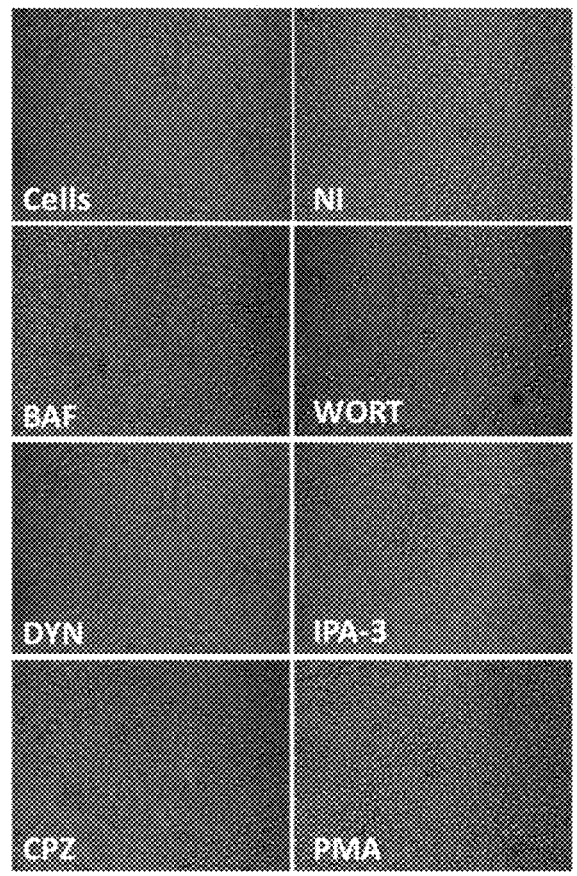
FIG. 10A-10D shows LC-MSN cellular internalization by clathrin-mediated endocytosis. (A) LC-MSNs containing a Cy3 dye label were added to inhibitor treated HeLa cells, and the uptake efficiency was visualized using brightfield and fluorescent image overlays (scale bar=25 μm) or (B) quantified through flow cytometry. The inhibitor panel included those targeting pH dependent endocytosis (BAF), clathrin-mediated endocytosis (DYN, CPZ), macropinocytosis (WORT, IPA-3), and caveola-mediated endocytosis (PMA, DYN), while untreated cells with (NI) and without LC-MSN (cells) addition served as controls. (C,D) HeLa cells treated with Cy3 labeled LC-MSNs for 45 min or 20 hr were fixed and stained for microtubules with anti α-tubulin antibodies, actin with phalloidin, and nuclei with DAPI. Confocal images were acquired, and 3D cell images were subjected to isosurface rendering to reveal time-dependent internalization of LC-MSNs (scale bars=10 μm in (C) and 2

To determine whether LC-MSNs undergo cellular internalization through endocytosis, fluorescent LC-MSNs containing Cy3-labeled MSN cores were used to facilitate visualization and quantitation of entry into HeLa cells while in the presence of various endocytosis inhibitors. Hela cells were treated with a pH dependent endocytosis inhibitor (bafilomycin, BAF), clathrin-mediated endocytosis inhibitors (dynamin II inhibitor dynasore, DYN, and chlorpromazine, CPZ), caveolae-mediacted endocytosis inhibitors (phorbol 12-myristate 13-acetate, PMA and DYN), or macropinocytosis inhibitors (wortmannin, wort, and p21-activated kinase inhibitor III, IPA-3) for 1 hr prior to the addition of Cy3-labeled LC-MSNs. Cells were vigorously washed to remove free particles and then examined by microscopy methods. Cy3-labeled LC-MSNs were readily internalized by Hela cells under untreated or no inhibitor (NI) conditions. LC-MSNs were also clearly inhibited in the presence of BAF, CPZ, and DYN, but not by inhibitors of macropinocytosis (wort, IPA-3) nor caveolin-mediated endocytosis (PMA), suggesting the role of clathrin-mediated endocytosis in cellular internalization of LC-MSNs (FIG. 10A).

Figure 10B:
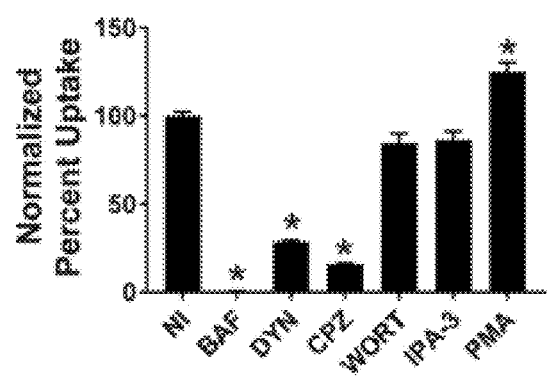

To quantify the results obtained by microscopy, flow cytometry was used to measure the percentage of internalized Cy3-labeled LC-MSNs. HeLa cells were treated with the panel of endocytosis inhibitors for 1 hr prior to and during incubation with fluorescent LC-MSNs. Before flow cytometry analysis, the cells were washed to remove unbound particles. Again, inhibitors of endosomal acidification (BAF) almost completely inhibited LC-MSN internalization, while those of clathrin-mediated endocytosis dramatically reduced LC-MSN uptake. The percentage of cells that internalized LC-MSNs was reduced by 71% with DYN, and 84% with CPZ (FIG. 10B and FIG. 11A) as compared to untreated control conditions, thus correlating with microscopy data. As viruses commonly use endocytosis for cellular entry, we confirmed the specificity of these inhibitors with viruses known to enter HeLa cells via endocytosis using vesicular stomatitis virus for clathrin-mediated endocytosis or Rift Valley fever virus for caveolae-mediated endocytosis dependent entry (FIG. 11B-11C) [38].

Figure 10C:
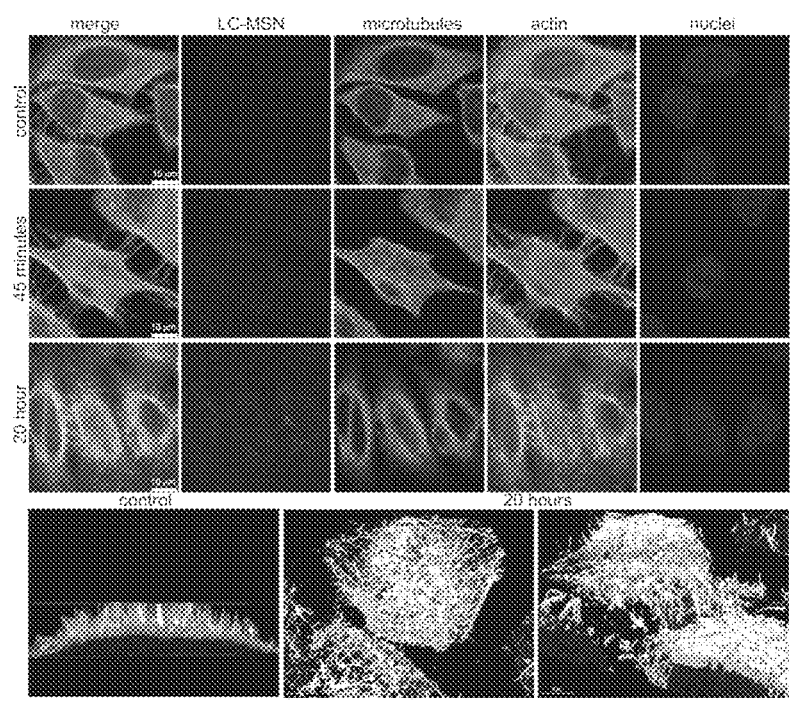
Figure 10D:

To confirm the labeled LC-MSNs were internalized and not on the cell surface, high resolution confocal microscopy techniques were employed. HeLa cells were incubated with LC-MSNs for either 45 min or 20 hrs, washed, and then fixed for immunofluorescence staining. As shown in FIG. 10C-10D, HeLa cells incubated with LC-MSNs for 20 hrs were internalized as indicated by 3D rendering of LC-MSNs with actin, microtubules, and nuclei intracellular markers. An actin stain was used to mark the periphery of the cell as actin filaments are concentrated at the cell periphery and form a 3D network that determines cell shape. Microtubule labeling using tubulin antibodies provided another reference for intracellular localization and depth of LC-MSNs within the cell. LC-MSNs were visualized as beneath actin filaments, on the same plane as the microtubules, and above the cell nucleus. Furthermore, these data indicated a time dependent mechanism of entry as particles were not seen intracellularly at 45 min (FIG. 10C-10D). Taken together, LC-MSNs enter cells through clathrin-mediated endocytosis and may provide a mechanism of additional drug/cargo release at the site of LC-MSN accumulation. Identifying the LC-MSNs cell entry pathway as clathrin-mediated endocytosis may provide a mechanism to design additional drug/cargo release at the site of LC-MSN accumulation. Overall, these results motivated a further investigation of the ability of ML336 loaded LC-MSNs to inhibit virus in vivo.

Example 6: ML336 Loaded LC MSN Viral Inhibition In Vivo

As with all nanoparticle-based systems, the potential for LC-MSNs to dissolve, aggregate, and interact with living cells and animal tissues is dependent upon properties specific to their unique composition [14]. In addition, the toxicity of MSNs and LC-MSNs in general has yet to be fully assessed and can vary depending upon size and surface properties [12, 13, 18]. Thus, prior to conducting animal studies to evaluate antiviral efficacy, a safety study was conducted to determine if the LC-MSNs developed in this work affected mouse weight and survival over fifteen days. Mice were injected with 1 mg LC-MSNs twice daily for four days, and all animals survived treatment with no significant differences in total animal weight between LC-MSN and PBS treated groups (FIG. 12A). Previously, MSNs have been seen to accumulate in the spleen, liver, bladder, and kidneys [13, 14]. In this work, no significant differences were observed between lung, liver, spleen, kidney, or brain weights in animals treated with LC-MSNs as compared to PBS only (FIG. 12B). A lack of weight change in tissue where bioaccumulation was likely the highest (liver, spleen and kidney) further suggests a lack of LC-MSN toxicity. Similarly, tissues processed for histology revealed a normal morphology in brain, spleen, and kidney sections in LC-MSN treated mice while only very mild changes of some sections were seen in livers and lungs of nanoparticle dosed animals (FIG. 12C).

In summary, we observed no toxicity when a 0.11 g LC-MSNs/kg mouse dose was administered each day for four days, resulting in a total possible accumulated mass of silica nanoparticles of 0.44 g/kg. This correlates well with previous work, where MSN toxicity in mice was observed to be problematic when MSN were administered one time at 1.2 g/kg by IV injection [39], but little to no toxicity was observed when 0.2 g/kg was administered once a day for 10 days [40]. The nanoparticles used in the work presented here also include the addition of the lipid bilayer, likely improving biocompatibility, increasing circulation time, and reducing toxicity as compared to uncoated MSNs [12]. Overall, results indicated that administration of LC-MSNs did not cause significant toxicity in mice, motivating further studies to investigate the ability of drug-loaded particles to inhibit viral infection.

In the first set of animal studies, mice were treated with 1 mg loaded LC-MSNs, unloaded LC-MSNs, free ML336, or PBS only. Mice treated with ML336 loaded LC-MSNs showed greater survival than animals in the other three groups, though this result was not statistically significant (FIG. 13A). As we observed that LC-MSNs inhibited virus in a dose-dependent manner in in vitro studies (FIG. 7), we were interested to see if an increased LC-MSN dose would improve animal outcomes. Thus, in the second set of animal studies, animals were dosed with 1.5 mg LC-MSNs. No differences were observed in spleen viral load (FIG. 13C), and very limited viral loads were detected in livers, kidneys, or serum (FIG. 14A-14C), similar to what has been observed in past studies characterizing TC-83 intranasal infection in C3H/HeN mice [8].

However, viral load in the brain was significantly reduced by about 10-fold in the ML336 loaded LC-MSN treated mice as compared to the PBS treated animals after 4 days (FIG. 13B). As viral load in mice treated with free ML336 was not significantly different from PBS treated animals, LC-MSNs may protect ML336 or increase circulation time in a manner that permits enhanced antiviral activity. In the future, a larger number of animals will help further elucidate trends. Overall, these results are encouraging and indicate the potential utility of ML336-loaded LC-MSNs in inhibiting VEEV infection.

No FDA approved therapeutics are available for VEEV [3, 4], though several studies have highlighted the ability of small molecules to inhibit VEEV both in vitro and in vivo [6-11]. Small molecule inhibitors of VEEV has been moderately successful, though drug toxicity has remained an issue [7, 10]. In addition, similar to the results in this study (FIG. 12B), animals treated with small molecule VEEV inhibitors show less than 10-fold brain viral titer reduction as compared to untreated control groups [7, 11], which may result in increased neurological impairment.

Future iterations of the LC-MSNs presented in this work have the potential to improve these outcomes by reducing toxicity and enabling targeting specific to the blood-brain barrier in the case of VEEV infections. First, LC-MSNs can prevent toxicity by 1) reducing the concentration required for drug efficacy, both through improvements in drug solubility/stability as well as circulation time [12, 19], and 2) protecting the cellular microenvironment from harmful cargo prior to triggered release, either through rupture of the lipid bilayer or a specific chemically triggered mechanism [22]. Second, the LC-MSN lipid bilayer can be modified to specifically target a tissue of interest, such as the blood-brain barrier [20, 22]. LC-MSNs are particularly advantageous because properties of the lipid bilayer and the MSN can be independently tuned, enabling simultaneous optimization of the lipid bilayer for tissue-specific targeting and the core to maximize drug-specific loading. Overall, the studies presented here highlight the ability of drug loaded LC-MSNs to prevent viral infection in one particular case, but the versatility and modifiability of this technology will enable use of LC-MSNs to prevent viral infection in a variety of future applications.

Here, we presented the first use of LC-MSNs to deliver ML336 for TC-83 VEEV inhibition both in vitro and in vivo. ML336 loaded LC-MSNs were successfully coated with a lipid bilayer, which significantly improved colloidal stability, and released cargo over the course of 4 hours. Viral loads were reduced by 4-6 orders of magnitude in TC-83 VEEV infected HeLa cells treated with ML336 loaded LC-MSNs, which was repeatable across several particle batches in different studies. Furthermore, in vitro studies could indicate the possibility of additional release of ML336 after cellular internalization via clathrin-mediated endocytosis and enhanced ML336 stability when loaded in LC-MSNs.

Safety studies indicated that LC-MSNs were not toxic in mice at the doses administered in this study. In mice infected with TC-83 VEEV, animals treated with ML336 loaded LC-MSNs showed a significant reduction of viral load in the brain after four days of treatment. Overall, these studies highlight the utility of LC-MSNs for drug delivery in antiviral applications, and provide an additional defense against VEEV and other alphaviruses in the cases of natural infection or bioterrorism.

REFERENCES

1. Atasheva S et al., *Venezuelan equine encephalitis virus capsid protein inhibits nuclear import in Mammalian but not in mosquito cells*. J. Virol. 2008; 82(8):4028-41.
2. Nagata L P et al., *Vaccines and therapeutics for the encephalitic alphaviruses. Future* Virol. 2013; 8(7):661-74.
3. Sidwell R W et al., *Viruses of the Bunya-and Togaviridae families: potential as bioterrorism agents and means of control*. Antiviral Res. 2003; 57(1-2):101-11.
4. Schroeder C E et al., *Development of (E)-2-((1,4-dimethylpiperazin-2-ylidene)amino)-5-nitro-N-phenylbenzamide, ML336: Novel 2-amidinophenylbenzamides as potent inhibitors of Venezuelan equine encephalitis virus*. J. Med. Chem. 2014; 57(20):8608-21.
5. Zacks M A and Paessler S, *Encephalitic alphaviruses*. Vet. Microbiol. 2010; 140(3-4):281-6.
6. Chung D H et al., *Discovery of a novel compound with anti-venezuelan equine encephalitis virus activity that targets the nonstructural protein 2*. PLoS Pathog. 2014; 10(6):e1004213 (10 pp.).
7. Julander J G et al., *Treatment of Venezuelan equine encephalitis virus infection with (−)-carbodine*. Antiviral Res. 2008; 80(3):309-15.
8. Julander J G et al., *C3H/HeN mouse model for the evaluation of antiviral agents for the treatment of Venezuelan equine encephalitis virus infection*. Antiviral Res. 2008; 78(3):230-41.
9. Kehn-Hall K et al., *Modulation of GSK-3beta activity in Venezuelan equine encephalitis virus infection*. PLoS One 2012; 7(4):e34761 (12 pp.).

10. Langsjoen R M et al., *Host oxidative folding pathways offer novel anti-chikungunya virus drug targets with broad spectrum potential*. Antiviral Res. 2017; 143:246-51.

11. Madsen C et al., *Small molecule inhibitors of Ago2 decrease Venezuelan equine encephalitis virus replication*. Antiviral Res. 2014; 112:26-37.

12. Tang F et al., *Mesoporous silica nanoparticles: synthesis, biocompatibility and drug delivery*. Adv. Mater. 2012; 24(12):1504-34.

13. Vivero-Escoto J L et al., *Mesoporous silica nanoparticles for intracellular controlled drug delivery*. Small 2010; 6(18):1952-67.

14. Mamaeva V et al., *Mesoporous silica nanoparticles in medicine—recent advances*. Adv. Drug Deliv. Rev. 2013; 65(5):689-702.

15. Slowing I I et al., *Mesoporous silica nanoparticles as controlled release drug delivery and gene transfection carriers*. Adv. Drug Deliv. Rev. 2008; 60(11):1278-88.

16. Li Z et al., *Mesoporous silica nanoparticles in biomedical applications*. Chem. Soc. Rev. 2012; 41(7):2590-605.

17. Lu J et al., *Mesoporous silica nanoparticles as a delivery system for hydrophobic anticancer drugs*. Small 2007; 3(8):1341-6.

18. Rosenholm J M et al., *Towards multifunctional, targeted drug delivery systems using mesoporous silica nanoparticles—opportunities & challenges*. Nanoscale 2010; 2(10):1870-83.

19. Durfee P N et al., *Mesoporous silica nanoparticle-supported lipid bilayers (protocells) for active targeting and delivery to individual leukemia cells*. ACS Nano 2016; 10(9):8325-45.

20. Gonzalez Porras M A et al., *A novel approach for targeted delivery to motoneurons using cholera toxin-B modified protocells*. J. Neurosci. Methods 2016; 273:160-74.

21. Cauda V et al., *Colchicine-loaded lipid bilayer-coated 50 nm mesoporous nanoparticles efficiently induce microtubule depolymerization upon cell uptake*. Nano Lett. 2010; 10(7):2484-92.

22. Butler K S et al., *Protocells: modular mesoporous silica nanoparticle-supported lipid bilayers for drug delivery*. Small 2016; 12(16):2173-85.

23. Bimbo L M et al., *Inhibition of Influenza A virus infection in vitro by saliphenylhalamide-loaded porous silicon nanoparticles*. ACS Nano 2013; 7(8):6884-93.

24. van Schooneveld M M et al., *Improved biocompatibility and pharmacokinetics of silica nanoparticles by means of a lipid coating: a multimodality investigation*. Nano Lett. 2008. 8(8): 2517-25.

25. Roggers R A et al., *Chemically reducible lipid bilayer coated mesoporous silica nanoparticles demonstrating controlled release and HeLa and normal mouse liver cell biocompatibility and cellular internalization*. Mol. Pharm. 2012; 9(9):2770-7.

26. Teng I T et al., *Phospholipid-functionalized mesoporous silica nanocarriers for selective photodynamic therapy of cancer*. Biomaterials 2013; 34(30):7462-70.

27. Wang L S et al., *Biofunctionalized phospholipid-capped mesoporous silica nanoshuttles for targeted drug delivery: improved water suspensibility and decreased nonspecific protein binding*. ACS Nano 2010; 4(8):4371-9.

28. Tarn D et al., *Mesoporous silica nanoparticle nanocarriers: biofunctionality and biocompatibility*. Acc. Chem. Res. 2013; 46(3):792-801.

29. Mornet S et al., *The formation of supported lipid bilayers on silica nanoparticles revealed by cryoelectron microscopy*. Nano Lett. 2005; 5(2):281-5.

30. Liu J et al., *Porous nanoparticle supported lipid bilayers (protocells) as delivery vehicles*. J. Am. Chem. Soc. 2009; 131(4):1354-5.

31. Han N et al., *Hybrid lipid-capped mesoporous silica for stimuli-responsive drug release and overcoming multidrug resistance*. ACS Appl. Mater. Interfaces 2015; 7(5): 3342-51.

32. Wang D et al., *The eradication of breast cancer cells and stem cells by 8 hydroxyquinoline-loaded hyaluronan modified mesoporous silica nanoparticle-supported lipid bilayers containing docetaxel*. Biomaterials 2013; 34(31): 7662-73.

33. Zhang X et al., *Biofunctionalized polymer-lipid supported mesoporous silica nanoparticles for release of chemotherapeutics in multidrug resistant cancer cells*. Biomaterials 2014; 35(11):3650-65.

34. von Haartman E et al., *On the intracellular release mechanism of hydrophobic cargo and its relation to the biodegradation behavior of mesoporous silica nanocarriers*. Eur. J. Pharm. Sci. 2016; 95:17-27.

35. Braun K et al., *Dissolution kinetics of mesoporous silica nanoparticles in different simulated body fluids*. J. Sol-Gel Sci. Technol. 2016; 79(2):319-27.

36. Maleki A et al., *Mesoporous silica materials: from physico-chemical properties to enhanced dissolution of poorly water-soluble drugs*. J. Control. Release 2017; 262:329-47.

37. Han D H et al., *Direct cellular delivery of human proteasomes to delay tau aggregation*. Nat. Commun. 2014; 5:5633 (8 pp.).

38. Harmon B et al., *Rift Valley fever virus strain MP-12 enters mammalian host cells via caveola-mediated endocytosis*. J. Virol. 2012; 86:12954-70.

39. Riikonen J et al., *Systematic in vitro and in vivo study on porous silicon to improve the oral bioavailability of celecoxib*. Biomaterials 2015; 52:44-55.

40. Lu J et al., *Biocompatibility, biodistribution, and drug-delivery efficiency of mesoporous silica nanoparticles for cancer therapy in animals*. Small 2010; 6(16):1794-805.

41. Townson J L et al., *Re-examining the size/charge paradigm: differing in vivo characteristics of size- and charge-matched mesoporous silica nanoparticles*. J. Am. Chem. Soc. 2013; 135:16030-3.

42. Lin Y S et al., *Stability of small mesoporous silica nanoparticles in biological media*. Chem. Commun. (Camb.) 2011; 47:532-4.

43. Sherman M B et al., *Stability of cucumber necrosis virus at the quasi-6-fold axis affects zoospore transmission*. J. Virol. 2017; 91:1-12.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. An antiviral carrier and compound comprising:
   a porous core comprising a plurality of pores;
   an antiviral compound disposed in at least one pore; and
   a lipid layer disposed around the porous core,
   wherein the antiviral compound has an aqueous solubility of from about 20 μg/mL to about 150 μg/mL in phosphate-buffered saline at a pH of 7.4 and/or a stability of about 80% or less of a remaining amount of the compound after incubating in plasma for about 3 hours;
   wherein the compound has a structure of formula (I):

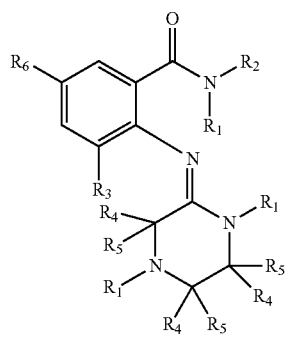

or a salt thereof;
wherein:
   each $R_1$, $R_3$, $R_4$, $R_5$, and $R_6$ are H; and
   $R_2$ is substituted aryl.

2. The antiviral carrier and compound of claim 1, further comprising a pharmaceutically acceptable excipient.

3. The antiviral carrier and compound of claim 1, wherein the antiviral compound is present in an amount of from about 10 μg/mg to 50 μg/mg (μg of the compound per mg of the carrier).

4. The antiviral carrier and compound of claim 1, wherein the antiviral compound has a release rate of from about 3 μg/mg to about 20 μg/mg (μg of the compound per mg of the carrier) over a period of about 24 hours in vitro.

5. The antiviral carrier and compound of claim 1, wherein the lipid layer comprises a zwitterionic lipid, a cholesterol or a derivative thereof, and a pegylated lipid.

6. The antiviral carrier and compound of claim 3, wherein the antiviral compound has a release rate of from about 3 μg/mg to about 20 μg/mg (μg of the compound per mg of the carrier) over a period of about 24 hours in vitro;
   wherein the lipid layer comprises a zwitterionic lipid, a cholesterol or a derivative thereof, and a pegylated lipid.

7. The antiviral carrier and compound of claim 5, wherein the antiviral compound has a release rate of from about 3 μg/mg to about 20 μg/mg (μg of the compound per mg of the carrier) over a period of about 24 hours in vitro.

8. The antiviral carrier and compound of claim 1, wherein the lipid layer includes about 10 to about 50 mol. % DOTAP, about 40 to 50 mol. % cholesterol, about 0 to 40 mol. % DOPE, and about 1 to 5 mol. % of a PEGylated lipid.

9. The antiviral carrier of claim 1, wherein the antiviral compound is hydrophobic or lipophilic.

10. The antiviral carrier and compound of claim 1, wherein the antiviral compound has an aqueous solubility of from about 20 μg/mL to about 150 μg/mL in phosphate-buffered saline at a pH of 7.4.

11. The antiviral carrier and compound of claim 1, wherein the antiviral compound has a stability of about 80% or less of a remaining amount of the compound after incubating in plasma for about 3 hours.

12. The antiviral carrier and compound of claim 1, wherein the antiviral compound has an $EC_{50}$ value of from about 0.01 μM to about 1 μM as determined in a cellular assay.

13. The antiviral carrier and compound of claim 12, wherein the antiviral compound has an $EC_{90}$ value of from about 100 nM to about 300 nM as determined in a cellular assay.

14. The antiviral carrier and compound of claim 1, wherein the antiviral compound is hydrophobic.

15. The antiviral carrier and compound of claim 1, wherein the antiviral compound is lipophilic.

16. The antiviral carrier and compound of claim 10, wherein the antiviral compound has a stability of about 80% or less of a remaining amount of the compound after incubating in plasma for about 3 hours.

17. The antiviral carrier and compound of claim 1, wherein the compound is the salt of the structure of formula (I).

18. The antiviral carrier and compound of claim 1, wherein the compound is the structure of formula (I).

19. The antiviral carrier and compound of claim 8, wherein the antiviral compound has an $EC_{50}$ value of from about 0.01 μM to about 1 μM as determined in a cellular assay.

20. The antiviral carrier and compound of claim 17, wherein the lipid layer includes about 10 to about 50 mol. % DOTAP, about 40 to 50 mol. % cholesterol, about 0 to 40 mol. % DOPE, and about 1 to 5 mol. % of a PEGylated lipid.

* * * * *

SEQUENCE LISTING

<160> NUMBER OF SEQ ID NOS: 49

<210> SEQ ID NO 1
<211> LENGTH: 8
<212> TYPE: PRT
<213> ORGANISM: Artificial Sequence
<220> FEATURE:
<223> OTHER INFORMATION: Synthetic construct

<400> SEQUENCE: 1

Arg Arg Arg Arg Arg Arg Arg Arg
1               5

<210> SEQ ID NO 2
<211> LENGTH: 25
<212> TYPE: PRT
<213> ORGANISM: Artificial Sequence
<220> FEATURE:
<223> OTHER INFORMATION: Synthetic construct

<400> SEQUENCE: 2

Gly Leu Phe His Ala Ile Ala His Phe Ile His Gly Gly Trp His Gly
1               5                   10                  15

Leu Ile His Gly Trp Tyr Gly Gly Cys
            20                  25

<210> SEQ ID NO 3
<211> LENGTH: 30
<212> TYPE: PRT
<213> ORGANISM: Artificial Sequence
<220> FEATURE:
<223> OTHER INFORMATION: Synthetic construct

<400> SEQUENCE: 3

Trp Glu Ala Arg Leu Ala Arg Ala Leu Ala Arg Ala Leu Ala Arg His
1               5                   10                  15

Leu Ala Arg Ala Leu Ala Arg Ala Leu Arg Ala Gly Glu Ala
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic construct

<400> SEQUENCE: 4

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Gly Glu Ala
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Synthetic construct

<400> SEQUENCE: 5

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 6
<211> LENGTH: 23
<212> TYPE: PRT
<213> ORGANISM: Artificial Sequence
<220> FEATURE:
<223> OTHER INFORMATION: Synthetic construct

<400> SEQUENCE: 6

Gly Leu Phe Glu Ala Ile Glu Gly Phe Ile Glu Asn Gly Trp Glu Gly
1               5                   10                  15

Met Ile Asp Gly Trp Tyr Gly
            20

<210> SEQ ID NO 7

<400> SEQUENCE: 7

000

<210> SEQ ID NO 8

<400> SEQUENCE: 8

000

<210> SEQ ID NO 9
<211> LENGTH: 42
<212> TYPE: PRT
<213> ORGANISM: Artificial Sequence
<220> FEATURE:
<223> OTHER INFORMATION: Synthetic construct

<400> SEQUENCE: 9

Gly Asn Gln Ser Ser Asn Phe Gly Pro Met Lys Gly Gly Asn Phe Gly
1               5                   10                  15

Gly Arg Ser Ser Gly Pro Tyr Gly Gly Gly Gln Tyr Phe Ala Lys
            20                  25                  30

Pro Arg Asn Gln Gly Gly Tyr Gly Gly Cys
        35                  40

<210> SEQ ID NO 10
<211> LENGTH: 7
<212> TYPE: PRT
<213> ORGANISM: Artificial Sequence
<220> FEATURE:
<223> OTHER INFORMATION: Synthetic construct

<400> SEQUENCE: 10

Arg Arg Met Lys Trp Lys Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic construct

<400> SEQUENCE: 11

Pro Lys Lys Lys Arg Lys Val
1               5

<210> SEQ ID NO 12
<211> LENGTH: 16
<212> TYPE: PRT

```
<213> ORGANISM: Artificial Sequence
<220> FEATURE:
<223> OTHER INFORMATION: Synthetic construct

<400> SEQUENCE: 12

Lys Arg Pro Ala Ala Thr Lys Lys Ala Gly Gln Ala Lys Lys Lys
1               5                   10                  15

<210> SEQ ID NO 13
<211> LENGTH: 12
<212> TYPE: PRT
<213> ORGANISM: Artificial Sequence
<220> FEATURE:
<223> OTHER INFORMATION: Synthetic construct

<400> SEQUENCE: 13

Ser Phe Ser Ile Ile Leu Thr Pro Ile Leu Pro Leu
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Synthetic construct

<400> SEQUENCE: 14

Ser Phe Ser Ile Ile Leu Thr Pro Ile Leu Pro Leu Gly Gly Cys
1               5                   10                  15

<210> SEQ ID NO 15
<211> LENGTH: 18
<212> TYPE: PRT
<213> ORGANISM: Artificial Sequence
<220> FEATURE:
<223> OTHER INFORMATION: Synthetic construct

<400> SEQUENCE: 15

Ser Phe Ser Ile Ile Leu Thr Pro Ile Leu Pro Leu Glu Glu Glu Gly
1               5                   10                  15

Gly Cys

<210> SEQ ID NO 16
<211> LENGTH: 7
<212> TYPE: PRT
<213> ORGANISM: Artificial Sequence
<220> FEATURE:
<223> OTHER INFORMATION: Synthetic construct

<400> SEQUENCE: 16

Ala Ser Val His Phe Pro Pro
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic construct

<400> SEQUENCE: 17

Thr Ala Thr Phe Trp Phe Gln
1               5

<210> SEQ ID NO 18
<211> LENGTH: 7
```

```
<212> TYPE: PRT
<213> ORGANISM: Artificial Sequence
<220> FEATURE:
<223> OTHER INFORMATION: Synthetic construct

<400> SEQUENCE: 18

Thr Ser Pro Val Ala Leu Leu
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic construct

<400> SEQUENCE: 19

Ile Pro Leu Lys Val His Pro
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic construct

<400> SEQUENCE: 20

Trp Pro Arg Leu Thr Asn Met
1               5

<210> SEQ ID NO 21
<211> LENGTH: 12
<212> TYPE: PRT
<213> ORGANISM: Artificial Sequence
<220> FEATURE:
<223> OTHER INFORMATION: Synthetic construct

<400> SEQUENCE: 21

Arg Arg Arg Arg Arg Arg Arg Arg Arg Arg Arg Arg
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Synthetic construct

<400> SEQUENCE: 22

Arg Arg Arg Arg Arg Arg Arg Arg Arg
1               5

<210> SEQ ID NO 23
<211> LENGTH: 18
<212> TYPE: PRT
<213> ORGANISM: Artificial Sequence
<220> FEATURE:
<223> OTHER INFORMATION: Synthetic construct

<400> SEQUENCE: 23

Lys His Lys His Lys His Lys His Lys His Lys His Lys His Lys His
1               5                   10                  15

Lys His

<210> SEQ ID NO 24
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 24

Arg Lys Lys Arg Arg Gln Arg Arg Arg
1               5

<210> SEQ ID NO 25
<211> LENGTH: 12
<212> TYPE: PRT
<213> ORGANISM: Artificial Sequence
<220> FEATURE:
<223> OTHER INFORMATION: Synthetic construct

<400> SEQUENCE: 25

Gly Arg Lys Lys Arg Arg Gln Arg Arg Arg Pro Gln
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic construct

<400> SEQUENCE: 26

Gly Arg Lys Lys Arg Arg Gln Arg Arg Arg
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic construct

<400> SEQUENCE: 27

Gly Arg Lys Lys Arg Arg Gln Arg Arg Arg Pro Pro Gln
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic construct

<400> SEQUENCE: 28

Tyr Gly Arg Lys Lys Arg Arg Gln Arg Arg Arg
1               5                   10

<210> SEQ ID NO 29
<211> LENGTH: 18
<212> TYPE: PRT
<213> ORGANISM: Artificial Sequence
<220> FEATURE:
<223> OTHER INFORMATION: Synthetic construct

<400> SEQUENCE: 29

Arg Lys Lys Arg Arg Gln Arg Arg Arg Lys Lys Arg Arg Gln Arg
1               5                   10                  15

Arg Arg
```

```
<210> SEQ ID NO 30
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Acetylation
<220> FEATURE:
<221> NAME/KEY: MOD_RES
<222> LOCATION: (20)..(20)
<223> OTHER INFORMATION: Cysteamide

<400> SEQUENCE: 30

Gly Leu Trp Arg Ala Leu Trp Arg Leu Leu Arg Ser Leu Trp Arg Leu
1               5                   10                  15

Leu Trp Arg Ala
            20

<210> SEQ ID NO 31
<211> LENGTH: 18
<212> TYPE: PRT
<213> ORGANISM: Artificial Sequence
<220> FEATURE:
<223> OTHER INFORMATION: Synthetic construct

<400> SEQUENCE: 31

Arg Gln Ile Lys Ile Trp Phe Gln Asn Arg Arg Met Lys Trp Lys Lys
1               5                   10                  15

Gly Gly

<210> SEQ ID NO 32
<211> LENGTH: 16
<212> TYPE: PRT
<213> ORGANISM: Artificial Sequence
<220> FEATURE:
<223> OTHER INFORMATION: Synthetic construct

<400> SEQUENCE: 32

Arg Gln Ile Arg Ile Trp Phe Gln Asn Arg Arg Met Arg Trp Arg Arg
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic construct

<400> SEQUENCE: 33

Arg Gln Ile Lys Ile Trp Phe Gln Asn Arg Arg Met Lys Trp Lys Lys
1               5                   10                  15

<210> SEQ ID NO 34
<211> LENGTH: 17
<212> TYPE: PRT
<213> ORGANISM: Artificial Sequence
<220> FEATURE:
<223> OTHER INFORMATION: Synthetic construct

<400> SEQUENCE: 34

Cys Ser Ile Pro Pro Glu Val Lys Phe Asn Lys Pro Phe Val Tyr Leu
1               5                   10                  15

Ile
```

<210> SEQ ID NO 35
<211> LENGTH: 13
<212> TYPE: PRT
<213> ORGANISM: Artificial Sequence
<220> FEATURE:
<223> OTHER INFORMATION: Synthetic construct

<400> SEQUENCE: 35

Phe Val Gln Trp Phe Ser Lys Phe Leu Gly Arg Ile Leu
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Synthetic construct

<400> SEQUENCE: 36

Lys Leu Ala Leu Lys Leu Ala Leu Lys Ala Leu Lys Ala Ala Leu Lys
1               5                   10                  15

Leu Ala

<210> SEQ ID NO 37
<211> LENGTH: 9
<212> TYPE: PRT
<213> ORGANISM: Artificial Sequence
<220> FEATURE:
<223> OTHER INFORMATION: Synthetic construct

<400> SEQUENCE: 37

Arg Arg Trp Trp Arg Arg Trp Arg Arg
1               5

<210> SEQ ID NO 38
<211> LENGTH: 18
<212> TYPE: PRT
<213> ORGANISM: Artificial Sequence
<220> FEATURE:
<223> OTHER INFORMATION: Synthetic construct

<400> SEQUENCE: 38

Leu Leu Ile Ile Leu Arg Arg Arg Ile Arg Lys Gln Ala His Ala His
1               5                   10                  15

Ser Lys

<210> SEQ ID NO 39
<211> LENGTH: 27
<212> TYPE: PRT
<213> ORGANISM: Artificial Sequence
<220> FEATURE:
<223> OTHER INFORMATION: Synthetic construct

<400> SEQUENCE: 39

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
                20                  25

<210> SEQ ID NO 40
<211> LENGTH: 27
<212> TYPE: PRT
<213> ORGANISM: Artificial Sequence
<220> FEATURE:
<223> OTHER INFORMATION: Synthetic construct

```
<400> SEQUENCE: 40

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 41
<211> LENGTH: 21
<212> TYPE: PRT
<213> ORGANISM: Artificial Sequence
<220> FEATURE:
<223> OTHER INFORMATION: Synthetic construct

<400> SEQUENCE: 41

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 42
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Acetylation
<220> FEATURE:
<221> NAME/KEY: MOD_RES
<222> LOCATION: (21)..(21)
<223> OTHER INFORMATION: Cysteamine

<400> SEQUENCE: 42

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 43
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (11)..(11)
<223> OTHER INFORMATION: Amidation

<400> SEQUENCE: 43

Trp Lys Leu Phe Lys Lys Ile Leu Lys Val Leu
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic construct

<400> SEQUENCE: 44

Lys Lys Leu Phe Lys Lys Ile Leu Lys Tyr Leu
1               5                   10
```

<210> SEQ ID NO 45
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (11)..(11)
<223> OTHER INFORMATION: Amidation

<400> SEQUENCE: 45

Lys Lys Leu Phe Lys Lys Ile Leu Lys Tyr Leu
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (3)..(3)
<223> OTHER INFORMATION: S-Acetomidomethylation

<400> SEQUENCE: 46

Gly Asp Cys Leu Pro His Leu Lys Leu Cys
1               5                   10

<210> SEQ ID NO 47
<211> LENGTH: 24
<212> TYPE: PRT
<213> ORGANISM: Artificial Sequence
<220> FEATURE:
<223> OTHER INFORMATION: Synthetic construct

<400> SEQUENCE: 47

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 48
<211> LENGTH: 30
<212> TYPE: PRT
<213> ORGANISM: Artificial Sequence
<220> FEATURE:
<223> OTHER INFORMATION: Synthetic construct

<400> SEQUENCE: 48

Gly Ala Ala Glu Ala Ala Ala Arg Val Tyr Asp Leu Gly Leu Arg Arg
1               5                   10                  15

Leu Arg Gln Arg Arg Arg Leu Arg Arg Glu Arg Val Arg Ala
            20                  25                  30

<210> SEQ ID NO 49
<211> LENGTH: 27
<212> TYPE: PRT
<213> ORGANISM: Artificial Sequence
<220> FEATURE:
<223> OTHER INFORMATION: Synthetic construct

<400> SEQUENCE: 49

Met Gly Leu Gly Leu His Leu Leu Val Leu Ala Ala Ala Leu Gln Gly
1               5                   10                  15

```
Ala Trp Ser Gln Pro Lys Lys Lys Arg Lys Val
            20                  25
```